US010633637B2

(12) United States Patent
Victoria et al.

(10) Patent No.: US 10,633,637 B2
(45) **Date of Patent: *Apr. 28, 2020**

(54) PESTIVIRUS VACCINES FOR CONGENITAL TREMORS

(71) Applicants: Boehringer Ingelheim Vetmedica GmbH, Ingelheim am Rhein (DE); Iowa State University Research Foundation, Inc., Ames, IA (US)

(72) Inventors: Joseph Gilbert Victoria, Ames, IA (US); Abby Rae Patterson, Story City, IA (US); Callie Ann Visek, Ames, IA (US); Arun V. Iyer, Ames, IA (US); Lea Ann Hobbs, Nevada, IA (US); Bailey Lauren Arruda, Ames, IA (US); Paulo Henrique Elias Arruda, Ames, IA (US); Drew Robert Magstadt, Ames, IA (US); Kent Jay Schwartz, Story City, IA (US)

(73) Assignees: Boehringer Ingelheim Vetmedica GmbH, Ingelheim am Rhein (DE); Iowa State University Research Foundation, Inc., Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/893,358

(22) Filed: Feb. 9, 2018

(65) Prior Publication Data

US 2018/0171307 A1 Jun. 21, 2018

Related U.S. Application Data

(63) Continuation of application No. 15/253,511, filed on Aug. 31, 2016, now Pat. No. 9,920,302.

(60) Provisional application No. 62/212,124, filed on Aug. 31, 2015.

(51) Int. Cl.

| | |
|---|---|
| ***C12N 7/00*** | (2006.01) |
| ***A61K 39/12*** | (2006.01) |
| ***A61K 39/00*** | (2006.01) |

(52) U.S. Cl.

CPC ................ *C12N 7/00* (2013.01); *A61K 39/12* (2013.01); *A61K 2039/5252* (2013.01); *A61K 2039/54* (2013.01); *A61K 2039/545* (2013.01); *A61K 2039/552* (2013.01); *C12N 2770/24334* (2013.01)

(58) Field of Classification Search

None

See application file for complete search history.

(56) References Cited

U.S. PATENT DOCUMENTS

| | | | | |
|---|---|---|---|---|
| 3,456,053 | A | 7/1969 | Crawford | |
| 9,920,302 | B2 * | 3/2018 | Victoria .................. | C12N 7/00 |
| 2002/0086033 | A1 | 7/2002 | Thiel | |
| 2017/0058266 | A1 | 3/2017 | Victoria et al. | |
| 2018/0171307 | A1 * | 6/2018 | Victoria .................. | C12N 7/00 |

FOREIGN PATENT DOCUMENTS

| | | |
|---|---|---|
| WO | 2016/097245 | 6/2016 |
| WO | 2016/176624 | 11/2016 |

OTHER PUBLICATIONS

Arruda et al., "Identification of a Divergent Lineage Porcine Pestivirus in Nursing Piglets with Congenital Tremors and Reproduction of Disease following Experimental Inoculation," *PLoS ONE.* 11 (2): e0150104 (2016).
Arruda et al., "Discovery of a divergent lineage pestivirus in piglets with congenital tremors and reproduction of disease following experimental challenge," *American Association of SwineVeterinarians* 69-70 (2016).
Bjorklund et al., "Phylogenetic Comparison and Molecular Epidemiology of Classical Swine Fever Virus," *Virus Genes* 19:3 189-195 (1999).
Blomstrom et al., "Astrovirus as a possible cause of congenital tremor type AII in piglets?" *Acta Veterinaria Scandinavica* 56(82): 1-6 (2014).
Brunborg et al., "Association of myocarditis with high viral load of porcine circovirus type 2 in several tissues in cases of fetal death and high mortality in piglets. A case study" *J Vet Diagn Invest* 19:368-375 (2007).
Database ENA[Online] Aug. 7, 2015 (Aug. 7, 2015), Porcine pestivirus 1 strain 000515 polyprotein mRNA, complete cds. retrieved from EBI accession No. EM_STD:KR011347 Database accession No. KR011347.
Database ENA [Online] Feb. 2, 2016 (Feb. 2, 2016), "Porcine pestivirus 1 isolate ISDVDL2014016573 polyprotein gene, complete cds.", retrieved from EBI accession No. EM_STD:KU 194229 Database accession No. KU194229.
Database UniProt [Online] Apr. 13, 2016 (Apr. 13, 2016), "RecName: Full=Genome polyprotein {ECO:0000256| SAAS:SAAS00058068};", retrieved from EBI accession No. UniProt:A0A120H3X4 Database accession No. A0A120H3X4.
Edwards, "Survival and inactivation of classical swine fever virus", *Veterinary Microbiology* 73(2-3): 175-181 (2000).
Ha et al., "Lack of evidence of porcine circovirus type 1 and type 2 infection in piglets with congenital tremors in Korea," *Veterinary Record* 156(12):383-384 (2005).
Harding et al., "Congenital tremors in piglets and their relation to swine fever", *Veterinary Record* 79 (14): 388-390 (1966).

(Continued)

*Primary Examiner* — Shanon A. Foley
(74) *Attorney, Agent, or Firm* — Fish & Richardson P.C.

(57) ABSTRACT

The present invention relates to a vaccine for protecting a piglet against diseases associated with a novel pestivirus. The vaccine commonly includes a pestivirus antigen and, optionally an adjuvant. Methods for protecting pigs against diseases associated with pestivirus, including but not limited to congenital tremors and methods of producing the pestivirus vaccine are also provided.

32 Claims, 7 Drawing Sheets

Specification includes a Sequence Listing.

(56) References Cited

OTHER PUBLICATIONS

Hause et al., "Discovery of a novel putative atypical porcine pestivirus in pigs in the USA," *Journal of General Virology* 96(10): 2994-2998 (2015).
International Search Report and Written Opinion for PCT/S2016/049709, dated Dec. 19, 2016 (14 pages).
Iowa State University of Science and Technology, Veterinary Diagnostic Laboratory (ISUVDL) [online] "Identification of a pestivirus in piglets with congenital tremors and reproduction of disease following experimental inoculation" Sep. 24, 2015 [retrieved on Sep. 24, 2015] from the Internet: URL http://vetmed.iastate.edu/sites/default/files/vdl/disease-topics/pestivirus.pdf 1 page.
Jasna et al., "Passive immunity evaluation in piglets originating from sows vaccinated with china strain of classical swine fever virus," *Acta Veterinaria-Beograd* 57 (5-6): 413-427 (2007).
Kennedy et al., "Absence of evidence of porcine circovirus infection in piglets with congenital tremors," *J Vet Diagn Invest* 15:151-156 (2003).
Kummerer et al., "The genetic basis for cytopathogenicity of pestiviruses," *Veterinary Microbiology* 77(1-2): 117-128 (2000).
Moennig et al., "Clinical signs and epidemiology of classical swine fever: a review of new knowledge", *The Veterinary Journal* 165(1): 11-20 (2003).
Osterhaus et al., "Control and eradication of Classic Swine Fever in wild boar and Animal health safety of fresh meat derived from pigs vaccinated against Classic Swine Fever 2 Scientific opinions of the Panel on Animal Health and Welfare." (2007).
Porter et al, "Hypomyelination Associated with Bovine Viral Diarrhea Virus Type 2 Infection in a Longhorn Calf," *Veterinary Pathology* 47(4):658-663 (2010).
Postel et al., "Improved strategy for phylogenetic analysis of classical swine fever virus based on full-length E2 encoding sequences," *Veterinary Research* 43(50): 1-15 (2012).
Pogranichniy, Roman M: "Retrospective Theses and Dissertations 2005 Search for etiology of porcine reproductive and neurologic syndrome: identification and characterization of a novel swine pestivirus Recommended Citation", , Retrieved from the Internet: URL:http://lib.dr.iastate.edu/cgi/viewcontent.cgi?article=2330&context=rtd [retrieved on Nov. 15, 2016].
Schwartz, Kent, "Identification of a Pestivirus in Piglets with Congenital Tremors and Reproduction of Disease following Experimental Inoculation" Sep. 30, 2015 [retrieved on May 23, 2016] from the Internet: URL https://www.aasv/org/news/story.php?id=8380 1 page.
Soos et al., "Evaluation of vaccine-induced maternal immunity against classical swine fever," *Acta Veterinaria Hungarica* 49 (1): 17-24 (2001), abstract only.
Tao et al., "Bovine viral diarrhea virus (BVDV) infections in pigs", *Veterinary Microbiology* 165: 185-189 (2013).
van Rijn et al., "An experimental marker vaccine and accompanying serological diagnostic test both based on envelope glycoprotein E2 of classical swine fever virus (CSFV)", *Vaccine* 17(5): 433-440 (1999).
Vannier et al., "Congenital tremor in pigs farrowed from sows given hog cholera virus during pregnancy," *American Journal of Veterinary Research* 42 (1): 135-137 (1981), abstract only).
Vilcek et al., "Genetic variability of classical swine fever virus," *Virus Research* 43:137-147 (1996).
Vilcek et al., "Organization and Diversity of the 3'-noncoding Region of Classical Swine Fever Virus Genome" *Virus Genes* 15(2): 181-186 (1997).
Sequence alignment of SEQ ID No. 1 with GenEmbl database access No. KU194229 by Arruda et al. in PLoSOne 11 issue 2-E0150104 on Mar. 2016.
Sequence alignment of SEQ ID No. 3 with GenEmbl database access No. KU194229 by Arruda et al. in PLoSOne 11 issue 2-E0150104 on Mar. 2016.
Sequence alignment of SEQ ID No. 5 with GenEmbl database access No. KU194229 by Arruda et al. in PLoSOne 11 issue 2-E0150104 on Mar. 2016.
Sequence alignment of SEQ ID No. 7 with GenEmbl database access No. KU194229 by Arruda et al. in PLoSOne 11 issue 2-E0150104 on Mar. 2016.
Sequence alignment of SEQ ID No. 9 with GenEmbl database access No. KU194229 by Arruda et al. in PLoSOne 11 issue 2-E0150104 on Mar. 2016.
Sequence alignment of SEQ ID No. 11 with GenEmbl database access No. KU194229 by Arruda et al. in PLoSOne 11 issue 2-E0150104 on Mar. 2016.
Sequence alignment of SEQ ID No. 13 with GenEmbl database access No. KU194229 by Arruda et al. in PLoSOne 11 issue 2-E0150104 on Mar. 2016.
Sequence alignment of SEQ ID No. 15 with GenEmbl database access No. KU194229 by Arruda et al. in PLoSOne 11 issue 2-E0150104 on Mar. 2016.
Sequence alignment of SEQ ID No. 17 with GenEmbl database access No. KU194229 by Arruda et al. in PLoSOne 11E0150104 on Mar. 2016.
Sequence alignment of SEQ ID No. 19 with GenEmbl database access No. KU194229 by Arruda et al. in PLoSOne 11E0150104 on Mar. 2016.
Sequence alignment of SEQ ID No. 21 with GenEmbl database access No. KU194229 by Arruda et al. in PLoSOne 11E0150104 on Mar. 2016.
Non-final Office Action in U.S. Appl. No. 15/253,511, dated May 26, 2018, 13 pages.
Written Opinion in Thailand Patent Application No. 1701006506 dated Oct. 16, 2018, 2 pages (with English translation).
Written Opinion in Vietnamese Patent Application No. 1-2017-04343, dated Apr. 26, 2018, 1 page.
Bruschke et al., "An experimental multivalent bovine virus diarrhea virus E2 subunit vaccine and two experimental conventionally inactivated vaccines induce partial fetal protection in sheep," Vaccine, Apr. 9, 1999; 17(15-16):1983-1991.
Cagatay et al., "Characterization of the humoral immune response induced after infection with Atypical Porcine Pestivirus (APPV)," Viruses, Oct. 2019, 11(10):880.
De Smit et al., "Prevention of transplacental transmission of moderate-virulent classical swine fever virus after single or double vaccination with an E2 subunit vaccine," Veterinary Quarterly, Jul. 1, 2000, 22(3):150-153.
Ukrainian Office Action in Ukrainian Application No. a2017 10277, dated May 21, 2018, 2 pages (English translation provided).
Xue et al., "Fetal protection against bovine viral diarrhea virus types 1 and 2 after the use of a modified-live virus vaccine," Canadian Journal of Veterinary Research, Oct. 2009, 73(4):292.

* cited by examiner

FIG. 3

Amino Acid Identity

Nucleotide Identity

| | Patterson | Sponheim | Madson | Ellingson | Arruda |
|---|---|---|---|---|---|
| Patterson | | 95.6% | 95.1% | 98.3% | 95.6% |
| Sponheim | 93.9% | | 98.3% | 97.1% | 98.6% |
| Madson | 83.7% | 89.2% | | 95.9% | 100% |
| Ellingson | 98.5% | 93.4% | 88.7% | | 97.5% |
| Arruda | 88.1% | 88.1% | 99.1% | 88.9 | |

PESTIVIRUS VACCINES FOR CONGENITAL TREMORS

RELATED APPLICATION

The present application is a continuation of U.S. application Ser. No. 15/253,511 filed Aug. 31, 2016, which claims the benefit of U.S. Application No. 62/212,124, filed on Aug. 31, 2015, both of which are incorporated herein by reference in their entirety.

BACKGROUND

A. Technical Field

The present invention relates to a pestivirus vaccine, which is capable of reducing clinical signs of congenital tremor (CT) or myoclonia congenita. The condition is informally known as shaking piglets, shaker piglets, or trembling piglets.

Pestivirus is a genus of viruses, in the family Flaviviridae. Viruses in the genus Pestivirus infect mammals, including members of the family Suidae (which includes various species of swine).

CT is a sporadic disease seen in newborn pigs. Usually more than one pig is affected in a litter. If the tremors are too great for the piglets to find a teat and suckle then mortality may be high. Mortality in an affected litter or in a herd outbreak could increase above the norm by 3-10%. The condition decreases as the affected piglets grow.

CT is classified into five types. Types AI, AIII, AIV and AV are related to exposure to classical swine fever virus, genetic traits, or exposure to trichlorfon. As these causes are known and therefore avoided, type AII, is hypothesized to be the most common cause. Type AII is thought to be associated with a viral infection. The causal virus in group 2, is widespread among most if not all pig populations, yet little disease is seen in most herds, presumably because an immunity is established in the sow herd. In new gilt herds however, there can be major outbreaks involving up to 80% of all litters during the first parity. This is an unquantifiable risk in any new gilt herd.

The reason that pigs are born trembling is secondary to the primary lesion of hypomyelination or demyelination of the brain and spinal cord. There is no specific treatment for this condition.

However, assisted suckling and provision of an environment where chilling and overlaying can be avoided will allow more pigs to recover with time, although weaning weights may be depressed by 1 kg or more.

B. Description of the Related Art

While there were early reports that porcine circovirus type 1 and type 2 infections (See, Burnborg et al., "Association of myocarditis with high viral load of porcine circovirus type 2 in several tissues in cases of fetal death and high mortality in piglets. A case study." *J Vet Diagn Invest.* 19(4):368-375, 2007), or astrovirus (See Blomstrom et al., "Astrovirus as a possible cause of congenital tremor type AII in piglets?" *Acta Vet Scand.* 56(1):82, 2014) were the cause of CT, this has since been disproved (See Ha et al., "Lack of evidence of porcine circovirus type 1 and type 2 infection in piglets with congenital tremors in Korea", *Vet Rec.* (2005) 156:383-384; Kennedy et al., "Absence of evidence of porcine circovirus infection in piglets with congenital tremors" *J Vet Diagn Invest.* 2003 March; 15(2):151-156). Thus, there is no clear pathogenic source of type AII CT in piglets and therefore, no effective treatment of this condition.

SUMMARY

The solution to the above technical problem is achieved by the description and the embodiments characterized in the claims. Thus, the invention in its different aspects is implemented according to the claims.

The present invention provides immunogenic compositions, vaccines, and related methods that overcome deficiencies in the art. The compositions and methods provide treatment for congenital tremors in piglets.

In one aspect, the present compositions can include an inactivated pestivirus comprising a nucleic acid sequence that has at least about 95% identity to SEQ ID NO:1, e.g., at least about 96%, 97%, 98%, or at least about 99%, e.g., 100% identity. In another aspect, the present disclosure provides compositions that include an inactivated pestivirus comprising an amino acid sequence that has at least about 95% identity to SEQ ID NO:2, e.g., at least about 96%, 97%, 98%, or at least about 99%, e.g., 100% identity.

In some embodiments of the present compositions, the pestivirus is a chemically inactivated pestivirus, e.g., a pestivirus inactivated by treatment with an inactivating agent such as binary ethyleneimine, ethyleneimine, acetylethyleneimine, beta-ethyleneimine, beta-propiolactone, glutaraldehyde, ozone, and/or formaldehyde.

In some embodiments, the pestivirus is a physically inactivated pestivirus, e.g., a pestivirus inactivated by treatment with UV radiation, X-ray radiation, gamma-radiation, freeze-thawing, and/or heating.

In another aspect, the compositions provided herein can include an attenuated pestivirus comprising a nucleic acid sequence that has at least about 95% identity to SEQ ID NO:1, e.g., at least about 96%, 97%, 98%, or at least about 99%, e.g., 100% identity. In another aspect, the compositions can include compositions that include an attenuated pestivirus comprising an amino acid sequence that has at least about 95% identity to SEQ ID NO:2, e.g., at least about 96%, 97%, 98%, or at least about 99%, e.g., 100% identity.

In some embodiments, a pestivirus described herein can be in freeze-dried form. In one embodiment, a composition has at least about $10^4$ virus particles, e.g., at least about $10^4$, $10^5$, $10^6$, $10^7$, $10^8$, $10^9$, or at least about $10^{10}$ virus particles.

In some embodiments, compositions disclosed herein can include a pharmaceutically acceptable carrier and/or excipient, e.g., an adjuvant, e.g., an oil-in-water emulsion-based adjuvant.

In some embodiments, a composition can include a mixture of inactivated and attenuated pestiviruses described herein. The present disclosure also features compositions that include a mixture of inactivated pestiviruses, attenuated pestiviruses, and vectors described herein.

In yet another aspect, the present disclosure provides compositions that include a vector, e.g., a baculovirus expression vector or a canine adenovirus vector, that comprises at least one nucleic acid sequence that has at least about 95% (e.g., at least about 96%, 97%, 98%, or 99%) identity to SEQ ID NO:3, 5, 7, 9, 11, 13, 15, 17, 19, or 21, e.g., at least one nucleic acid sequence that has 100% identity to SEQ ID NO:3, 5, 7, 9, 11, 13, 15, 17, 19, or 21. In another aspect, the present disclosure features compositions that include a vector comprising at least one sequence encoding an amino acid sequence that has at least about 95% (e.g., at least about 96%, 97%, 98%, or 99%) identity to SEQ ID NO:4, 6, 8, 10, 12, 14, 16, 18, 20, or 22, e.g., at least one sequence encoding an amino acid sequence that has 100% identity to SEQ ID NO:4, 6, 8, 10, 12, 14, 16, 18, 20, or 22. In some embodiments, the compositions may include a mixture of vectors described above.

Methods for protecting a piglet against a disease associated with pestivirus, e.g., congenital tremors, are also provided. The methods can include administering to a pregnant sow or gilt, or to a sow or gilt prior to breeding, or to a newborn piglet, any of the compositions described herein in an amount sufficient to protect the piglet.

In some embodiments, the methods include administering the composition to the sow or gilt intramuscularly, subcutaneously, intravenously, orally, intraarterially, intranasally (e.g., with or without inhalation), intracardially, intraspinally, intrathoracically, intraperitoneally, intraventricularly, sublingually, transdermally, and/or via inhalation. In one embodiment, the administering is a first administration, and the methods include a second administration one to three weeks after the first administration.

The present invention is related to inactivated or modified live pestivirus vaccines of the present invention are phylogenetically closest to the Chinese bat pestivirus. FIG. 1 and FIG. 2 identify the phylogenetic tree of the pestivirus of the present invention. The amino acid neighbor-joining tree is based on the 212 amino acids of NS3 which were overlapping between the partial and complete genome sequences among the pestiviruses. The level of diversity is consistent with a novel species of pestivirus. The pestiviruses at nucleotide level are between 83-98 percent conserved among the isolates identified, as shown in FIG. 3.

The pestiviruses of the present invention can be used for the manufacture of such vaccines. In particular, the invention provides improved pestivirus isolates that have been identified below, or any descendant or progeny of one of the aforementioned isolates.

The pestiviruses of the present invention can be characterized in that the virus can be attenuated by passaging at least four times in cell culture such that when the modified virus is administered to a swine or other mammal prone to CT it fails to cause clinical signs of CT disease but is capable of inducing an immune response that immunizes the mammal against pathogenic forms of the pestivirus.

Pestivirus isolates of the present invention can be passaged more than 10, preferably at least 20, still more preferably at least 30, even more preferably at least 40, still more preferably, at least 50, even more preferably at least 55, still more preferably at least 60, even more preferably at least 70, still more preferably, at least 80, even more preferably at least 90, still more preferably at least 95, and most preferably at least 100 times in vitro in cell culture.

It is contemplated that the vaccine may comprise a carrier that is suitable for intradermal or intramuscular application. In some embodiments, the vaccine is in freeze-dried form. In specific embodiments, the vaccine comprises at least about $10^4$ virus particles. The present invention provides immunogenic compositions, vaccines, and related methods that overcome deficiencies in the art. The present invention relates to immunogenic compositions which include an inactivated or modified live, attenuated pestivirus. Additional immunogenic compositions include a vaccine comprised of subgenomic antigen either recombinantly expressed or delivered as part of a vector platform. In particular, the application provides a vaccine for protecting swine and especially piglets against diseases associated with isolates of the pestivirus of the present invention.

Another aspect of the invention relates to a pestivirus comprising a nucleotide sequence that has at least about 95% identity, e.g., at least 96%, 97%, 98%, 99%, or 100% identity with a sequence set forth in SEQ ID NO:1, 3, 5, 7, 9, 11, 13, 15, 17, 19, or 21.

Another aspect of the invention relates to a pestivirus comprising an amino acid sequence that has at least about 95% identity, e.g., at least 96%, 97%, 98%, 99%, or 100% identity with a sequence set forth in SEQ ID NO:2, 4, 6, 8, 10, 12, 14, 16, 18, 20, or 22.

Another aspect of the invention relates to a method for the preparation of an inactivated or live attenuated vaccine for combating congenital tremors, comprising admixing an inactivated or live attenuated pestivirus described herein with a pharmaceutically acceptable carrier.

Immunogenic compositions and vaccines of the invention comprise inactivated or modified live pestiviruses and may also include an adjuvant. The vaccine may also include other components, such as preservative(s), stabilizer(s) and antigens against other swine pathogens.

Those of skill in the art will understand that the compositions used herein may incorporate known injectable, physiologically acceptable sterile solutions. For preparing a ready-to-use solution for parenteral injection or infusion, aqueous isotonic solutions, e.g., saline or plasma protein solutions, are readily available. In addition, the immunogenic and vaccine compositions of the present invention can include pharmaceutical- or veterinary-acceptable carriers, diluents, isotonic agents, stabilizers, or adjuvants.

Methods of the invention may also comprise admixing a composition of the invention with a veterinarily acceptable carrier, adjuvant, or combination thereof. Those of skill in the art will recognize that the choice of carrier, adjuvant, or combination will be determined by the delivery route, personal preference, and animal species among others.

Another aspect of the invention contemplates a vaccine for the protection of swine against pestivirus infection, comprising an inactivated or live attenuated pestivirus of the present invention and a pharmaceutically acceptable carrier.

Such a vaccine may advantageously further comprise one or more non-pestivirus or pestiviruses that differ from the pestivirus of the present invention, attenuated or inactivated pathogens or antigenic material thereof. For example, the non-pestivirus pathogens may be selected from Pseudorabies virus, Porcine influenza virus, Porcine parvovirus, Transmissible gastroenteritis virus, *Escherichia coli, Erysipelothrix rhusiopathiae, Bordetella bronchiseptica, Salmonella choleraesuis, Haemophilus parasuis, Pasteurella multocida, Streptococcus suis, Mycoplasma hyopneumoniae* Porcine Circovirus, including but not limited to Porcine Circovirus Type 2 (PCV2), Porcine Reproductive and Respiratory Syndrome (PRRS), and *Actinobacillus pleuropneumonias*.

Methods for the treatment or prophylaxis of infections caused by a pestivirus are also disclosed. The method comprises administering an effective amount of the immunogenic composition of the present invention to an animal, specifically a pregnant sow or gilt, wherein said treatment or prophylaxis is thereby provided to the piglets. The treatment or prophylaxis is selected from the group consisting of reducing signs of CT infection, reducing the severity of or incidence of clinical signs of CT infection, reducing the mortality of animals from CT infection, and combinations thereof.

Herein, suitable subjects and subjects in need to which compositions of the invention may be administered include animals in need of either prophylactic or treatment for a viral, microbial, parasitic, protozoan, bacterial, or fungal associated infection, disease, or condition. Animals in which the immune response is stimulated by use of compositions or methods of the invention include livestock, such as swine, bovines, goats, and sheep. Preferred animals include porcines, murids, equids, lagomorphs, and bovids. Most preferably, an immune response is stimulated in swine and especially sows, gilts, and piglets.

The invention provides a method of reducing the incidence of or severity of one or more clinical signs associated with or caused by a pestivirus infection, comprising the step of administering an immunogenic composition of the invention as provided herein, such that the incidence of or the severity of a clinical sign of the pestivirus infection is reduced by at least 10%, preferably at least 20%, even more preferred at least 30%, even more preferred at least 50%, even more preferred at least 70%, most preferred at least 100% relative to a subject that has not received the immunogenic composition as provided herewith. Such clinical signs include whole body trembling and shaking to a variable extent. Piglets are usually born shaking, trembling and nodding, and active stimulation will often exaggerate the shaking. The shaking tends to stop when the piglets fall asleep. In addition, there may be muscle tremors when piglets are walking around, nervous symptoms, lack of coordination, "dog sitting" and increased mortality. In some cases, the trembling may not become apparent until 24-48 hours of age. The effect on the piglet includes affecting suckling, where in severe cases, physical holding of the piglet onto the teat is required. Depending upon the severity of the outbreak, mortality levels can be 15-20% and up to 30-40% in more severe outbreaks. Other measures of clinical severity include reduction in average daily weight gain and neurological damage.

Preferred routes of administration include intranasal, oral, intradermal, and intramuscular. Administration intramuscularly or intravaginally, most preferably in a single dose, is preferred.

Skilled practitioners will recognize that compositions of the invention may also be administered in multiple (e.g., two or more) doses, as well as by other or multiple routes of administration. For example, such other routes include subcutaneously, intracutaneously, intravenously, intravascularly, intraarterially, intraperitnoeally, intrathecally, intratracheally, intracutaneously, intracardially, intralobally, intramedullarly, or intrapulmonarily. Depending on the desired duration and effectiveness of the treatment, the compositions according to the invention may be administered once or several times, also intermittently, for instance on a daily basis for several days, weeks or months and in different dosages.

Also contemplated is a method for the preparation of the live attenuated pestiviruses to non-mammalian cells.

The new vaccines of this invention are not restricted to any particular type or method of preparation. These vaccines are prepared by standard methods known in the art. The most preferred delivery of the pestivirus vaccine is to inoculate gilts or pregnant sows against the virulent pestivirus, with maternal immunity transferring to the piglets.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3 is a comparison of the amino acid identity (percent identity) of the pestivirus sequences of the invention.

DETAILED DESCRIPTION

Figure 1:
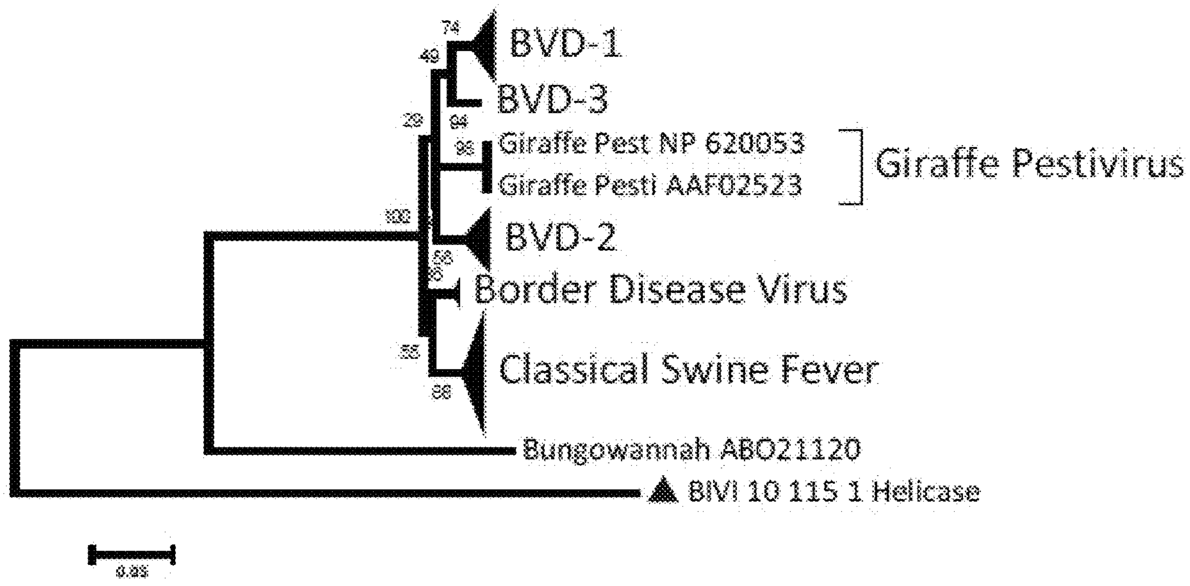
FIGS. 1 and 2 illustrate the phylogenetic trees identifying the novel pestiviruses of the invention.
Figure 2:
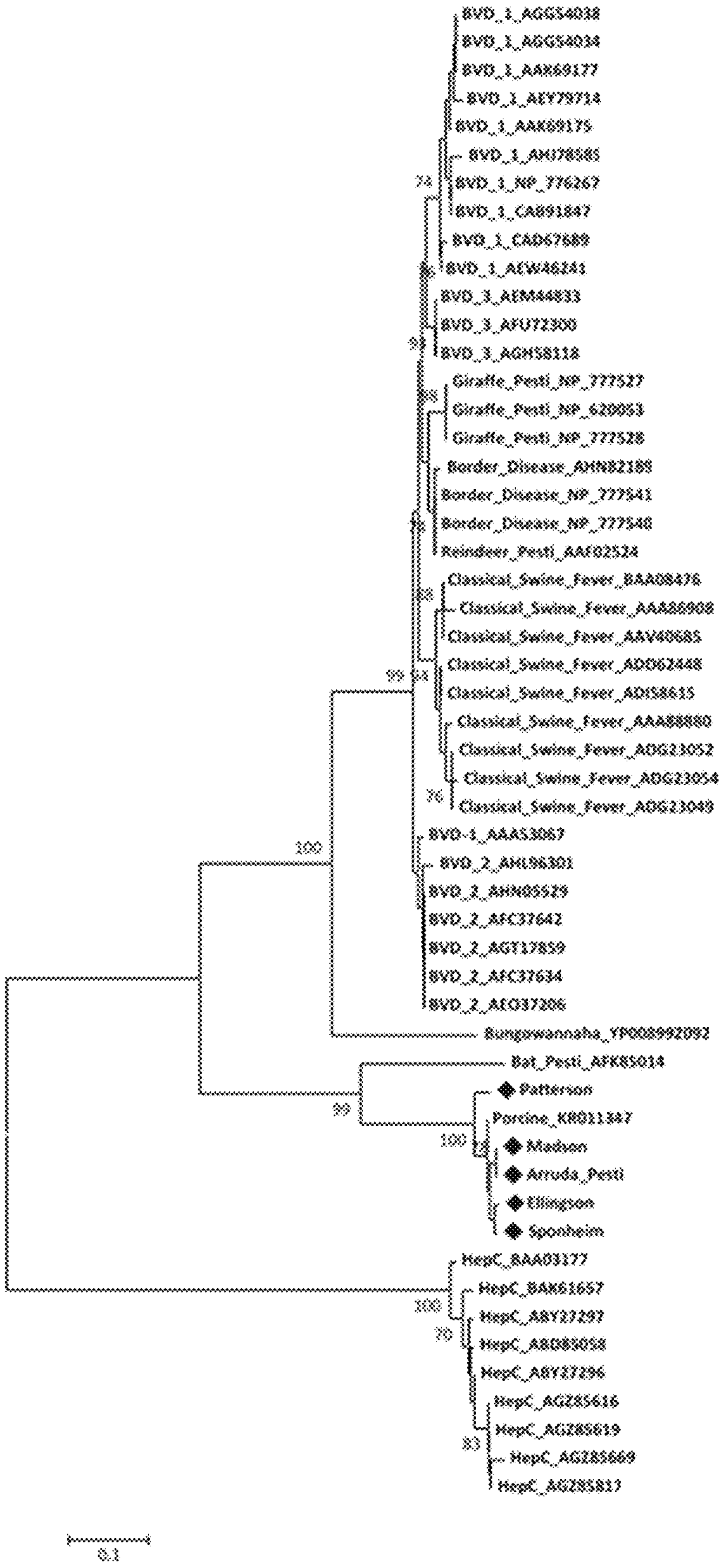

The invention provides an inactivated pestivirus, attenuated pestivirus, and subunit vaccines or immunogenic compositions that can be administered to sows or gilts to reduce the clinical effects of congenital tremors in their piglets. In addition, there are methods of administration, methods of making the vaccine, assays, and other aspects of this invention described.

Preferably, the pestivirus according to the invention is an inactivated pestivirus and/or a modified-live pestivirus and/or an attenuated pestivirus having a nucleic acid sequence that has at least about 95% identity to SEQ ID NO:1, e.g., at least about 96%, 97%, 98%, 99%, or 100% identity to SEQ ID NO:1, or having an amino acid sequence that has at least 95% identity to SEQ ID NO:2, e.g., at least about 96%, 97%, 98%, 99%, or 100% identity to SEQ ID NO:2.

(SEQ ID NO: 1)

CATAATGCTTTAATTGGCCGCATTATGTGTGGGACATCCTAAATATTTATGAGCCCTGCGGTGAGTGGGGGAAAGAG

GTTAACCAGGCCTCTAGTACCACAGGCACCAATGGACAGGGCAACTCAAACCTGAGAGAGAGGTACCGAACTCTTAA

GCCCCGAGTACGGGGCAGACGTCACCGAGTAGTACACCCAAAGACCACCACTTCTAGGTGTAGGGTCTACTGAGGCT

CGGGTGGACGTGGGCGCGCCCAAAGAGAAATCGGTGGTGGACCTGGGGGTCGGGGCCACCATGCCCCTTTACGGGGT

-continued

AGACCTTACTGCTTGATAGAGTGCCGGCGGATGCCTCAGGTAAGAGTATAAAATCCGTTGTTCATTAACATGGAAAA

ACAGATTGCATATTACTTAAAAAAAGAAAAACAAAGAAATGGGTGGACGGAACTGGTGGTAGGAGAAAGTCATACAA

AAATAACCACGCTTTCTGGAAAGACCTATCGAGGCACCTGGGAAATGGAGAAACGGCCAAATCCTTATGGAACCTAT

CTCCCCAGACCTAGTCCCCAACAGCTTACAGCCCTACACCCCCACCCAGTGGTGAATTGTAAGGTGGTTGAGTACAA

GGAGATGGACCCTAATTATGGTGATTGCCCAAATACGAACGGGGTGTTTGTTGACGAAAAGGGTAGAAGGCTGAGCA

GCCCTCCATTAGGCATTTGGAAGATAAGATTGGACTATAGTGACTTGGTAAACATAAGCAGACCAACCCCCGCTAGT

GGGAAAAACTCTTACCAAGTTGAGACCTGCAGTGGGGAGCTGGCTACAGTGACACTGGTACACAATAGGGTGCTCGT

GGAAGATTGCAGGGGGCTATACCAATGGAAACCCAACTGTGAAGGAATTGTGCTCTATGTGAAAACTTGTTCTGACT

GGGCAGATCAGGTAGAAAAACAGGAGAAAGAAAGCCCCCCAAAACCACAGCGGCCACCAAGGCGAGACCCACGAAAA

GGGTTACAACCACAAGTCCCCAAAGAGACTGAGGTCACAGAAAAGAAGAGACAACCTAGTGTCACCTTAGTATCGGG

GGGGCAGAAGGCCCAAGTCATCTACAAAGGCAGGACCAAAAACAAAAAGACCCCGGATGGAGTCTATAGATACCCAG

GAGCTAAAGAAGGGGACGTAGTAAAGGTCAGGAAGATGCTGAAGAATTGGCATATAGCCTTAGTGATGTACCTGATA

CATATCATAACTCCAGGCCTTGCCAAGGTCCAGTGGTTCTTAAAAGATGAAAACTCGACGGGGATCAACCAGATACT

GTGGCAAAGACAGATCAACAGATCCTTACATGGAGAATGGCCTAACCAGATCTGCCACGGTATGCCCAATGAAACTA

TCACGGATGAGGAATTACGCAGTCTGGGAATGGTAGATACAAGCCCTAGAACAAACTACACCTGTTGCCAGTTGCAA

TATCATGAGTGGAAGAAACATGGTTGGTGCAACTATCCACAAAAACAGGCGTGGATCACGAGGATAACGGCCCTACA

AGCTAACCTTACCGGGCCTTATGAGGGACCTGAGTGCGCCGTCATCTGCCGATTTAACGGCAGCTACAACATCGTAA

AACAGGCCAGAGATGAGGTGAGTCCACTGACAGGGTGCAAGGAAGGGCATCCTTTTCTATTCTCTGGTGAAAGATCC

GACACCTCATGCCTAAGGCCCCCTTCCACTAGTTGGGTAAGACCAGTGAAAATGGACGAGGCATCAATGGCCGATGG

CTTTGCCCATGGGGTTGATAAGGCGATAATACTAATCAGGAAGGGGGCATCAGGAATAATCAATTTCCTAGACACTA

TTGGGAGGTGGCTACCGGTAGCTGAAGCAACTATAGTACCATATTGTGATACTTACACTGTGACAGGGATGTATGTC

CATGTAAAGAATTGCCTCCCTAGAGGGTTACCTAAGCATTCAAAAATAATCTCCCCGACAATGATATATCTGGGAGA

AGGAGACCCGGCCCATAATATCCAGCACTTATTTGGCTCAGGTATAGCAAAGTGGGTCCTAGTTCTACTCGGGATTC

TGGGTGAGTGGTATGGAGAATTGGCTTCCACAATATACTTACTACTAGAATACGGGTCTGAGTGGTTGGAACATGAA

AGCCTGGTCACGGAAGGGTTGATTCCTGGCATTAATATTACAATAGAACTCCCAGCTAGTCATACAGTGCCTGGTTG

GGTGTGGGTCGCAGGCCAGTGGGTATGCGTGAAGCCAGACTGGTGGCCTACACAGATTTGGATTGAAACCGTGGTGG

CAGAGACCTGGCATATACTAAAAATATTGGCGTCAGCCCTGGTGAACATAGTTGCAGCGTTCGTAAACCTGGAATTG

GTTTATCTGGTCATAATACTAGTCAAAATATCAAAAGGGAACCTGATAGGTGCCATATTATGGTGCTTGTTACTGTC

AGGCGCTGAAGGCTCGTGCTACAAAAGACAAGACTATTACAACACCCAACTAGTCGTCGAAGAAAAAACAGGCGTAG

AAAAACGATCTATAATGGGCAAGTGGACCGTGATAACCAGGGAAGGTCGGGAGCCAAGATTAATGGAGCAAATAAAT

ATGGTATTGAATGATAGCCTGTCAGAAACCTACTGCTATAATAGGCTAAACACCAGCACTTGGGGGCGGCAACCGGC

AAGACAAAGAGGGTGTGGTCAAACCGTGCCCTATTGGCCTGGTGACAATGTTCTAGAAGAACAATACTACAGCACAG

GTTACTGGGTGAATGTAACAGGCGGTTGCCAGCTGAGAGAAGGCGTATGGCTATCAAGAAAGGGTAACGTACAGTGT

CAGCGTAACGGCTCATCCTTGATGCTGCAATTGGCGATAAAAGAAGAGAATGACACTATGGAAATACCATGTGACCC

AGTGGAAACTGAAAGTATGGGTCCAGTTGCACAGGGCACTTGTGTGTACAGCTGGGCATTCGCCCCAAGAGGGTGGT

ACTATAACAGGAAGGATGGTTATTGGCTCCAGTACATAAAGAAAAACGACTACCAGTATTGGACAAAAATGCCTACT

GCCTCGTCCGCCGCAACCATGTACCGCCACTTGCTCCCCTTACTGGTGGCCTGCCTCATGGGCGGTAGGATATCGGT

GTGGTTTGTGGCAATGCTCCTGTCTCTACAGGTGGAAGCTAGTGAAGTAGGCACTAAACAACTGGCTGTCACGCTAA

CCCTGTGGAAAATGGACTGGACAGAACTACTTTTCTATATTGTCTTGATGCTAGCCGTTAAGGAAGAACTTATAAAA

AAAATTGTGACCGCTAGCCTTGTGGCCTTAAAAAATAGTCCAGTAGCCTTGAGTTTTCTTATTGTACTCAGACTTGT

GGGGGGCAGTGAAGCACTCCCAGTAGGTTTATTATTAGAAAAAATGTGCATAGACCAACCGGAGTTTGGAACTCCTT

-continued

TCCTGATCTACCTATGGGACAACTGGAAGTGGACTGTGTTAGTCAGCTTCTCCGCACTGAACCATGAAAAAACTATA

AAACTGGCAAGAAAACTGTTGTTGGCAACACATATAACAGCGCTCACATTGACTGGCTTGAGTGATTCAATCTTCTA

TATGATGCTTATAACAACAAATTTGTTAATAAAGACATTCATATACTTGCTGGGGGCTAGTATGAATTGGGTCGAGA

GAGAAAAAAAGAAATTGCTAGTGAAGAGGAGACTAATATACAAGAAAGCCGTTACTTGCAGTCAGGATGAGAATGTA

TTGGAGAATAAATTCAACAAGATAACTGTAAACGCGGATTTCACCCCATGCAAGCTTGAACTTCTACAATTACTTAG

GGCTTTTTTAGTCTCTTTGTGTTTTTCCTACTACAAACCTCTCCTGTATGCAGAGACTACCTTAACTGTAATAGTAA

TTGGCGTACAAGAGTACAACGTAGCCATGGCCCGCGGGCGAAGTGTGGTCCACAGGCTACTAGCCATGGCCTATTAC

ATATACGGCCGCATACAGGGTGACATGTTCCAGCTCGCCACTATCCAGTGCCTGCTGTCGAGTCCGAGGAAAATTAT

GAAACACATGGTAGAGAATCCAACTCTCAAGAAGCTCTGGCAAGGCGAAACAGAACTCTTCAACCAGGGTGTTAGTC

AATCCAAGATAGTGAATCCAAAGAAAATTGGGCTGGAAGAATTACACAAGGGCATGTGTGGCCTCCCAACAGTAGTG

CAAAATTTGGTCATATATGCAAAGAAGAATGACTCTCTTATTTTAGGAGAGCTGGGTTACCCCCCTGGGGATCTCAC

CAGTGATGGGTGGGAAATTTTAGGTCCTGGCAGAATCCCAAAGATCACTAACGTCGAGTCTGCTAAGATGGACTTAC

TCTCCAAACTTATGACCTTTCTGGGGATTGAAAGCTCGAGGGTCCCCAGGACCCCAGTCCACTCAACAAGGAAATTA

TTGAAGATAGTAAGGGGCTTGGAAACAGGATGGGGGTACACTCACGCAGGGGGGATAAGTAGCGCAAAACACGTTAC

AGGTGAAAAGAACTTAATGACCCACATGGAGGGTAGGAAGGGAAAATATATCCTACAATCTCAAGAACATGGTGCTG

ACGAGGTAGAGTACGGAGTAAAAACTGATCAAAAAGCTCCCGACAATGCCTTATGCTACTGTTTTAACCCTGAAGCT

ACAAACATAAAAGGAGAGACGGGAGCCATGGTGTTCATGAAGAAGATAGGAAAAAAGTGGACTCTCGTAACATCAGA

CGGCAATAAAGCCTATTATAATGTAAACAATTTGAAAGGGTGGTCTGGACTACCAATAATGCTGCACTCCACCGGGG

CCATAGTGGGGAGGATTAAATCAGCGTATTCAGATGAAAACGACCTGGTGGAGGAACTTATTGACTCTAGAACTATT

AGTAAGAGCAATGAGACAAACCTGGACCACCTTATCAAGGAATTGGCAGACATGCGGAGGGGGGAGTTCCGCTCAAT

TACCCTTGGAACGGGAGCCGGGAAAACCACAGAACTGCCTAGGCAATACCTCACAACAGTAGGTGCCCATAAATCCG

TGCTGGTCTTAGTCCCCTTAAAAGCACCTGCTGAAAGTGTTTGCCGCTTTATGAGGTCTAAATACCCTACCATCAAC

TTTTCCTTAAGAGTGGGGGAACGGAAAGAGGGAGATGTGAGCAGCGGCATCACCTACGCTACTTACGGATTTTGCTG

CCAGCTAAACCTAGTCCAACTTAAAGAATGGATATCCAGGTACTCAATGGTTTTTTTGATGAATATCACACAGCAA

CTCCAGAACAAATAGCCATAATAAGCAAGATTCATGCACTGAAAGTTAAGACCAGGATAGTGGCTATGTCAGCAACC

CCCCCGGGTACCGTGACGACTGAAGGCAGGAAGTTTGACATTGAAGAGGTAGGGGTTGCTACCATAGAGAAAGGAGA

GGAACCAAAAAGGGGGCGCATAGCGGTCGCTGGTATGCAGGTCCCATTAGAAGACTTAACAGGAAAGAACTGCCTGG

TGTTCGTGGCAACCAAAGAAGCCGCGGAGACGGAGGCTAAAGAACTGCGCACCAGAGGAATTAACGCCACCTACTAC

TATTCAGGTATAGACCCTAAGACTCTGGAACATGGGATGACCAATCAGCCATACTGTATTGTAGCTACCAATGCCAT

TGAATCAGGTATAACCTGTCCTGACTTGGATGTGGTCATAGACACCATGCAGAAGTACGAAAAAGTAGTGAATTTCT

CGGCAAAGATGCCCTTGATTGTCACTTCATTAGTAAAGAAAAAAATCACCAGGGAAGAACAGGGCCAGAGGAAAGGT

CGAGTGGGCAGGCAAAAGAAAGGAAAATACTACTACCCCTCGGGGGTGGTACCGAATGGGTCAAAAGACCTAAGCTA

TTTAATCCTACAGGCCCAAGAATATGGTGTCTTGGAACAAGTCAATATAACAGAGTACTTCATCATAATGAATGAGG

ACTGGGGTCTCTATGACGTAGATGAAGTAGAAGTGAGAATACTTGAGAGAATGAACAAGGAAATCTTGCTACCACTA

GGTATTGTGGAGAAGCAAATCTTGGAAAGAAGTACTCACCCGGAAAAAGTGGCACTGTTGTATAACAAATTAGTGCA

GAAAAATCCTATAGTATACCCTAGAGTACAGGAAGGTGAGGTCAGCAAGGAATACAATACCTATAATCTGGCCGTAT

ATGACAAGCTAAAAGATGTCAACCCACAAGCCATTTATGTTCTAGCAGAAGAGGAGAGAGCCACAGAAATGATGGGT

CTCGAGTTTGAACAAGACCCATCTGACTTACAGGATTCGGTAGTTCAGCTTTGTGAAGATATCAAGAGGTATACAAA

ACTCTCTGGGATCACTGAGAAACTGCTAGTAGGTACGATGGTGGGGTATATTGGATACAAAGCCTTAACCAGAAACC

ACGTGCCCTGGGTCAGCAAAGAGTATTGTTATGAGCTGACCGATTCACCGGATACTTACGAAAACTCATTCGCACCT

-continued

TTGGACGTCGACGTCCAAAACTCCGGTGAAGGAAAACACCCAGAGCAACTGGCAGACCATCAATTGAGGCAACTACT

GGAGACTGGGAGAGACAAGGCAATTGATTTCCTAAAAGGAATCCGCGAGTTCACTAGTGGGGCCATAAACAGTCCAA

AGGCACTAAGTATATGGGAGAAAATATATCAGTATTTGAAGAAGCATCAGGGCGAGATCATCTCATCAGCAGCGTGG

GGCAGTGCGACGGCCCTTCACGACAGTATTAAATCTAGACTAGGAGATGAGGTCGCTACTGCAGTAATAATCCTCAA

GTATTTAGCATTTGGTGAAAGAGAACTGTCTGGGCTAACTAGGCAAGTTCTAATTGACATCATAGTATATTATATAG

TTAACAAGCCCCGGTTCGAAGGAGACGACTACGCAAAGAGAAAAGGAAGAAGGCTAGTCATCGAAGTCCTGATGGGG

GCACTGGCGACTTATGCGGTGTCCAATTTTTGGGGTGTGTCCATTAATAAGATACTGCAACCAATTTCTGATTATCT

ACCCTATGCCACCGCCACTTTGGCTTTTCTTCGCCCAACCTTCATGGAATCAGCAGTGGTGGTCGCTTCCTCTATCT

ATAGAGCTTTTCTCTCCATTAAGCATGCGGAAAACAGGAGTCTTGTCACGCAGGTCGCTTCTGCCGCCCTCGAAGTC

ATGGGCCTGACCCCAGTATCGGCTGGCCTAGGCGTCTTGCTGGGGCTTGGGTTGTGTGTGCTCCATATGAACATTGA

CAAGAATGAGGAGAAAAGGACACTTATACTGAAAATGTTTGTCAAAAACTTTATAGACCAGGCGGCACTAGACGAGT

TGGATAAACTGGAGCCAGAAAAAATAATCCTCTCATTGTTGGAGGGTATCCAAACCTGCACAAACCCGATTAGAGCA

ATCATGATTTTGTACAGGGTGTACTACAAGGGAGAAACTTTCACAGAAGCTTTGTCTAAGATGGCCGGCAAGTCTCT

CATTGTGATGGTCATAGTCGAGTTCCTGGAATTGACAGGCCAAACCCAAGGAGGGTATATAGATCTTAGTGCTAATT

TGCTGACCTTTCTCCTCGAGAAACTAAAAAAAATGACTAACCTCGCCATCGGGGAAGCTAGAAAGGTCTTGCTCCCC

ATCCCATACTTGTACTGTGAAACCTGGCAGTCTGACGCCAGAATCAAGGCCCCTGAATCCTACGACCAAGTGGTAGT

GGAATGCAAATGTGGCGCTTCAGCGAGGTATTCCTTCCGCGATGGAGTTCATGAGATATTGGAAGAAAAAAGGACTA

ATTGGTGCAAGAACTTCTTCTTATGGGGACCCAACTTCCACAATCCGGATCCAAAAAGGATGACATTCTATGAATAC

GGCCAAGCAAAAAAGTGTCCTGTTATCATAATTGGTGAAGACATAACCTTCGGCAAATATGGCATATATATCAAATT

TGGCCATAGGCCTGATGGAGGGAGGTTAATAAGGGGTACCACCCACGCTACTATCAGTAGGGAGGAATTGCTGGAAA

TCCTAACAGCCCCAAGCCAAGTGGCCATAGGCAAGGTCAAGCTAACCGATTACTGTAATCAAAAAGGAATAATAGAC

AGGAAATTGGCCGTACTTGAAGGTGACAAAATACATTTTTGGAAAGCACACCGTGGATCCAAAATCACAGACCAACT

CACTATTGAGAATCTGACAGATGATTTGGGGTCAGAAATCAGGGACATCACATGGGAGCTGTACACAGGTGGAACGT

GCACCGTAAAAGGGGTGTCCCTTAGATCATGCGCACCAGGTCATAGAACTAAGGCTATGGTCTTGTGTGATTGCACT

GATGTGCTTAGCCCCTGTTACCTAATAAACGGCAGGAGACCATCCCCATTTGACGTCGCGGAAGGTTATGAATGTCA

CCACCGGAAGCCCCGAGCGACGTATGAAGACCTAGAAATGGAGGAAATACTAAAGAGACGAGTCCCTGTCTACGATC

CTCTGTGTTTGTTTGACACTGATAGTAAACTGCTACCTCCCGACACCTACTACTTGGAAGAAGATCAAGAGGACTTT

GAGTACGCATTGAGATGCTGGGGCCTCGGGGTTTATGTAGCAGACGGGCCTGTCACTTCCCCCCCGGACATAAGAAT

ACACCATAGTTCGGTATTACTACTGCTGACACCTGGAGTAAACTCAGAGTTGCCCTTACAGTACATACGTTGTTACC

CTCATCAGGCAGAGGTGGACATCTACATTAGGAGTCAGCTTTTGGAGGAGGAAGACACTGCTACGGAGGTGGAAGGC

TCCCAGGAAGATGGTGATGAAGGGATGGGCGATGCGGTAATAGAGGATGAGGATACATCGTCCACAACAGAATCAAT

ACCCCCACTAGAAGAGGAGGAAGGGGGCGAAGAGCCAATCACCTATGTGGTCATAAGGGGATTACAAGAAGAAAGAT

ACGCCAGCCATCTTAAACTAAATGACTGGATCAGTGAAAACATTTCAGAGCCACACAGAGTCCAAATTATGCTAGAT

GGGACAGTGAGAGTCACAATAAAAGAGGGCAAAGTGAAACATTTGTTTGGGGTCTATAGAATAGAAAACTCCCTGGA

AGCAATGTTTAAAGAGACCATAGCTGACCTCCCCGTAGCTACCCAACCGCCCCAGGGGCCAGTCTATACGGCTAAAG

AGCTGGCCCAAGGGAACATCGCCCCGGTCCAACCTGCAGCGAATTATTACGGAATGATAGAGGGGAGAGGCGACCCA

ATGACGGCATTCGAAGCCTTATCAGTCTTGCGGTCACAAAAAGTCTTAGCCAAGGACGTGAAGGTGAACACCCGCAG

GGCGCAGGTTTTTTTAAATAAAGTCAGGAGAATTGCTGAGGTCAGAGCGTCGGAACTGACATTAAAATGCTTACCGA

TACTTGGCAAAGTAAATGGGAGGAAATTGATTAGAGAGGAAACCAACATCCCCAACCAAAGGTTGGCATCAATAATG

ACCTCAATAGGAATTAGACTAGAAAAACTGCCAGTGGTTAGAGCAAACACTTCCGGCTCTAAGTTCAGACAGTCAAT

CTTAGAAAAAATGGATAAGTATGAAAATGAACAAGTCCCAGGGTTACATGAAAAGATGTGGGCAGCGTTCCTGGCAA

-continued

CTGCCAGGCAAGATTTAAGAAATACCTATGAGGAAGTAACTTATCTTGAATTAGAGGCCGGAATCAATCGGAAAGGA

GCCCCAGGTTTCTTTGAAAAAGAAAGCTCAATAGGAGAAGTGCTGGAAAAAAAAGAAAAAATTGACGTCACAATCCA

AGAGATTGAAAAAGGCAACCACTTATACTATGAAACAGCCATGCCAAAAAATGAGAAAAGAGATGTGCTTGATGATT

GGTTGTCAGAGGATTTCGTCACTTATAAGAAACCACGTGTGATACAGTACCCTGAGGCAGTCACCCGGTTGGCCATC

ACCAAAATAATGTATAAGTGGGTGAAGCAAAAGCCTATAGTGATTCCCGGTTATGAGGGAAAAACCCCGATCTTTGA

AATATTTGAAAAAGTCAGTGCAGATTGGGCTCAGTTCAAAAATCCGGTAGCCGTCAGCTTCGACACCAGAGCCTGGG

ACACTCAAGTAACAAGAGAAGACCTCAGGCTGGTAGGGCGGATACAGAAATACTATTACAAAAAAAAATATTGGAAG

TTCATTGACAATTTGACAGCCATGATGGAGGAAGTGCCTGTAATCACTGTAGAAGGAGATATGTTCCTCAGAGTTGG

ACAGCGCGGATCCGGACAGCCTGATACCTCAGCAGGCAATTCCATGCTAAATGTGCTGACTATGTTGGTAGCTTTCT

CTGAATCCACAAATCTGCCCATAGCGGCTGCCTGGAAGGCCTGTCGGATCCACGTCTGTGGTGACGACGGTTTCTTA

ATCACAGAATCGGAATTAGGGAGGAAGTTTGCTGAAAAAGGTGTTCCTCTGTTAGCTGCATTTGGCAAACCCCAAAA

AATTACAGAGGGAGCGAGCCTAAAGGTAACCAGCAACTTTGACGGAATAGAGTTTTGTAGTCATACCCCTATCAGAG

TCCAAACACCAAACATCAGGTGGATGCCAGCGAGACCAACAGCAACAATCCTAGGCAAAATGAGTACCAGGCTGGGT

GAGGGTGCCACCAGGTCGGGAGAAGAATACGAAAAACAGGTGGCATTCGCATATCTACTGATGTACCCCTGGAACCC

GCTGGTCAGGAGAATCAGCCTCCTATTGTTATCGACTACTGACCCAATGGGGAAAGAGGAAACCCCATGCTCCGATG

AGGGGGTGAAGTATGTTGGGGACCCTATCGCTGCATACAGGGATGTATGGGGGCACAAATTAGAGGATGTAGGCCAT

GTTGATCAACCGCAGTTATCCCGGATGAACTATAGCATGACTTACTTAGGGATTTGGAAACCAAAGACAAGTCAGCG

GCTAGTCGAACAGTGTTGTCGTCTGGCCGAGAAAAGCAATTGTGTGGTACGTGCTGACTCCCTGATAAAGAAAAAGG

TCAAGATCACTTATGACCCGGGGATAGGAGTGGCTCAGGTCATTCGTAGGTGGGAAGAGCTTGAGTGGACCAGAAGG

AAACCTGAACTCACCAATGTAATTGTAGAAGATGATATCTTCCTAGTCCTGTGGAAGAGATTTTCAAAGTACATTTT

TCAGAAAATGAAGTTCATGCAGAGAATGTTCGCCCCTTATTAAGTGGGGGGCACTCATTTAAATTATAACCAGTATC

TGGTAAGTATAAGATTTGTGTAAATAAAGTATATAACTGAAAGGGGCAAGTGGCCGTATAGGCTGGGGTGATCGCCG

CACCCCCCCCTTCACTAGGCGCCTCAACCCCATGTACCATGGGGTTGTTGTAAATACTTGAATGAATGGAGTAATAC

GGGTAACAAACTTATAGGCCAGTATTGCCCCATTTGCTTTATAGTGGTGACGACCTGTATAGGTCCGATCTGATATC (SEQ ID NO: 2)

MEKQIAYYLKKEKQRNGWTELVVGESHTKITTLSGKTYRGTWEMEKRPNPYGTYLPRPSPQQLTALHPHPVVNCKVV

EYKEMDPNYGDCPNTNGVFVDEKGRRLSSPPLGIWKIRLDYSDLVNISRPTPASGKNSYQVETCSGELATVTLVHNR

VLVEDCRGLYQWKPNCEGIVLYVKTCSDWADQVEKQEKESPPKPQRPPRRDPRKGLQPQVPKETEVTEKKRQPSVTL

VSGGQKAQVIYKGRTKNKKTPDGVYRYPGAKEGDVVKVRKMLKNWHIALVMYLIHIITPGLAKVQWFLKDENSTGIN

QILWQRQINRSLHGEWPNQICHGMPNETITDEELRSLGMVDTSPRTNYTCCQLQYHEWKKHGWCNYPQKQAWITRIT

ALQANLTGPYEGPECAVICRFNGSYNIVKQARDEVSPLTGCKEGHPFLFSGERSDTSCLRPPSTSWVRPVKMDEASM

ADGFAHGVDKAIILIRKGASGIINFLDTIGRWLPVAEATIVPYCDTYTVTGMYVHVKNCLPRGLPKHSKIISPTMIY

LGEGDPAHNIQHLFGSGIAKWVLVLLGILGEWYGELASTIYLLLEYGSEWLEHESLVTEGLIPGINITIELPASHTV

PGWVWVAGQWVCVKPDWWPTQIWIETVVAETWHILKILASALVNIVAAFVNLELVYLVIILVKISKGNLIGAILWCL

LLSGAEGSCYKRQDYYNTQLVVEEKTGVEKRSIMGKWTVITREGREPRLMEQINMVLNDSLSETYCYNRLNTSTWGR

QPARQRGCGQTVPYWPGDNVLEEQYYSTGYWVNVTGGCQLREGVWLSRKGNVQCQRNGSSLMLQLAIKEENDTMEIP

CDPVETESMGPVAQGTCVYSWAFAPRGWYYNRKDGYWLQYIKKNDYQYWTKMPTASSAATMYRHLLPLLVACLMGGR

ISVWFVAMLLSLQVEASEVGTKQLAVTLTLWKMDWTELLFYIVLMLAVKEELIKKIVTASLVALKNSPVALSFLIVL

RLVGGSEALPVGLLLEKMCIDQPEFGTPFLIYLWDNWKWTVLVSFSALNHEKTIKLARKLLLATHITALILTGLSDS

IFYMMLITTNLLIKTFIYLLGASMNWVEREKKKLLVKRRLIYKKAVICSQDENVLENKFNKITVNADFTPCKLELLQ

LLRAFLVSLCFSYYKPLLYAETTLTVIVIGVQEYNVAMARGRSVVHRLLAMAYYIYGRIQGDMFQLATIQCLLSSPR

-continued

KIMKHMVENPTLKKLWQGETELFNQGVSQSKIVNPKKIGLEELHKGMCGLPTVVQNLVIYAKKNDSLILGELGYPPG

DLTSDGWEILGPGRIPKITNVESAKMDLLSKLMTFLGIESSRVPRTPVHSTRKLLKIVRGLETGWGYTHAGGISSAK

HVTGEKNLMTHMEGRKGKYILQSQEHGADEVEYGVKTDQKAPDNALCYCFNPEATNIKGETGAMVFMKKIGKKWTLV

TSDGNKAYYNVNNLKGWSGLPIMLHSTGAIVGRIKSAYSDENDLVEELIDSRTISKSNETNLDHLIKELADMRRGEF

RSITLGTGAGKTTELPRQYLTTVGAHKSVLVLVPLKAPAESVCRFMRSKYPTINFSLRVGERKEGDVSSGITYATYG

FCCQLNLVQLKEWISRYSMVFFDEYHTATPEQIAIISKIHALKVKTRIVAMSATPPGTVTTEGRKFDIEEVGVATIE

KGEEPKRGRIAVAGMQVPLEDLIGKNCLVFVATKEAAETEAKELRTRGINATYYYSGIDPKTLEHGMTNQPYCIVAT

NAIESGITCPDLDVVIDTMQKYEKVVNFSAKMPLIVTSLVKKKITREEQGQRKGRVGRQKKGKYYYPSGVVPNGSKD

LSYLILQAQEYGVLEQVNITEYFIIMNEDWGLYDVDEVEVRILERMNKEILLPLGIVEKQILERSTHPEKVALLYNK

LVQKNPIVYPRVQEGEVSKEYNTYNLAVYDKLKDVNPQAIYVLAEEERATEMMGLEFEQDPSDLQDSVVQLCEDIKR

YTKLSGITEKLLVGTMVGYIGYKALTRNHVPWVSKEYCYELTDSPDTYENSFAPLDVDVQNSGEGKHPEQLADHQLR

QLLETGRDKAIDFLKGIREFTSGAINSPKALSIWEKIYQYLKKHQGEIISSAAWGSATALHDSIKSRLGDEVATAVI

ILKYLAFGERELSGLTRQVLIDIIVYYIVNKPRFEGDDYAKRKGRRLVIEVLMGALATYAVSNFWGVSINKILQPIS

DYLPYATATLAFLRPTFMESAVVVASSIYRAFLSIKHAENRSLVTQVASAALEVMGLTPVSAGLGVLLGLGLCVLHM

NIDKNEEKRTLILKMFVKNFIDQAALDELDKLEPEKIILSLLEGIQTCTNPIRAIMILYRVYYKGETFTEALSKMAG

KSLIVMVIVEFLELTGQTQGGYIDLSANLLTFLLEKLKKMTNLAIGEARKVLLPIPYLYCETWQSDARIKAPESYDQ

VVVECKCGASARYSFRDGVHEILEEKRTNWCKNFFLWGPNFHNPDPKRMTFYEYGQAKKCPVIIIGEDITFGKYGIY

IKFGHRPDGGRLIRGTTHATISREELLEILTAPSQVAIGKVKLTDYCNQKGIIDRKLAVLEGDKIHFWKAHRGSKIT

DQLTIENLTDDLGSEIRDITWELYTGGTCTVKGVSLRSCAPGHRTKAMVLCDCTDVLSPCYLINGRRPSPFDVAEGY

ECHHRKPRATYEDLEMEEILKRRVPVYDPLCLFDTDSKLLPPDTYYLEEDQEDFEYALRCWGLGVYVADGPVTSPPD

IRIHHSSVLLLLTPGVNSELPLQYIRCYPHQAEVDIYIRSQLLEEEDTATEVEGSQEDGDEGMGDAVIEDEDTSSTT

ESIPPLEEEEGGEEPITYVVIRGLQEERYASHLKLNDWISENISEPHRVQIMLDGTVRVTIKEGKVKHLFGVYRIEN

SLEAMFKETIADLPVATQPPQGPVYTAKELAQGNIAPVQPAANYYGMIEGRGDPMTAFEALSVLRSQKVLAKDVKVN

TRRAQVFLNKVRRIAEVRASELTLKCLPILGKVNGRKLIREETNIPNQRLASIMTSIGIRLEKLPVVRANTSGSKFR

QSILEKMDKYENEQVPGLHEKMWAAFLATARQDLRNTYEEVTYLELEAGINRKGAPGFFEKESSIGEVLEKKEKIDV

TIQEIEKGNHLYYETAMPKNEKRDVLDDWLSEDFVTYKKPRVIQYPEAVTRLAITKIMYKWVKQKPIVIPGYEGKTP

IFEIFEKVSADWAQFKNPVAVSFDTRAWDTQVTREDLRLVGRIQKYYYKKKYWKFIDNLTAMMEEVPVITVEGDMFL

RVGQRGSGQPDTSAGNSMLNVLTMLVAFSESTNLPIAAAWKACRIHVCGDDGFLITESELGRKFAEKGVPLLAAFGK

PQKITEGASLKVTSNFDGIEFCSHTPIRVQTPNIRWMPARPTATILGKMSTRLGEGATRSGEEYEKQVAFAYLLMYP

WNPLVRRISLLLLSTTDPMGKEETPCSDEGVKYVGDPIAAYRDVWGHKLEDVGHVDQPQLSRMNYSMTYLGIWKPKT

SQRLVEQCCRLAEKSNCVVRADSLIKKKVKITYDPGIGVAQVIRRWEELEWTRRKPELTNVIVEDDIFLVLWKRFSK

YIFQKMKFMQRMFAPY

The present disclosure also provides vectors and infectious molecular clones encoding Npro, capsid, Ems, E1, E2, NS2-3, helicase, NS4B, NS5A, or RNA-dependent RNA polymerase (RdRp) proteins of the pestivirus.

Npro: The gene encoding the N-terminal protease (Npro) protein consisting of 180 amino acids is found at positions 378 to 917 of SEQ ID NO:1.

(SEQ ID NO: 3)

ATGGAAAAACAGATTGCATATTACTTAAAAAAAGAAAAACAAAGAAATGG

GTGGACGGAACTGGTGGTAGGAGAAAGTCATACAAAAATAACCACGCTTT

-continued

CTGGAAAGACCTATCGAGGCACCTGGGAAATGGAGAAACGGCCAAATCCT

TATGGAACCTATCTCCCCAGACCTAGTCCCCAACAGCTTACAGCCCTACA

CCCCCACCCAGTGGTGAATTGTAAGGTGGTTGAGTACAAGGAGATGGACC

CTAATTATGGTGATTGCCCAAATACGAACGGGGTGTTTGTTGACGAAAAG

GGTAGAAGGCTGAGCAGCCCTCCATTAGGCATTTGGAAGATAAGATTGGA

CTATAGTGACTTGGTAAACATAAGCAGACCAACCCCCGCTAGTGGGAAAA

-continued

ACTCTTACCAAGTTGAGACCTGCAGTGGGGAGCTGGCTACAGTGACACTG

GTACACAATAGGGTGCTCGTGGAAGATTGCAGGGGGCTATACCAATGGAA

ACCCAACTGTGAAGGAATTGTGCTCTATGTGAAAACTTGT (SEQ ID NO: 4)

MEKQTAYYLKKEKQRNGWTELVVGESHTKITTLSGKTYRGTWEMEKRPNP

YGTYLPRPSPQQLTALHPHPVVNCKVVEYKEMDPNYGDCPNTNGVFVDEK

GRRLSSPPLGIWKIRLDYSDLVNISRPTPASGKNSYQVETCSGELATVTL

VHNRVLVEDCRGLYQWKPNCEGIVLYVKTC

Capsid: The gene encoding the capsid protein consisting of 111 amino acids is found at positions 918 to 1250 of SEQ ID NO:1.

(SEQ ID NO: 5)

TCTGACTGGGCAGATCAGGTAGAAAAACAGGAGAAAGAAAGCCCCCCAAA

ACCACAGCGGCCACCAAGGCGAGACCCACGAAAAGGGTTACAACCACAAG

TCCCCAAAGAGACTGAGGTCACAGAAAAGAAGAGACAACCTAGTGTCACC

TTAGTATCGGGGGGGCAGAAGGCCCAAGTCATCTACAAAGGCAGGACCAA

AAACAAAAAGACCCCGGATGGAGTCTATAGATACCCAGGAGCTAAAGAAG

GGGACGTAGTAAAGGTCAGGAAGATGCTGAAGAATTGGCATATAGCCTTA

GTGATGTACCTGATACATATCATAACTCCAGGC (SEQ ID NO: 6)

SDWADQVEKQEKESPPKPQRPPRRDPRKGLQPQVPKETEVTEKKRQPSVT

LVSGGQKAQVIYKGRTKNKKTPDGVYRYPGAKEGDVVKVRKMLKNWHIAL

VMYLIHIITPG

Ems: The gene encoding the envelope protein Ems consisting of 209 amino acids is found at positions 1251 to 1877 of SEQ ID NO:1.

(SEQ ID NO: 7)

CTTGCCAAGGTCCAGTGGTTCTTAAAAGATGAAAACTCGACGGGGATCAA

CCAGATACTGTGGCAAAGACAGATCAACAGATCCTTACATGGAGAATGGC

CTAACCAGATCTGCCACGGTATGCCCAATGAAACTATCACGGATGAGGAA

TTACGCAGTCTGGGAATGGTAGATACAAGCCCTAGAACAAACTACACCTG

TTGCCAGTTGCAATATCATGAGTGGAAGAAACATGGTTGGTGCAACTATC

CACAAAAACAGGCGTGGATCACGAGGATAACGGCCCTACAAGCTAACCTT

ACCGGGCCTTATGAGGGACCTGAGTGCGCCGTCATCTGCCGATTTAACGG

CAGCTACAACATCGTAAAACAGGCCAGAGATGAGGTGAGTCCACTGACAG

GGTGCAAGGAAGGGCATCCTTTTCTATTCTCTGGTGAAAGATCCGACACC

TCATGCCTAAGGCCCCCTTCCACTAGTTGGGTAAGACCAGTGAAAATGGA

CGAGGCATCAATGGCCGATGGCTTTGCCCATGGGGTTGATAAGGCGATAA

TACTAATCAGGAAGGGGGCATCAGGAATAATCAATTTCCTAGACACTATT

GGGAGGTGGCTACCGGTAGCTGAAGCA (SEQ ID NO: 8)

LAKVQWFLKDENSTGINQILWQRQINRSLHGEWPNQICHGMPNETITDEE

LRSLGMVDTSPRTNYTCCQLQYHEWKKHGWCNYPQKQAWITRITALQANL

-continued

TGPYEGPECAVICRFNGSYNIVKQARDEVSPLTGCKEGHPFLFSGERSDT

SCLRPPSTSWVRPVKMDEASMADGFAHGVDKAIILIRKGASGIINFLDTI

GRWLPVAEA

E1: The gene encoding the envelope protein E1 consisting of 200 amino acids is found at positions 1878 to 2477 of SEQ ID NO:1.

(SEQ ID NO: 9)

ACTATAGTACCATATTGTGATACTTACACTGTGACAGGGATGTATGTCCA

TGTAAAGAATTGCCTCCCTAGAGGGTTACCTAAGCATTCAAAAATAATCT

CCCCGACAATGATATATCTGGGAGAAGGAGACCCGGCCCATAATATCCAG

CACTTATTTGGCTCAGGTATAGCAAAGTGGGTCCTAGTTCTACTCGGGAT

TCTGGGTGAGTGGTATGGAGAATTGGCTTCCACAATATACTTACTACTAG

AATACGGGTCTGAGTGGTTGGAACATGAAAGCCTGGTCACGGAAGGGTTG

ATTCCTGGCATTAATATTACAATAGAACTCCCAGCTAGTCATACAGTGCC

TGGTTGGGTGTGGGTCGCAGGCCAGTGGGTATGCGTGAAGCCAGACTGGT

GGCCTACACAGATTTGGATTGAAACCGTGGTGGCAGAGACCTGGCATATA

CTAAAAATATTGGCGTCAGCCCTGGTGAACATAGTTGCAGCGTTCGTAAA

CCTGGAATTGGTTTATCTGGTCATAATACTAGTCAAAATATCAAAAGGGA

ACCTGATAGGTGCCATATTATGGTGCTTGTTACTGTCAGGCGCTGAAGGC (SEQ ID NO: 10)

TIVPYCDTYTVTGMYVHVKNCLPRGLPKHSKIISPTMIYLGEGDPAHNIQ

HLFGSGIAKWVLVLLGILGEWYGELASTIYLLLEYGSEWLEHESLVTEGL

IPGINITIELPASHTVPGWVWVAGQWVCVKPDWWPTQIWIETVVAETWHI

LKILASALVNIVAAFVNLELVYLVIILVKISKGNLIGAILWCLLLSGAEG

E2: The gene encoding the envelope protein E2 consisting of 372 amino acids is found at positions 2478 to 3593 of SEQ ID NO:1.

(SEQ ID NO: 11)

TCGTGCTACAAAAGACAAGACTATTACAACACCCAACTAGTCGTCGAAGA

AAAAACAGGCGTAGAAAAACGATCTATAATGGGCAAGTGGACCGTGATAA

CCAGGGAAGGTCGGGAGCCAAGATTAATGGAGCAAATAAATATGGTATTG

AATGATAGCCTGTCAGAAACCTACTGCTATAATAGGCTAAACACCAGCAC

TTGGGGGCGGCAACCGGCAAGACAAAGAGGGTGTGGTCAAACCGTGCCCT

ATTGGCCTGGTGACAATGTTCTAGAAGAACAATACTACAGCACAGGTTAC

TGGGTGAATGTAACAGGCGGTTGCCAGCTGAGAGAAGGCGTATGGCTATC

AAGAAAGGGTAACGTACAGTGTCAGCGTAACGGCTCATCCTTGATGCTGC

AATTGGCGATAAAAGAAGAGAATGACACTATGGAAATACCATGTGACCCA

GTGGAAACTGAAAGTATGGGTCCAGTTGCACAGGGCACTTGTGTGTACAG

CTGGGCATTCGCCCCCAAGAGGGTGGTACTATAACAGGAAGGATGGTTATT

GGCTCCAGTACATAAAGAAAAACGACTACCAGTATTGGACAAAAATGCCT

ACTGCCTCGTCCGCCGCAACCATGTACCGCCACTTGCTCCCCTTACTGGT

GGCCTGCCTCATGGGCGGTAGGATATCGGTGTGGTTTGTGGCAATGCTCC

-continued

TGTCTCTACAGGTGGAAGCTAGTGAAGTAGGCACTAAACAACTGGCTGTC

ACGCTAACCCTGTGGAAAATGGACTGGACAGAACTACTTTTCTATATTGT

CTTGATGCTAGCCGTTAAGGAAGAACTTATAAAAAAAATTGTGACCGCTA

GCCTTGTGGCCTTAAAAAATAGTCCAGTAGCCTTGAGTTTTCTTATTGTA

CTCAGACTTGTGGGGGGCAGTGAAGCACTCCCAGTAGGTTTATTATTAGA

AAAAATGTGCATAGACCAACCGGAGTTTGGAACTCCTTTCCTGATCTACC

TATGGGACAACTGGAAGTGGACTGTGTTAGTCAGCTTCTCCGCACTGAAC

CATGAAAAAACTATAAAACTGGCAAGAAAACTGTTGTTGGCAACACATAT

AACAGCGCTCACATTG (SEQ ID NO: 12)

SCYKRQDYYNTQLVVEEKTGVEKRSIMGKWTVITREGREPRLMEQINMVL

NDSLSETYCYNRLNTSTWGRQPARQRGCGQTVPYWPGDNVLEEQYYSTGY

WVNVTGGCQLREGVWLSRKGNVQCQRNGSSLMLQLAIKEENDTMEIPCDP

VETESMGPVAQGTCVYSWAFAPRGWYYNRKDGYWLQYIKKNDYQYWTKMP

TASSAATMYRHLLPLLVACLMGGRISVWFVAMLLSLQVEASEVGTKQLAV

TLTLWKMDWTELLFYIVLMLAVKEELIKKIVTASLVALKNSPVALSFLIV

LRLVGGSEALPVGLLLEKMCIDQPEFGTPFLIYLWDNWKWTVLVSFSALN

HEKTIKLARKLLLATHITALTL

NS2-3: The gene encoding the nonstructural protein NS2-3 consisting of 934 amino acids is found at positions 3594 to 6395 of SEQ ID NO:1.

(SEQ ID NO: 13)

ACTGGCTTGAGTGATTCAATCTTCTATATGATGCTTATAACAACAAATTT

GTTAATAAAGACATTCATATACTTGCTGGGGGCTAGTATGAATTGGGTCG

AGAGAGAAAAAAAGAAATTGCTAGTGAAGAGGAGACTAATATACAAGAAA

GCCGTTACTTGCAGTCAGGATGAGAATGTATTGGAGAATAAATTCAACAA

GATAACTGTAAACGCGGATTTCACCCCATGCAAGCTTGAACTTCTACAAT

TACTTAGGGCTTTTTTAGTCTCTTTGTGTTTTTCCTACTACAAACCTCTC

CTGTATGCAGAGACTACCTTAACTGTAATAGTAATTGGCGTACAAGAGTA

CAACGTAGCCATGGCCCGCGGGCGAAGTGTGGTCCACAGGCTACTAGCCA

TGGCCTATTACATATACGGCCGCATACAGGGTGACATGTTCCAGCTCGCC

ACTATCCAGTGCCTGCTGTCGAGTCCGAGGAAAATTATGAAACACATGGT

AGAGAATCCAACTCTCAAGAAGCTCTGGCAAGGCGAAACAGAACTCTTCA

ACCAGGGTGTTAGTCAATCCAAGATAGTGAATCCAAAGAAAATTGGGCTG

GAAGAATTACACAAGGGCATGTGTGGCCTCCCAACAGTAGTGCAAAATTT

GGTCATATATGCAAAGAAGAATGACTCTCTTATTTTAGGAGAGCTGGGTT

ACCCCCCTGGGGATCTCACCAGTGATGGGTGGGAAATTTTAGGTCCTGGC

AGAATCCCAAAGATCACTAACGTCGAGTCTGCTAAGATGGACTTACTCTC

CAAACTTATGACCTTTCTGGGGATTGAAAGCTCGAGGGTCCCCAGGACCC

CAGTCCACTCAACAAGGAAATTATTGAAGATAGTAAGGGGCTTGGAAACA

GGATGGGGGTACACTCACGCAGGGGGGATAAGTAGCGCAAAACACGTTAC

AGGTGAAAAGAACTTAATGACCCACATGGAGGGTAGGAAGGGAAAATATA

-continued

TCCTACAATCTCAAGAACATGGTGCTGACGAGGTAGAGTACGGAGTAAAA

ACTGATCAAAAAGCTCCCGACAATGCCTTATGCTACTGTTTTAACCCTGA

AGCTACAAACATAAAAGGAGAGACGGGAGCCATGGTGTTCATGAAGAAGA

TAGGAAAAAAAGTGGACTCTCGTAACATCAGACGGCAATAAAGCCTATTAT

AATGTAAACAATTTGAAAGGGTGGTCTGGACTACCAATAATGCTGCACTC

CACCGGGGCCATAGTGGGGAGGATTAAATCAGCGTATTCAGATGAAAACG

ACCTGGTGGAGGAACTTATTGACTCTAGAACTATTAGTAAGAGCAATGAG

ACAAACCTGGACCACCTTATCAAGGAATTGGCAGACATGCGGAGGGGGGA

GTTCCGCTCAATTACCCTTGGAACGGGAGCCGGGAAAACCACAGAACTGC

CTAGGCAATACCTCACAACAGTAGGTGCCCATAAATCCGTGCTGGTCTTA

GTCCCCTTAAAAGCACCTGCTGAAAGTGTTTGCCGCTTTATGAGGTCTAA

ATACCCTACCATCAACTTTTCCTTAAGAGTGGGGGAACGGAAAGAGGGAG

ATGTGAGCAGCGGCATCACCTACGCTACTTACGGATTTTGCTGCCAGCTA

AACCTAGTCCAACTTAAAGAATGGATATCCAGGTACTCAATGGTTTTTTT

TGATGAATATCACACAGCAACTCCAGAACAAATAGCCATAATAAGCAAGA

TTCATGCACTGAAAGTTAAGACCAGGATAGTGGCTATGTCAGCAACCCCC

CCGGGTACCGTGACGACTGAAGGCAGGAAGTTTGACATTGAAGAGGTAGG

GGTTGCTACCATAGAGAAAGGAGAGGAACCAAAAAGGGGGCGCATAGCGG

TCGCTGGTATGCAGGTCCCATTAGAAGACTTAACAGGAAAGAACTGCCTG

GTGTTCGTGGCAACCAAAGAAGCCGCGGAGACGGAGGCTAAAGAACTGCG

CACCAGAGGAATTAACGCCACCTACTACTATTCAGGTATAGACCCTAAGA

CTCTGGAACATGGGATGACCAATCAGCCATACTGTATTGTAGCTACCAAT

GCCATTGAATCAGGTATAACCTGTCCTGACTTGGATGTGGTCATAGACAC

CATGCAGAAGTACGAAAAAGTAGTGAATTTCTCGGCAAAGATGCCCTTGA

TTGTCACTTCATTAGTAAAGAAAAAAATCACCAGGGAAGAACAGGGCCAG

AGGAAAGGTCGAGTGGGCAGGCAAAAGAAAGGAAAATACTACTACCCCTC

GGGGGTGGTACCGAATGGGTCAAAAGACCTAAGCTATTTAATCCTACAGG

CCCAAGAATATGGTGTCTTGGAACAAGTCAATATAACAGAGTACTTCATC

ATAATGAATGAGGACTGGGGTCTCTATGACGTAGATGAAGTAGAAGTGAG

AATACTTGAGAGAATGAACAAGGAAATCTTGCTACCACTAGGTATTGTGG

AGAAGCAAATCTTGGAAAGAAGTACTCACCCGGAAAAAGTGGCACTGTTG

TATAACAAATTAGTGCAGAAAAATCCTATAGTATACCCTAGAGTACAGGA

AGGTGAGGTCAGCAAGGAATACAATACCTATAATCTGGCCGTATATGACA

AGCTAAAAGATGTCAACCCACAAGCCATTTATGTTCTAGCAGAAGAGGAG

AGAGCCACAGAAATGATGGGTCTCGAGTTTGAACAAGACCCATCTGACTT

ACAGGATTCGGTAGTTCAGCTTTGTGAAGATATCAAGAGGTATACAAAAC

TC (SEQ ID NO: 14)

TGLSDSIFYMMLITTNLLIKTFIYLLGASMNWVEREKKKLLVKRRLIYKK

AVTCSQDENVLENKFNKITVNADFTPCKLELLQLLRAFLVSLCFSYYKPL

LYAETTLTVIVIGVQEYNVAMARGRSVVHRLLAMAYYIYGRIQGDMFQLA

```
TIQCLLSSPRKIMKHMVENPTLKKLWQGETELFNQGVSQSKIVNPKKIGL

EELHKGMCGLPTVVQNLVIYAKKNDSLILGELGYPPGDLTSDGWEILGPG

RIPKITNVESAKMDLLSKLMTFLGIESSRVPRTPVHSTRKLLKIVRGLET

GWGYTHAGGISSAKHVTGEKNLMTHMEGRKGKYILQSQEHGADEVEYGVK

TDQKAPDNALCYCFNPEATNIKGETGAMVFMKKIGKKWTLVTSDGNKAYY

NVNNLKGWSGLPIMLHSTGAIVGRIKSAYSDENDLVEELIDSRTISKSNE

TNLDHLIKELADMRRGEFRSITLGTGAGKTTELPRQYLTTVGAHKSVLVL

VPLKAPAESVCRFMRSKYPTINFSLRVGERKEGDVSSGITYATYGFCCQL

NLVQLKEWISRYSMVFFDEYHTATPEQTAIISKIHALKVKTRIVAMSATP

PGTVTTEGRKFDIEEVGVATIEKGEEPKRGRIAVAGMQVPLEDLTGKNCL

VFVATKEAAETEAKELRTRGINATYYYSGIDPKTLEHGMTNQPYCIVATN

AIESGITCPDLDVVIDTMQKYEKVVNFSAKMPLIVTSLVKKKITREEQGQ

RKGRVGRQKKGKYYYPSGVVPNGSKDLSYLILQAQEYGVLEQVNITEYFI

IMNEDWGLYDVDEVEVRILERMNKEILLPLGIVEKQILERSTHPEKVALL

YNKLVQKNPIVYPRVQEGEVSKEYNTYNLAVYDKLKDVNPQAIYVLAEEE

RATEMMGLEFEQDPSDLQDSVVQLCEDIKRYTKL
```

Helicase: The gene encoding the helicase protein consisting of 687 amino acids is found at positions 4335 to 6395 of SEQ ID NO:1.

(SEQ ID NO: 15)

```
GGTCCTGGCAGAATCCCAAAGATCACTAACGTCGAGTCTGCTAAGATGGA
CTTACTCTCCAAACTTATGACCTTTCTGGGGATTGAAAGCTCGAGGGTCC
CCAGGACCCCAGTCCACTCAACAAGGAAATTATTGAAGATAGTAAGGGGC
TTGGAAACAGGATGGGGGTACACTCACGCAGGGGGGATAAGTAGCGCAAA
ACACGTTACAGGTGAAAAGAACTTAATGACCCACATGGAGGGTAGGAAGG
GAAAATATATCCTACAATCTCAAGAACATGGTGCTGACGAGGTAGAGTAC
GGAGTAAAAACTGATCAAAAAGCTCCCGACAATGCCTTATGCTACTGTTT
TAACCCTGAAGCTACAAACATAAAAGGAGAGACGGGAGCCATGGTGTTCA
TGAAGAAGATAGGAAAAAAGTGGACTCTCGTAACATCAGACGGCAATAAA
GCCTATTATAATGTAAACAATTTGAAAGGGTGGTCTGGACTACCAATAAT
GCTGCACTCCACCGGGGCCATAGTGGGGAGGATTAAATCAGCGTATTCAG
ATGAAAACGACCTGGTGGAGGAACTTATTGACTCTAGAACTATTAGTAAG
AGCAATGAGACAAACCTGGACCACCTTATCAAGGAATTGGCAGACATGCG
GAGGGGGGAGTTCCGCTCAATTACCCTTGGAACGGGAGCCGGGAAAACCA
CAGAACTGCCTAGGCAATACCTCACAACAGTAGGTGCCCATAAATCCGTG
CTGGTCTTAGTCCCCTTAAAAGCACCTGCTGAAAGTGTTTGCCGCTTTAT
GAGGTCTAAATACCCTACCATCAACTTTTCCTTAAGAGTGGGGGAACGGA
AAGAGGGAGATGTGAGCAGCGGCATCACCTACGCTACTTACGGATTTTGC
TGCCAGCTAAACCTAGTCCAACTTAAAGAATGGATATCCAGGTACTCAAT
GGTTTTTTTTGATGAATATCACACAGCAACTCCAGAACAAATAGCCATAA
TAAGCAAGATTCATGCACTGAAAGTTAAGACCAGGATAGTGGCTATGTCA
```

-continued

```
GCAACCCCCCCGGGTACCGTGACGACTGAAGGCAGGAAGTTTGACATTGA
AGAGGTAGGGGTTGCTACCATAGAGAAAGGAGAGGAACCAAAAAGGGGGC
GCATAGCGGTCGCTGGTATGCAGGTCCCATTAGAAGACTTAACAGGAAAG
AACTGCCTGGTGTTCGTGGCAACCAAAGAAGCCGCGGAGACGGAGGCTAA
AGAACTGCGCACCAGAGGAATTAACGCCACCTACTACTATTCAGGTATAG
ACCCTAAGACTCTGGAACATGGGATGACCAATCAGCCATACTGTATTGTA
GCTACCAATGCCATTGAATCAGGTATAACCTGTCCTGACTTGGATGTGGT
CATAGACACCATGCAGAAGTACGAAAAAGTAGTGAATTTCTCGGCAAAGA
TGCCCTTGATTGTCACTTCATTAGTAAAGAAAAAAATCACCAGGGAAGAA
CAGGGCCAGAGGAAAGGTCGAGTGGGCAGGCAAAAGAAAGGAAAATACTA
CTACCCCTCGGGGGTGGTACCGAATGGGTCAAAAGACCTAAGCTATTTAA
TCCTACAGGCCCAAGAATATGGTGTCTTGGAACAAGTCAATATAACAGAG
TACTTCATCATAATGAATGAGGACTGGGGTCTCTATGACGTAGATGAAGT
AGAAGTGAGAATACTTGAGAGAATGAACAAGGAAATCTTGCTACCACTAG
GTATTGTGGAGAAGCAAATCTTGGAAAGAAGTACTCACCCGGAAAAAGTG
GCACTGTTGTATAACAAATTAGTGCAGAAAAATCCTATAGTATACCCTAG
AGTACAGGAAGGTGAGGTCAGCAAGGAATACAATACCTATAATCTGGCCG
TATATGACAAGCTAAAAGATGTCAACCCACAAGCCATTTATGTTCTAGCA
GAAGAGGAGAGAGCCACAGAAATGATGGGTCTCGAGTTTGAACAAGACCC
ATCTGACTTACAGGATTCGGTAGTTCAGCTTTGTGAAGATATCAAGAGGT
ATACAAAACTC
```

(SEQ ID NO: 16)

```
GPGRIPKITNVESAKMDLLSKLMTFLGIESSRVPRTPVHSTRKLLKIVRG
LETGWGYTHAGGISSAKHVTGEKNLMTHMEGRKGKYILQSQEHGADEVEY
GVKTDQKAPDNALCYCFNPEATNIKGETGAMVFMKKIGKKWTLVTSDGNK
AYYNVNNLKGWSGLPIMLHSTGAIVGRIKSAYSDENDLVEELIDSRTISK
SNETNLDHLIKELADMRRGEFRSITLGTGAGKTTELPRQYLTTVGAHKSV
LVLVPLKAPAESVCRFMRSKYPTINFSLRVGERKEGDVSSGITYATYGFC
CQLNLVQLKEWISRYSMVFFDEYHTATPEQIAIISKIHALKVKTRIVAMS
ATPPGTVTTEGRKFDIEEVGVATIEKGEEPKRGRIAVAGMQVPLEDLTGK
NCLVFVATKEAAETEAKELRTRGINATYYYSGIDPKTLEHGMTNQPYCIV
ATNAIESGITCPDLDVVIDTMQKYEKVVNFSAKMPLIVTSLVKKKITREE
QGQRKGRVGRQKKGKYYYPSGVVPNGSKDLSYLILQAQEYGVLEQVNITE
YFIIMNEDWGLYDVDEVEVRILERMNKEILLPLGIVEKQILERSTHPEKV
ALLYNKLVQKNPIVYPRVQEGEVSKEYNTYNLAVYDKLKDVNPQAIYVLA
EEERATEMMGLEFEQDPSDLQDSVVQLCEDIKRYTKL
```

NS4B: The gene encoding the nonstructural protein NS4B consisting of 67 amino acids is found at positions 6396 to 6596 of SEQ ID NO:1.

(SEQ ID NO: 17)

TCTGGGATCACTGAGAAACTGCTAGTAGGTACGATGGTGGGGTATATTGG

ATACAAAGCCTTAACCAGAAACCACGTGCCCTGGGTCAGCAAAGAGTATT

GTTATGAGCTGACCGATTCACCGGATACTTACGAAAACTCATTCGCACCT

TTGGACGTCGACGTCCAAAACTCCGGTGAAGGAAAACACCCAGAGCAACT

G (SEQ ID NO: 18)

SGITEKLLVGTMVGYIGYKALTRNHVPWVSKEYCYELTDSPDTYENSFAP

LDVDVQNSGEGKHPEQL

NS5A: The gene encoding the nonstructural protein NS5A consisting of 811 amino acids is found at positions 6597 to 9029 of SEQ ID NO:1.

(SEQ ID NO: 19)

GCAGACCATCAATTGAGGCAACTACTGGAGACTGGGAGAGACAAGGCAAT

TGATTTCCTAAAAGGAATCCGCGAGTTCACTAGTGGGGCCATAAACAGTC

CAAAGGCACTAAGTATATGGGAGAAAATATATCAGTATTTGAAGAAGCAT

CAGGGCGAGATCATCTCATCAGCAGCGTGGGGCAGTGCGACGGCCCTTCA

CGACAGTATTAAATCTAGACTAGGAGATGAGGTCGCTACTGCAGTAATAA

TCCTCAAGTATTTAGCATTTGGTGAAAGAGAACTGTCTGGGCTAACTAGG

CAAGTTCTAATTGACATCATAGTATATTATATAGTTAACAAGCCCCGGTT

CGAAGGAGACGACTACGCAAAGAGAAAAGGAAGAAGGCTAGTCATCGAAG

TCCTGATGGGGGCACTGGCGACTTATGCGGTGTCCAATTTTTGGGGTGTG

TCCATTAATAAGATACTGCAACCAATTTCTGATTATCTACCCTATGCCAC

CGCCACTTTGGCTTTTCTTCGCCCAACCTTCATGGAATCAGCAGTGGTGG

TCGCTTCCTCTATCTATAGAGCTTTTCTCTCCATTAAGCATGCGGAAAAC

AGGAGTCTTGTCACGCAGGTCGCTTCTGCCGCCCTCGAAGTCATGGGCCT

GACCCCAGTATCGGCTGGCCTAGGCGTCTTGCTGGGGCTTGGGTTGTGTG

TGCTCCATATGAACATTGACAAGAATGAGGAGAAAAGGACACTTATACTG

AAAATGTTTGTCAAAAACTTTATAGACCAGGCGGCACTAGACGAGTTGGA

TAAACTGGAGCCAGAAAAAATAATCCTCTCATTGTTGGAGGGTATCCAAA

CCTGCACAAACCCGATTAGAGCAATCATGATTTTGTACAGGGTGTACTAC

AAGGGAGAAACTTTCACAGAAGCTTTGTCTAAGATGGCCGGCAAGTCTCT

CATTGTGATGGTCATAGTCGAGTTCCTGGAATTGACAGGCCAAACCCAAG

GAGGGTATATAGATCTTAGTGCTAATTTGCTGACCTTTCTCCTCGAGAAA

CTAAAAAAAATGACTAACCTCGCCATCGGGGAAGCTAGAAAGGTCTTGCT

CCCCATCCCATACTTGTACTGTGAAACCTGGCAGTCTGACGCCAGAATCA

AGGCCCCTGAATCCTACGACCAAGTGGTAGTGGAATGCAAATGTGGCGCT

TCAGCGAGGTATTCCTTCCGCGATGGAGTTCATGAGATATTGGAAGAAAA

AAGGACTAATTGGTGCAAGAACTTCTTCTTATGGGGACCCAACTTCCACA

ATCCGGATCCAAAAAGGATGACATTCTATGAATACGGCCAAGCAAAAAAG

TGTCCTGTTATCATAATTGGTGAAGACATAACCTTCGGCAAATATGGCAT

ATATATCAAATTTGGCCATAGGCCTGATGGAGGGAGGTTAATAAGGGGTA

-continued

CCACCCACGCTACTATCAGTAGGGAGGAATTGCTGGAAATCCTAACAGCC

CCAAGCCAAGTGGCCATAGGCAAGGTCAAGCTAACCGATTACTGTAATCA

AAAAGGAATAATAGACAGGAAATTGGCCGTACTTGAAGGTGACAAAATAC

ATTTTTGGAAAGCACACCGTGGATCCAAAATCACAGACCAACTCACTATT

GAGAATCTGACAGATGATTTGGGGTCAGAAATCAGGGACATCACATGGGA

GCTGTACACAGGTGGAACGTGCACCGTAAAAGGGGTGTCCCTTAGATCAT

GCGCACCAGGTCATAGAACTAAGGCTATGGTCTTGTGTGATTGCACTGAT

GTGCTTAGCCCCTGTTACCTAATAAACGGCAGGAGACCATCCCCATTTGA

CGTCGCGGAAGGTTATGAATGTCACCACCGGAAGCCCCGAGCGACGTATG

AAGACCTAGAAATGGAGGAAATACTAAAGAGACGAGTCCCTGTCTACGAT

CCTCTGTGTTTGTTTGACACTGATAGTAAACTGCTACCTCCCGACACCTA

CTACTTGGAAGAAGATCAAGAGGACTTTGAGTACGCATTGAGATGCTGGG

GCCTCGGGGTTTATGTAGCAGACGGGCCTGTCACTTCCCCCCCGGACATA

AGAATACACCATAGTTCGGTATTACTACTGCTGACACCTGGAGTAAACTC

AGAGTTGCCCTTACAGTACATACGTTGTTACCCTCATCAGGCAGAGGTGG

ACATCTACATTAGGAGTCAGCTTTTGGAGGAGGAAGACACTGCTACGGAG

GTGGAAGGCTCCCAGGAAGATGGTGATGAAGGGATGGGCGATGCGGTAAT

AGAGGATGAGGATACATCGTCCACAACAGAATCAATACCCCCACTAGAAG

AGGAGGAAGGGGGCGAAGAGCCAATCACCTATGTGGTCATAAGGGGATTA

CAAGAAGAAAGATACGCCAGCCATCTTAAACTA (SEQ ID NO: 20)

ADHQLRQLLETGRDKAIDFLKGIREFTSGAINSPKALSIWEKIYQYLKKH

QGEIISSAAWGSATALHDSIKSRLGDEVATAVIILKYLAFGERELSGLTR

QVLIDIIVYYIVNKPRFEGDDYAKRKGRRLVIEVLMGALATYAVSNFWGV

SINKILQPISDYLPYATATLAFLRPTFMESAVVVASSIYRAFLSIKHAEN

RSLVTQVASAALEVMGLTPVSAGLGVLLGLGLCVLHMNIDKNEEKRTLIL

KMFVKNFIDQAALDELDKLEPEKIILSLLEGIQTCTNPIRAIMILYRVYY

KGETFTEALSKMAGKSLIVMVIVEFLELTGQTQGGYIDLSANLLTFLLEK

LKKMTNLAIGEARKVLLPIPYLYCETWQSDARIKAPESYDQVVVECKCGA

SARYSFRDGVHEILEEKRTNWCKNFFLWGPNFHNPDPKRMTFYEYGQAKK

CPVIIIGEDITFGKYGIYIKFGHRPDGGRLIRGTTHATISREELLEILTA

PSQVAIGKVKLTDYCNQKGIIDRKLAVLEGDKIHFWKAHRGSKITDQLTI

ENLTDDLGSEIRDITWELYTGGTCTVKGVSLRSCAPGHRTKAMVLCDCTD

VLSPCYLINGRRPSPFDVAEGYECHHRKPRATYEDLEMEEILKRRVPVYD

PLCLFDTDSKLLPPDTYYLEEDQEDFEYALRCWGLGVYVADGPVTSPPDI

RIHHSSVLLLLTPGVNSELPLQYIRCYPHQAEVDIYIRSQLLEEEDTATE

VEGSQEDGDEGMGDAVIEDEDTSSTTESIPPLEEEEGGEEPITYVVIRGL

QEERYASHLKL

RdRp: The gene encoding the RNA-dependent RNA polymerase consisting of 751 amino acids is found at positions 9030 to 11285 of SEQ ID NO:1.

(SEQ ID NO: 21)

AATGACTGGATCAGTGAAAACATTTCAGAGCCACACAGAGTCCAAATTAT

GCTAGATGGGACAGTGAGAGTCACAATAAAAGAGGGCAAAGTGAAACATT

TGTTTGGGGTCTATAGAATAGAAAACTCCCTGGAAGCAATGTTTAAAGAG

ACCATAGCTGACCTCCCCGTAGCTACCCAACCGCCCCAGGGGCCAGTCTA

TACGGCTAAAGAGCTGGCCCAAGGGAACATCGCCCCGGTCCAACCTGCAG

CGAATTATTACGGAATGATAGAGGGGAGAGGCGACCCAATGACGGCATTC

GAAGCCTTATCAGTCTTGCGGTCACAAAAAGTCTTAGCCAAGGACGTGAA

GGTGAACACCCGCAGGGCGCAGGTTTTTTAAATAAAGTCAGGAGAATTG

CTGAGGTCAGAGCGTCGGAACTGACATTAAAATGCTTACCGATACTTGGC

AAAGTAAATGGGAGGAAATTGATTAGAGAGGAAACCAACATCCCCAACCA

AAGGTTGGCATCAATAATGACCTCAATAGGAATTAGACTAGAAAAACTGC

CAGTGGTTAGAGCAAACACTTCCGGCTCTAAGTTCAGACAGTCAATCTTA

GAAAAAATGGATAAGTATGAAAATGAACAAGTCCCAGGGTTACATGAAAA

GATGTGGGCAGCGTTCCTGGCAACTGCCAGGCAAGATTTAAGAAATACCT

ATGAGGAAGTAACTTATCTTGAATTAGAGGCCGGAATCAATCGGAAAGGA

GCCCCAGGTTTCTTTGAAAAAGAAAGCTCAATAGGAGAAGTGCTGGAAAA

AAAAGAAAAAATTGACGTCACAATCCAAGAGATTGAAAAAGGCAACCACT

TATACTATGAAACAGCCATGCCAAAAAATGAGAAAAGAGATGTGCTTGAT

GATTGGTTGTCAGAGGATTTCGTCACTTATAAGAAACCACGTGTGATACA

GTACCCTGAGGCAGTCACCCGGTTGGCCATCACCAAAATAATGTATAAGT

GGGTGAAGCAAAAGCCTATAGTGATTCCCGGTTATGAGGGAAAAACCCCG

ATCTTTGAAATATTTGAAAAAGTCAGTGCAGATTGGGCTCAGTTCAAAAA

TCCGGTAGCCGTCAGCTTCGACACCAGAGCCTGGGACACTCAAGTAACAA

GAGAAGACCTCAGGCTGGTAGGGCGGATACAGAAATACTATTACAAAAAA

AAATATTGGAAGTTCATTGACAATTTGACAGCCATGATGGAGGAAGTGCC

TGTAATCACTGTAGAAGGAGATATGTTCCTCAGAGTTGGACAGCGCGGAT

CCGGACAGCCTGATACCTCAGCAGGCAATTCCATGCTAAATGTGCTGACT

ATGTTGGTAGCTTTCTCTGAATCCACAAATCTGCCCATAGCGGCTGCCTG

GAAGGCCTGTCGGATCCACGTCTGTGGTGACGACGGTTTCTTAATCACAG

AATCGGAATTAGGGAGGAAGTTTGCTGAAAAAGGTGTTCCTCTGTTAGCT

GCATTTGGCAAACCCCAAAAAATTACAGAGGGAGCGAGCCTAAAGGTAAC

CAGCAACTTTGACGGAATAGAGTTTTGTAGTCATACCCCTATCAGAGTCC

AAACACCAAACATCAGGTGGATGCCAGCGAGACCAACAGCAACAATCCTA

GGCAAAATGAGTACCAGGCTGGGTGAGGGTGCCACCAGGTCGGGAGAAGA

ATACGAAAAACAGGTGGCATTCGCATATCTACTGATGTACCCCTGGAACC

CGCTGGTCAGGAGAATCAGCCTCCTATTGTTATCGACTACTGACCCAATG

GGGAAAGAGGAAACCCCATGCTCCGATGAGGGGGTGAAGTATGTTGGGGA

CCCTATCGCTGCATACAGGGATGTATGGGGGCACAAATTAGAGGATGTAG

GCCATGTTGATCAACCGCAGTTATCCCGGATGAACTATAGCATGACTTAC

TTAGGGATTTGGAAACCAAAGACAAGTCAGCGGCTAGTCGAACAGTGTTG

-continued

TCGTCTGGCCGAGAAAAGCAATTGTGTGGTACGTGCTGACTCCCTGATAA

AGAAAAAGGTCAAGATCACTTATGACCCGGGGATAGGAGTGGCTCAGGTC

ATTCGTAGGTGGGAAGAGCTTGAGTGGACCAGAAGGAAACCTGAACTCAC

CAATGTAATTGTAGAAGATGATATCTTCCTAGTCCTGTGGAAGAGATTTT

CAAAGTACATTTTTCAGAAAATGAAGTTCATGCAGAGAATGTTCGCCCCT

TATTAA (SEQ ID NO: 22)

NDWISENISEPHRVQIMLDGTVRVTIKEGKVKHLFGVYRIENSLEAMFKE

TIADLPVATQPPQGPVYTAKELAQGNIAPVQPAANYYGMIEGRGDPMTAF

EALSVLRSQKVLAKDVKVNTRRAQVFLNKVRRIAEVRASELTLKCLPILG

KVNGRKLIREETNIPNQRLASIMTSIGIRLEKLPVVRANTSGSKFRQSIL

EKMDKYENEQVPGLHEKMWAAFLATARQDLRNTYEEVTYLELEAGINRKG

APGFFEKESSIGEVLEKKEKIDVTIQEIEKGNHLYYETAMPKNEKRDVLD

DWLSEDFVTYKKPRVIQYPEAVTRLAITKIMYKWVKQKPIVIPGYEGKTP

IFEIFEKVSADWAQFKNPVAVSFDTRAWDTQVTREDLRLVGRIQKYYYKK

KYWKFIDNLTAMMEEVPVITVEGDMFLRVGQRGSGQPDTSAGNSMLNVLT

MLVAFSESTNLPIAAAWKACRIHVCGDDGFLITESELGRKFAEKGVPLLA

AFGKPQKITEGASLKVTSNFDGIEFCSHTPIRVQTPNIRWMPARPTATIL

GKMSTRLGEGATRSGEEYEKQVAFAYLLMYPWNPLVRRISLLLLSTTDPM

GKEETPCSDEGVKYVGDPIAAYRDVWGHKLEDVGHVDQPQLSRMNYSMTY

LGIWKPKTSQRLVEQCCRLAEKSNCVVRADSLIKKKVKITYDPGIGVAQV

IRRWEELEWTRRKPELTNVIVEDDIFLVLWKRFSKYIFQKMKFMQRMFAP

Y

In one embodiment, the pestivirus according to the invention is a pestivirus mutant, in particular comprising, in comparison with the genome of a wild type pestivirus, a mutation in a gene encoding a protein of said virus.

In a preferred embodiment, the pestivirus according to the invention comprises a mutation in the gene encoding Npro, capsid, Erns, E1, E2, NS2-3, helicase, NS4B, NS5A, or RdRp proteins of said virus. Thus, the invention preferably concerns a pestivirus which exhibits a reduced viral fitness as a result of a mutation in the gene encoding the pestivirus polyprotein, wherein said mutation is preferably a mutation as mentioned hereinafter.

Preferably, the mutation, as described herein, comprises or consists of one or more point mutations and/or one or more genomic deletions and/or one or more insertions.

The immunogenic composition as used herein also refers to a composition that comprises any of the pestivirus polyprotein described herein. According to a further embodiment, such immunogenic composition further comprises at least a portion of a viral vector expressing said pestivirus polyprotein and specifically the E2 protein, preferably of a recombinant baculovirus. Moreover, the immunogenic composition can comprise i) any of the pestivirus proteins described above, preferably in concentrations described above, ii) at least a portion of the viral vector expressing said pestivirus polyprotein of processed proteins within the polyprotein, preferably of a recombinant baculovirus, and iii) a portion of the cell culture supernatant.

According to a further embodiment, the present invention also relates to a vector that comprises any of such nucleic acid molecules as described herein. In other words, the present invention relates to a vector, that includes the coding sequence of any such pestivirus polyprotein, or part thereof. Preferably, said vector is an expression vector, which allows the expression of any such pestivirus polyprotein or part of the protein. Vectors according to the invention are those which are suitable for the transfection or infection of bacterial, yeast or animal cells, in vitro or in vivo.

The present vaccines typically include inactivated or attenuated pestiviruses formulated with a pharmaceutically acceptable carrier. The pharmaceutical forms suitable for injectable use commonly include sterile aqueous solutions (where water soluble) or dispersions and sterile powders for the extemporaneous preparation of sterile injectable solutions or dispersion. The formulation should desirably be sterile and fluid to the extent that easy syringability exists. The dosage form should be stable under the conditions of manufacture and storage and typically is preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. One possible carrier is a physiological salt solution. The proper fluidity of the solution can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabenes, chlorobutanol, phenol, sorbic acid, thimerosal (sodium ethylmercuri-thiosalicylate), deomycin, gentamicin and the like. In many cases it may be preferable to include isotonic agents, for example, sugars or sodium chloride. Prolonged absorption of the injectable compositions, if desired, can be brought about by the use in the compositions of agents delaying absorption, for example, aluminum monostearate and gelatin.

The volume of a single dose of the vaccine of this invention may vary but will be generally within the ranges commonly employed in conventional vaccines. The volume of a single dose is preferably between about 0.1 ml and about 3 ml, preferably between about 0.2 ml and about 1.5 ml, more preferably between about 0.2 ml and about 0.5 ml at the concentrations of conjugate and adjuvant noted above.

The vaccine compositions of the invention may be administered by any convenient means known in the art, e.g., intramuscularly, subcutaneously, intravenously, orally, intraarterially, intranasally (e.g., with or without inhalation), intracardially, intraspinally, intrathoracically, intraperitoneally, intraventricularly, sublingually, transdermally, and/or via inhalation.

The subject to which the composition is administered is preferably an animal, including but not limited to pigs, cows, horses, sheep, poultry (e.g., chickens), goats, cats, dogs, hamsters, mice, and rats. Most preferably, the mammal is a swine, more preferably, a sow, gilt, or piglet. In some embodiments, the sow or gilt can be pregnant.

The formulations of the invention comprise an effective immunizing amount of one or more immunogenic compositions and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder.

Oral formulation can include standard carriers such as pharmaceutical grades of mannitol, lactose, starch, magnesium stearate, sodium saccharine, cellulose, magnesium carbonate, etc.

Preferred routes of administration include but are not limited to intranasal, oral, intradermal, and intramuscular. Administration intramuscularly or intravaginally, most preferably in a single dose, is desirable. The skilled artisan will recognize that compositions of the invention may also be administered in one, two or more doses, as well as, by other routes of administration. For example, such other routes include subcutaneously, intracutaneously, intravenously, intravascularly, intraarterially, intraperitnoeally, intrathecally, intratracheally, intracutaneously, intracardially, intralobally, intramedullarly, or intrapulmonarily. Depending on the desired duration and effectiveness of the treatment, the compositions according to the invention may be administered once or several times, also intermittently, for instance on a daily basis for several days, weeks or months and in different dosages.

Embodiments of the invention also include a method for protecting a piglet against diseases associated with pestivirus, comprising administering to a pregnant sow or gilt, any of the attenuated vaccines described herein. For example, the administered vaccine comprises one or more antigens of pestivirus.

Thus according to one aspect, the present invention relates to a method for reducing the percentage of pestivirus infections in a herd of piglets comprising the step administering to pregnant sows or gilts an effective amount of inactivated or attenuated pestivirus antigen or an immunogenic composition comprising pestivirus antigen, wherein the pestivirus antigen is an inactivated pestivirus, attenuated pestivirus, or subunit vaccine.

In one embodiment, the pestivirus of the invention is any pestivirus encoded by or comprising the sequence of SEQ ID NO:1 or 2; which sequence is at least 99% identical with the SEQ ID NO:1 or 2; and/or which the pestivirus is encoded by a nucleic acid sequence at least 90% identical with the SEQ ID NO:1 or 2.

In another embodiment, the method includes administration of a vaccine comprising one or more immunogenic components selected from the group consisting of a pestivirus that is encoded by or comprises the sequence of SEQ ID NO:1; which sequence is at least 99% identical with the SEQ ID NO:2; which the polyprotein is encoded by nucleic acid sequences of SEQ ID NO:1 or 2; and/or which pestivirus polyprotein is encoded by a nucleic acid sequence that is at least 90% identical with the SEQ ID NO:1 or 2.

The compounds described herein can be administered to a subject at therapeutically effective doses to treat pestivirus associated diseases. The dosage will depend upon the host receiving the vaccine as well as factors such as the size, weight, and age of the host.

Immunogenicity of a composition can be determined by monitoring the immune response of test subjects following immunization with the composition by use of any immunoassay known in the art. Generation of a humoral (antibody) response and/or cell-mediated immunity may be taken as an indication of an immune response. Test subjects may include animals such as pigs, mice, hamsters, dogs, cats, rabbits, cows, horses, sheep, and poultry (e.g., chickens, ducks, geese, and turkeys).

The immune response of the test subjects can be analyzed by various approaches such as: the reactivity of the resultant immune serum to the immunogenic conjugate, as assayed by known techniques, e.g., enzyme linked immunosorbent assay (ELISA), immunoblots, immunoprecipitations, etc.; or, by protection of immunized hosts from infection by the pathogen and/or attenuation of symptoms due to infection by the pathogen in immunized hosts as determined by any method known in the art, for assaying the levels of an infectious disease agent, e.g., the bacterial levels (for example, by culturing of a sample from the subject), or other technique known in the art. The levels of the infectious disease agent may also be determined by measuring the levels of the antigen against which the immunoglobulin was directed. A decrease in the levels of the infectious disease agent or an amelioration of the symptoms of the infectious disease indicates that the composition is effective.

The therapeutics of the invention can be tested in vitro for the desired therapeutic or prophylactic activity, prior to in vivo use in animals or humans. For example, in vitro assays that may be used to determine whether administration of a specific therapeutic is indicated include in vitro cell culture assays in which appropriate cells from a cell line or cells cultured from a subject having a particular disease or disorder are exposed to or otherwise administered a therapeutic, and the effect of the therapeutic on the cells is observed.

Alternatively, the therapeutic may be assayed by contacting the therapeutic to cells (either cultured from a subject or from a cultured cell line) that are susceptible to infection by the infectious disease agent but that are not infected with the infectious disease agent, exposing the cells to the infectious disease agent, and then determining whether the infection rate of cells contacted with the therapeutic was lower than the infection rate of cells not contacted with the therapeutic. Infection of cells with an infectious disease agent may be assayed by any method known in the art.

In addition, the therapeutic can be assessed by measuring the level of the molecule against which the antibody is directed in the animal model or human subject at suitable time intervals before, during, or after therapy. Any change or absence of change in the amount of the molecule can be identified and correlated with the effect of the treatment on the subject. The level of the molecule can be determined by any method known in the art.

After vaccination of an animal to a pestivirus vaccine or immunogenic composition using the methods and compositions of the present invention, any binding assay known in the art can be used to assess the binding between the resulting antibody and the particular molecule. These assays may also be performed to select antibodies that exhibit a higher affinity or specificity for the particular antigen.

In general, attenuation of virus may be generated from pathogenic virus isolates by repeated passaging in suitable host cells that are permissive to the virus until the virus shows the desired properties (WO 92/21375, WO 93/06211, WO93/03760, WO 93/07898, WO 96/36356, EP 0 676 467, EP 0 732 340, EP 0 835 930). Alternatively, it may be generated by genetic reengineering through use of an infectious clone, normally a full-length complementary DNA transcript of the viral genome (WO 98/18933, EP 1 018 557, WO 03/062407, Nielsen et al., J Virol 2003, 77:3702-3711). Additionally, the virus may be passaged under non-native physiological conditions which include, but are not limited to, modified temperature, cells from non-host species or in the presence of mutagens.

The invention extends to pestivirus strains which are derived from the strains through propagation or multiplication in an identical or divergent form, in particular descendants which possess the essential characteristics of the deposited strains. Upon continued propagation, the strains may acquire mutations most of which will not alter the properties of these strains significantly.

In another aspect, the present invention contemplates preparation and isolation of a progeny or descendant of a pestivirus SEQ ID NO:1 or 2. The invention therefore extends to pestivirus strains which are derived from the identified strains through propagation or multiplication in an identical or divergent form, in particular descendants which possess the essential characteristics of the identified strains. Upon continued propagation, the strains may acquire mutations most of which will not alter the properties of these strains significantly.

The isolates of the invention may also be further modified to impart further desirable properties to them. This may be achieved by classical propagation and selection techniques, like continued propagation in suitable host cells to extend the attenuated phenotype. Alternatively, the isolates may be genetically modified by directed mutation of the nucleic acid sequence of the genome of these strains by suitable genetic engineering techniques.

Recombinant techniques for preparing modified sequences are well known to those of skill in the art and usually employ construction of a full-length complementary DNA copies (infectious clones) of the viral genome which may then be modified by DNA recombination and manipulation methods (e.g., like site-directed mutagenesis, etc.). This way, for example, antigenic sites or enzymatic properties of viral proteins may be modified.

Preferably, the invention embraces pestivirus nucleic acid sequences that share at least 95% sequence homology with the sequence of SEQ ID NO:1 or SEQ ID NO:2 as such viruses may likely be effective at conferring immunity upon animals vaccinated with attenuated viruses containing such homologous sequences. The sequence shown in SEQ ID NO:1 or 2 is the full length sequence of the attenuated pestivirus and has a full length sequence of approximately 11,550 bases.

The pestivirus strains of the present invention are suitable for vaccines of the invention can be grown and harvested by methods known in the art, e.g., by propagating in suitable host cells.

In particular, the vaccine, as mentioned herein, is a live vaccine and/or a modified live vaccine-attenuated vaccine. The strains of the pestivirus according to the invention can be grown and harvested by methods known in the art, e.g., by propagating in suitable cells. Modified live vaccines (MLV) are typically formulated to allow administration of $10^1$ to $10^7$ viral particles per dose, preferably $10^3$ to $10^6$ particles per dose, and more preferably $10^4$ to $10^6$ particles per dose (4.0-6.0 $\log_{10}$ $TCID_{50}$).

An embodiment of the invention includes a method of producing a pestivirus vaccine comprising: (a) inoculating cells with the pestivirus; (b) incubating the inoculated cells; (c) harvesting pestivirus from the incubated cells. In a preferred embodiment, the method comprises a pestivirus comprising a sequence that is encoded by or comprises the sequence of SEQ ID NO:1 or 2; a sequence that is at least 99% identical with the SEQ ID NO:1 or 2; a protein that is encoded by nucleic acid sequences of SEQ ID NO:1; and/or a polyprotein that is encoded by a nucleic acid sequence that is at least 90% identical with the SEQ ID NO:2. The method can further comprise adding an adjuvant to the pestivirus vaccine, preferably, the adjuvant is an EMULSIGEN® oil-in-water emulsion-based adjuvant.

Another embodiment of the invention includes a method of producing a recombinant vaccine comprising: expressing the one or more antigens of pestivirus in a host cell; and harvesting the one or more antigens of pestivirus cells. In one such embodiment the method can include one or more antigens comprising an isolated nucleic acid encoding an antigen of pestivirus protein, wherein the recombinant pestivirus polypeptide has at least 90% homology with SEQ ID NO:1 or 2; a vector comprising the isolated nucleic acid of a); the recombinant pestivirus protein encoded by the nucleic acid of a); and any combination thereof. In one exemplary embodiment, one or more antigens of pestivirus are expressed by a recombinant baculovirus vector. The method can include one or more antigens of pestivirus expressed in insect cells. One embodiment further comprises the addition of an adjuvant to the pestivirus vaccine, preferably wherein the adjuvant is an EMULSIGEN® oil-in-water emulsion-based adjuvant.

Antibodies, or binding portions thereof, resulting from the use of pestivirus peptides of the present invention are useful for detecting in a sample the presence of pestivirus. This detection method comprises the steps of providing an isolated antibody or binding portion thereof raised against an pestivirus peptide of the invention, adding to the isolated antibody or binding portion thereof a sample suspected of containing a quantity of pestivirus and detecting the presence of a complex comprising the isolated antibody or binding portion thereof bound to pestivirus.

The antibodies or binding portions thereof of the present invention are also useful for detecting in a sample the presence of a pestivirus peptide. This detection method comprises the steps of providing an isolated antibody or binding portion thereof raised against a pestivirus peptide, adding to the isolated antibody or binding portion thereof a sample suspected of containing a quantity of the pestivirus peptide, and detecting the presence of a complex comprising the isolated antibody or binding portion thereof bound to the pestivirus peptide.

Immunoglobulins, particularly antibodies, (and functionally active fragments thereof) that bind a specific molecule that is a member of a binding pair may be used as diagnostics and prognostics, as described herein. In various embodiments, the present invention provides the measurement of a member of the binding pair, and the uses of such measurements in clinical applications. The immunoglobulins in the present invention may be used, for example, in the detection of an antigen in a biological sample whereby subjects may be tested for aberrant levels of the molecule to which the immunoglobulin binds, and/or for the presence of abnormal forms of such molecules. By "aberrant levels" is meant increased or decreased relative to that present, or a standard level representing that present, in an analogous sample from a portion of the body or from a subject not having the disease. The antibodies of this invention may also be included as a reagent in a kit for use in a diagnostic or prognostic technique.

In one aspect, an antibody of the invention that immunospecifically binds to a pestivirus peptide may be used to diagnose, prognose or screen for a pestivirus infection.

In another aspect, the invention provides a method of diagnosing or screening for the presence of a pestivirus infection or immunity thereto, comprising measuring in a subject the level of immunospecific binding of an antibody to a sample derived from the subject, in which the antibody immunospecifically binds a pestivirus peptide in which an increase in the level of said immunospecific binding, relative to the level of said immunospecific binding in an analogous sample from a subject not having the infectious disease agent, indicates the presence of pestivirus.

Examples of suitable assays to detect the presence of pestivirus peptides or antagonists thereof include but are not limited to ELISA, radioimmunoassay, gel-diffusion precipitation reaction assay, immunodiffusion assay, agglutination assay, fluorescent immunoassay, protein A immunoassay, or immunoelectrophoresis assay.

Immunoassays for the particular molecule will typically comprise incubating a sample, such as a biological fluid, a tissue extract, freshly harvested cells, or lysates of cultured cells, in the presence of a detectably labeled antibody and detecting the bound antibody by any of a number of techniques well-known in the art.

The binding activity of a given antibody may be determined according to well-known methods. Those skilled in the art will be able to determine operative and optimal assay conditions for each determination by employing routine experimentation.

An additional aspect of the present invention relates to diagnostic kits for the detection or measurement of pestivirus. Kits for diagnostic use are provided, that comprise in one or more containers an anti-pestivirus peptide antibody, and, optionally, a labeled binding partner to the antibody. Alternatively, the anti-pestivirus peptide antibody can be labeled (with a detectable marker, e.g., a chemiluminescent, enzymatic, fluorescent, or radioactive moiety). Accordingly, the present invention provides a diagnostic kit comprising, an anti-pestivirus peptide antibody and a control immunoglobulin. In a specific embodiment, one of the foregoing compounds of the container can be detectably labeled. A kit can optionally further comprise in a container a predetermined amount of a pestivirus peptide recognized by the antibody of the kit, for use as a standard or control.

Yet another embodiment of the invention includes a kit for vaccinating a pregnant sow or gilt against diseases associated with pestivirus comprising: a dispenser capable of administering a vaccine to a pregnant sow or gilt; and a pestivirus vaccine as described herein.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to a mammal, especially a pig. Associated with such container(s) can be a notice in the form prescribed by a governmental agency regulating the manufacture, use or sale of pharmaceuticals or biological products, which notice reflects approval by the agency of manufacture, use or sale for human administration.

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

The practice of the present invention will employ, unless otherwise indicated, conventional techniques of molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

It is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an", and "the" include plural referents unless the content clearly dictates otherwise. Thus, for example, reference to "an antigen" includes a mixture of two or more antigens, reference to "an excipient" includes mixtures of two or more excipients, and the like.

An "immunogenic or immunological composition or vaccine", all used interchangeably in this application, refers to a composition of matter that comprises at least one pestivirus of the present invention, or immunogenic portion thereof, that elicits an immunological response in the host of a cellular or antibody-mediated immune response to the composition. In a preferred embodiment of the present invention, an immunogenic composition induces an immune response and, more preferably, confers protective immunity against one or more of the clinical signs of a CT infection.

An "immunogenic" or "antigen" as used herein refer to a polypeptide or protein that elicits an immunological response as described herein. This includes cellular and/or humoral immune responses. Depending on the intended function of the composition, one or more antigens may be included be included. An "immunogenic" pestivirus protein or polypeptide includes the full-length sequence of any of the pestiviruses identified herein or analogs or immunogenic fragments thereof. The term "immunogenic fragment" or "immunogenic portion", used interchangeably in the application, refers to a fragment or truncated and/or substituted form of a pestivirus that includes one or more epitopes and thus elicits the immunological response described herein. In general, such truncated and/or substituted forms, or fragments will comprise at least six contiguous amino acids from the full-length pestivirus protein. More preferably, the truncated or substituted forms, or fragments will have at least 10, more preferably at least 15, and still more preferably at least 19 contiguous amino acids from the full-length pestivirus protein. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, June 28-Jul. 3, 1998. (The teachings and content of which are all incorporated by reference herein.)

The term "vaccine" as used herein refers to a pharmaceutical composition comprising at least one immunologically active component that induces an immunological response in an animal and possibly but not necessarily one or more additional components that enhance the immunological activity of the active component. A vaccine may additionally comprise further components typical to pharmaceutical compositions. By way of distinction the immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of the organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian, or other species plus optionally subsequent isolation and purification procedures, or by induction of the synthetic processes in the animal needing a vaccine by direct incorporation of genetic material using suitable pharmaceutical compositions (polynucleotide vaccination). A vaccine may comprise one or simultaneously more than one of the elements described above. The term "vaccine" as understood herein is a modified live, attenuated vaccine for veterinary use comprising antigenic substances and is administered for the purpose of inducing a specific and active immunity against a disease provoked by a pestivirus infection, The inactivated or attenuated pestivirus, in particular the inactivated or modified live, attenuated pestivirus as described herein, confer active immunity that may be transferred passively via maternal antibodies against the immunogens it contains and sometimes also against antigenically related organisms.

As used herein, the terms "inactivated" or "killed" are used synonymously. Various physical and chemical methods of inactivation are known in the art. The term "inactivated" refers to a previously virulent or non-virulent virus or bacterium that has been irradiated (ultraviolet (UV), X-ray, electron beam or gamma radiation), heated, or chemically treated to inactivate, kill, while retaining its immunogenicity. In one embodiment, the inactivated virus disclosed herein is inactivated by treatment with an inactivating agent.

Suitable inactivating agents include beta-propiolactone, binary or beta- or acetyl-ethyleneimine, glutaraldehyde, ozone, and formalin (formaldehyde).

For inactivation by formalin or formaldehyde, formaldehyde is typically mixed with water and methyl alcohol to create formalin. The addition of methyl alcohol prevents degradation or cross reaction during the in activation process. One embodiment uses about 0.1 to 1% of a 37% solution of formaldehyde to inactivate the virus or bacterium. It is critical to adjust the amount of formalin to ensure that the material is inactivated but not so much that side effects from a high dosage occur.

A more preferred inactivation method is the use of ethylenimine and related derivatives, such as binary ethylenimine (BEI) and acetylethylenimine, are examples of suitable chemical inactivating agents for use in inactivating the pestivirus virus. Other chemical inactivating agents, e.g., beta-propiolactone, aldehydes (such as formaldehyde), and/or detergents (e.g., TWEEN® detergent, TRITON® X, or alkyl trimethylammonium salts) can also be used to inactivate the virus. The inactivation can be performed using standard methods known to those of skill in the art. Samples can be taken at periodic time intervals and assayed for residual live virus. Monitoring of cytopathic effect on an appropriate cell line and/or fluorescent staining with an appropriate specific monoclonal or polyclonal antibody can be used to detect the presence of residual live virus. Alternatively, growth monitored by quantitative real-time PCR in serial passage can be utilized to determine presence of residual infectious virus.

Inactivation with BEI can be accomplished by combining a stock BEI solution (e.g., a solution formed by adding 0.1-0.2 M 2-bromo-ethylamine hydrobromide to 0.1-0.2 N aqueous NaOH) with viral fluids to a final concentration of about 1-5 mM BEI. Inactivation is commonly performed by holding the BEI-virus mixture at 35-40° C. (e.g., 37° C.) with constant mixing for about 24-72 hours. Virus inactivation can be halted by the addition of sodium thiosulfate solution to a final concentration in excess of the BEI concentration (e.g., addition of sodium thiosulfate at 17% of the volume of BEI to neutralize excess BEI) followed by mixing.

More particularly, the term "inactivated" in the context of a virus means that the virus is incapable of replication in vivo or in vitro and, respectively, the term "inactivated" in the context of a virus means that the virus is incapable of reproduction in vivo or in vitro. For example, the term "inactivated" may refer to a virus that has been propagated in vitro, e.g., in vitro, and has then deactivated using chemical or physical means so that it is no longer capable of replicating. In another example, the term "inactivated" may refer to a virus that has been propagated, and then deactivated using chemical or physical means resulting in a suspension of the virus, fragments or components of the virus, such as resulting in a solution which may be used as a component of a vaccine.

The term "live vaccine" refers to a vaccine comprising a living, in particular, a living viral active component.

A "subunit vaccine" can include antigens that best stimulate the immune system. In some cases, these vaccines use the Npro, capsid, Ems, E1, E2, NS2-3, helicase, NS4B, NS5A, and/or RNA-dependent RNA polymerase (RdRp) proteins of the pestivirus or epitopes from those proteins. Because subunit vaccines contain only the essential antigens and not all the other molecules that make up the pestivirus, the chances of adverse reactions to the vaccine are lower.

Subunit vaccines can contain anywhere from one to 10 or more antigens, e.g., 2, 3, 4, 5, 6, 7, 8, or 9 antigens. Skilled practitioners will appreciate how to make subunit vaccines. For example, the antigen molecules can be expressed using recombinant DNA technology. Vaccines produced this way are called "recombinant subunit vaccines."

A "pharmaceutical composition" essentially consists of one or more ingredients capable of modifying physiological, e.g., immunological functions, of the organism it is administered to, or of organisms living in or on the organism. The term includes, but is not restricted to, antibiotics or antiparasitics, as well as other constituents commonly used to achieve certain other objectives such as, but not limited to, processing traits, sterility, stability, feasibility to administer the composition via enteral or parenteral routes such as oral, intranasal, intravenous, intramuscular, subcutaneous, intradermal, or other suitable route, tolerance after administration, or controlled release properties. One non-limiting example of such a pharmaceutical composition, solely given for demonstration purposes, could be prepared as follows: cell culture supernatant of an infected cell culture is mixed with a stabilizer (e.g., spermidine and/or bovine serum albumin (BSA)) and the mixture is subsequently lyophilized or dehydrated by other methods. Prior to vaccination, the mixture is then rehydrated in aqueous (e.g., saline, phosphate buffered saline (PBS)) or non-aqueous solutions (e.g., oil emulsion, aluminum-based adjuvant).

As used herein, "pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g., anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John Wiley and Sons, NY, pp. 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g., vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid (EDTA), among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Attenuation" means reducing the virulence of a pathogen. In the present invention, an attenuated virus is one in which the virulence has been reduced so that it does not cause clinical signs of a pestivirus infection but is capable of inducing an immune response in the target mammal, but may also mean that the clinical signs are reduced in incidence or severity in animals infected with the inactivated or attenuated pestivirus in comparison with a "control group" of animals infected with non-attenuated, wild type pestivirus and not receiving the inactivated or attenuated virus. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an inactivated, attenuated and/or avirulent pestivirus isolate is one that suitable for incorporation into an immunogenic composition comprising an inactivated or modified live pestivirus.

An "attenuated virus" is a viable ("live") virus, in which the virulence of the infectious agent has been reduced, e.g., though passaging the virus in a specific cell line, or through genetic manipulation of the viral genome. The attenuation of the virus pertains to its virulence (pathogenicity), but does not necessarily affect the replicative capability of a virus. An attenuated virus can still be capable of replication. Thus, it may be a strain of a virus whose pathogenicity has been reduced so that it will initiate the immune response without causing the specific disease. In the context of the present invention, an attenuated virus may be a pestivirus whose pathogenicity has been abrogated or reduced by inactivating at least one gene or protein involved in virulence. In the present invention "attenuation" is synonymous with "avirulent". In this context, the term "reduce/reduced" means a reduction in pathogenicity of at least 10%, preferably 25%, even more preferably 50%, still more preferably 60%, even more preferably 70%, still more preferably 80%, even more preferably 90% and most preferably of 100% as compared to a control group.

"Modified live" means the virus has been reduced in virulence by any of several methods known in the art such, including but not limited to repeated passage in cell culture; forced adaptation to growth at normally-restrictive temperatures; treatment with chemical mutagens to force high numbers of mutations and selection for the desired characteristics; and deletion or insertion of genes using rDNA technology. By the term "non-virulent" or "avirulent" is meant the modified live virus exhibits reduced or no clinical signs of infection when administered.

"Virulent" refers to the ability of a pestivirus isolate to cause disease associated with pestivirus. Virulence can be evaluated by observing disease progression in the animal. An example of a "virulent" strain of pestivirus is that exemplified by the challenge strain, as described and used in the present invention.

"Avirulent" refers to isolates of pestivirus that are lacking in virulence. That is, avirulent strains, isolates, or constructs are non-pathogenic and are incapable of causing disease. As used herein the term "avirulent" is used synonymously with the term "non-virulent."

As used herein the terms "strain" or "isolate" are used interchangeably.

The term "wild type pestivirus", as used herein, is in particular directed to an infectious pathogenic pestivirus, which is particularly capable of causing CT in swine and especially piglets. In one particular preferred embodiment, the term "wild type virus" is directed to a pestivirus whose genome comprises a RNA sequence or consists of a RNA polynucleotide, wherein said RNA sequence or RNA polynucleotide is a RNA copy of a polynucleotide comprising SEQ ID NO:1, 3, 5, 7, 9, 11, 13, 15, 17, 19, or 21. In some embodiments, a wild type pestivirus comprises an amino acid sequence comprising SEQ ID NO:2, 4, 6, 8, 10, 12, 14, 16, 18, 20, or 22.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Particularly, an effective amount refers to a titer measured in tissue culture infectious dose 50 or plaque forming units per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

The term "immunoreactive to pestivirus" as used herein means that the peptide or fragment elicits the immunological response against pestivirus.

The terms "sequence identity" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e., overlapping positions)×100). Preferably, the two sequences are the same length.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferred of 100, even more preferred of 250, even more preferred of 500 nucleotides.

A "conservative substitution" refers to the substitution of an amino acid residue with another amino acid residue having similar characteristics or properties including size, hydrophobicity, etc., such that the overall functionality does not change significantly.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package, using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 95%, e.g., at least 96%, 97%, 98%, 99%, or 100% "sequence identity" to a reference nucleotide sequence, it is intended that the nucleotide sequence of the given polynucleotide is identical to the reference sequence except that the given polynucleotide sequence may include up to 5, 4, 3, 2, 1, or 0 point mutations per each 100 nucleotides of the reference nucleotide sequence. In other words, in a polynucleotide having a nucleotide sequence having at least 95%, e.g., at least 96%, 97%, 98%, 99%, or 100% sequence identity relative to the reference nucleotide sequence, up to 5%, 4%, 3%, 2%, 1%, or 0% of the nucleotides in the reference sequence may be deleted or substituted with another nucleotide, or a number of nucleotides up to 5%, 4%, 3%, 2%, 1%, or 0% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 95%, e.g., at least 96%, 97%, 98%, 99%, or 100% sequence identity to a reference amino acid sequence, it is intended that the given amino acid sequence of the polypeptide is identical to the reference sequence except that the given polypeptide sequence may include up to 5, 4, 3, 2, 1, or 0 amino acid alterations per each 100 amino acids of the reference amino acid sequence. In other words, to obtain a given polypeptide sequence having at least 95%, e.g., at least 96%, 97%, 98%, 99%, or 100% sequence identity with a reference amino acid sequence, up to 5%, 4%, 3%, 2%, 1%, or 0% of the amino acid residues in the reference sequence may be deleted or substituted with another amino acid, or a number of amino acids up to 5%, 4%, 3%, 2%, 1%, or 0% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The term "mutation" in the context of the invention is understood as a change in a genomic sequence, in particular in the RNA sequence of a pestivirus. Since viruses that use RNA as their genetic material have rapid mutation rates, the term "mutation", as mentioned herein, is particularly directed to a genetically engineered change in a genomic sequence, such as by cloning, forced recombination, growth in the presence of mutagens or other techniques used to experimentally alter the genome, which in particular results in a virus growing to titers significantly lower than wild type pestivirus in the infected host, when propagated under the same conditions. Moreover, in another preferred embodiment the mutation described herein can also be caused by natural mutation and subsequent isolation of the pestivirus according to the invention, wherein said isolated virus includes the mutation described herein.

The protein sequences or nucleic acid sequences of the present invention can further be used as a "query sequence" to perform a search against public databases to, for example, to identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information The term "vector" as it is known in the art refers to a polynucleotide construct, typically a plasmid or a virus, used to transmit genetic material to a host cell. Vectors can be, for example, viruses, plasmids, cosmids, or phage. A vector as used herein can be composed of either DNA or RNA. In some embodiments, a vector is composed of DNA. An "expression vector" is a vector that is capable of directing the expression of a protein encoded by one or more genes carried by the vector when it is present in the appropriate environment. Vectors are preferably capable of autonomous replication. Typically, an expression vector comprises a transcription promoter, a gene, and a transcription terminator. Gene expression is usually placed under the control of a promoter, and a gene is said to be "operably linked to" the promoter.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

The term "construct," as used herein, refers to a recombinant nucleic acid that has been generated for the purpose of the expression of a specific nucleotide sequence(s), or that is to be used in the construction of other recombinant nucleotide sequences.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018; Paoletti, "Applications of pox virus vectors to vaccination: An update," Proc. Natl. Acad. Sci. USA 93: 11349-11353, October 1996; Moss, "Genetically engineered poxviruses for recombinant gene expression, vaccination, and safety," Proc. Natl. Acad. Sci. USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols"

(1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 406; EPA0 370 573; U.S. Pat. No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," Proc. Natl. Acad. Sci. USA 93:11307-11312, October 1996; Andreansky et al., "The application of genetically engineered herpes simplex viruses to the treatment of experimental brain tumors," Proc. Natl. Acad. Sci. USA 93: 11313-11318, October 1996; Robertson et al., "Epstein-Barr virus vectors for gene delivery to B lymphocytes", Proc. Natl. Acad. Sci. USA 93: 11334-11340, October 1996; Frolov et al., "Alphavirus-based expression vectors: Strategies and applications," Proc. Natl. Acad. Sci. USA 93: 11371-11377, 1996; Kitson et al., J. Virol. 65, 3068-3075, 1991; U.S. Pat. Nos. 5,591,439, 5,552,143; WO 98/00166; allowed U.S. application Ser. Nos. 08/675,556, and 08/675,566 both filed Jul. 3, 1996 (recombinant adenovirus); Grunhaus et al., 1992, "Adenovirus as cloning vectors," Seminars in Virology 3:237-52, 1993; Ballay et al. EMBO Journal 4:3861-65, Graham, Tibtech 8:85-87, 1990; Prevec et al., J. Gen Virol. 70:429-34; PCT WO 91/11525; Felgner et al. (1994), J. Biol. Chem. 269, 2550-2561, Science 259:1745-49, 1993; and McClements et al., "Immunization with DNA vaccines encoding glycoprotein D or glycoprotein B, alone or in combination, induces protective immunity in animal models of herpes simplex virus-2 disease", Proc. Natl. Acad. Sci. USA 93:11414-11420, 1996; and U.S. Pat. Nos. 5,591,639, 5,589,466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

As used herein, the terms "nucleic acid" and "polynucleotide" are interchangeable and refer to any nucleic acid. The terms "nucleic acid" and "polynucleotide" also specifically include nucleic acids composed of bases other than the five biologically occurring bases (adenine, guanine, thymine, cytosine and uracil).

The term "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements. Exemplary regulatory elements in prokaryotes include promoters, operator sequences and a ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the term "enhancer" refers to a type of regulatory element that can increase the efficiency of transcription, regardless of the distance or orientation of the enhancer relative to the start site of transcription.

Generation of a viral vector can be accomplished using any suitable genetic engineering techniques well known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)).

A viral vector can incorporate sequences from the genome of any known organism. The sequences can be incorporated in their native form or can be modified in any way to obtain a desired activity. For example, the sequences can comprise insertions, deletions or substitutions.

A viral vector can include coding regions for two or more proteins of interest. For example, the viral vector can include the coding region for a first protein of interest and the coding region for a second protein of interest. The first protein of interest and the second protein of interest can be the same or different. In some embodiments, the viral vector can include the coding region(s) for a third or a fourth protein of interest. The third and the fourth protein of interest can be the same or different. The total length of the two or more proteins of interest encoded by one viral vector can vary. For example, the total length of the two or more proteins can be at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer.

Preferred viral vectors include baculovirus such as BaculoGold (BD Biosciences Pharmingen, San Diego, Calif.), in particular provided that the production cells are insect cells. Although the baculovirus expression system is preferred, it is understood by those of skill in the art that other expression systems will work for purposes of the present invention, namely the expression of E or Erns into the supernatant of a cell culture. Such other expression systems may require the use of a signal sequence in order to cause E or Erns expression into the media.

The term "genogroup" as it is known in the art refers to related viruses within a genus; which may be further subdivided into genetic clusters. Identified genogroups of the pestivirus genus include border disease virus, bovine diarrhea virus-1 (BVD-1), BVD-2, classical swine fever virus and other unclassified pestiviruses.

The term "clade" as it is known in the art refers to a group consisting of an ancestor and all its descendants, a single "branch" in a phylogenetic tree. The ancestor may be, as an example an individual, a population or a species. A genogroup can include multiple clades.

An "immune response" or "immunological response" means, but is not limited to, the development of a cellular and/or antibody-mediated immune response to the composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

Herein, "specifically immunoreactive" refers to an immunoreactive protein or polypeptide that recognizes an antigen characteristic of pestivirus or CT infection but does not react with an antigen characteristic of a strict challenge control.

"Protection against disease", "protective immunity", "functional immunity" and similar phrases, means a response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection are lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of CT. Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent, preferably a pestivirus generated CT, respectively, in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge the infectious agent.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

As used herein, the term "viremia" is particularly understood as a condition in which pestivirus particles reproduce and circulate in the bloodstream of an animal, in particular of a piglet.

The term "reduction of viremia" induced by pestivirus means, but is not limited to, the reduction of pestivirus entering the bloodstream of an animal, wherein the viremia level, i.e., the number of pestivirus copies per mL of blood serum or the number of plaque forming colonies per deciliter of serum, is reduced in the serum of subjects receiving the composition of the present invention by at least 50% in comparison to subjects not receiving the composition and may become infected. More preferably, the viremia level is reduced in subjects receiving the composition of the present invention by at least 90%, preferably by at least 99.9%, more preferably by at least 99.99%, and even more preferably by at least 99.999%.

"Safety" refers to the absence of adverse consequences in a vaccinated animal following vaccination, including but not limited to: potential reversion of a bacterium-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—, an immune response in the animal against pestivirus or CT.

"Mortality", in the context of the present invention, refers to death caused by pestivirus infection or CT, and includes the situation where the infection is so severe that an animal is euthanized to prevent suffering and provide a humane ending to its life.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice.

However, those of skill in the art should, in light of the present disclosure, appreciate that many changes can be made in the specific embodiments which are disclosed and still obtain a like or similar result without departing from the spirit and scope of the invention.

EXAMPLES

Example 1

The purpose of this study was to determine if clinical disease could be reproduced in cesarean-derived-colostrum deprived (CDCD) pigs using a tissue homogenate containing the novel pestivirus of the present invention. Specifically, the purpose is to reproduce viremia and tissue colonization (as detected by qRT-PCR) in CDCD piglets following challenge with serum containing a novel pestivirus.

Animal Care

The pigs were housed at the animal facilities at VRI at Cambridge, Iowa for the duration of the study. Pigs were fed a commercial ration (UltraCare Medicated, lot #4 Jun. 2016) that was appropriate for their size, age and condition according to acceptable animal husbandry practices for the region (antibiotics were included). Water was available ad libitum. Floor and feeder space met or exceeded requirements set forth in the Consortium "Guide for the Care and Use of Agricultural Animals in Agricultural Research and Teaching", third edition, January 2010.

Any moribund animal and animals unwilling to eat or drink were euthanized before the necropsy date at the discretion of the Investigator. Any animal that died or was euthanized throughout the study period were necropsied by a veterinarian. All animals were euthanized at the termination of the study, accounted for, and disposed of by incineration.

Experimental Design

Figure 4:
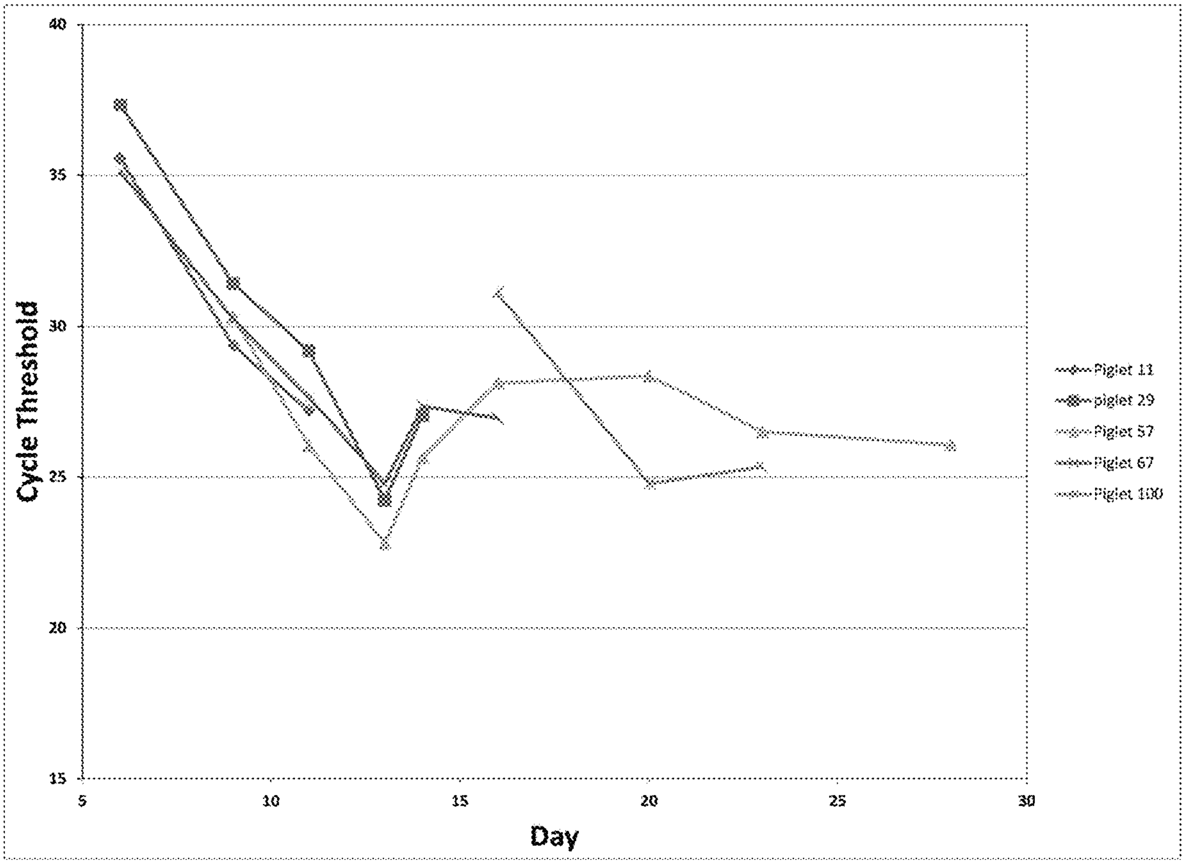
FIG. 4 shows the cycle of viremia in the piglets tested in Example 1.

A total of ten CDCD pigs were used for this bioassay. Pigs were randomized into two groups. Group 1 animals (n=6) were challenged by three routes (intracranial, intranasal and intravenously) with serum containing pestivirus. Group 2 animals (n=4) were inoculated in a similar manner with placebo material and served as negative controls. The animals in each group were maintained in separate rooms. Following challenge, pigs were monitored daily for clinical signs from days post challenge (D0) through D28. Rectal temperatures were taken twice weekly throughout the study. Serum, fecal and nasal samples were collected twice weekly throughout the study. Samples were screened for pestivirus RNA. The animals' weights were taken on D0 and the time of necropsy to assess the impact of challenge on average daily gain. One animal from the challenge group was necropsied on D10, 14, 17, 21, 24 and 28. The decision on which animal would be necropsied was based on detection of pestivirus RNA in serum. One animal from the placebo group was euthanized on D17, 21, 24 and 28. Tissues and terminal sera collected at the time of necropsy were screened for the presence of Pestivirus RNA by qRT-PCR (FIG. 4).

Serum from NAC #20140530, animal ID no. 21-24, lot #2815-105-2 through 2815-105-5 were thawed at 37° C. and pooled. Pooled sera was 0.2 μm filtered and diluted by adding 6 mL of sera to 29 mL of 1× phosphate buffered saline (Gibco cat #10010-023, L #1535358). The prepared material was assigned L #2815-171-A and was stored at −70° C.±10° C. until use (FreezerWorks id #466528). On the day of challenge, material was thawed and held on ice during the challenge period. Three 2 mL aliquots were stored as retention samples at −70° C.±10° C. (FreezerWorks id #466044). Pooled material was retained but not further tested.

TABLE 1

Schedule of key events where DPC refers to day post challenge

| Study Day | Study Event |
|---|---|
| D 0<br>(5 Aug. 2014) | Pigs challenged<br>Collection of serum, nasal and fecal samples prior to challenge<br>Weight measurement prior to challenge |
| D 2, 6, 9, 13, 16, 20, 23, 27 | Collection of serum, nasal and fecal samples<br>Rectal temperatures |
| D 10 | Collection of serum from all available animals |
| D 10, 14, 17, 21, 24, 28 | Necropsy of 1 animal per day for challenge group<br>Terminal blood collection<br>Weight measurement |
| D 17, 21, 24, 28 | Necropsy of 1 animal per day for placebo group<br>Terminal blood collection<br>Weight measurement |
| D 0-28 | Daily clinical observations |
| TBD | Piglets arrive at VRI<br>Evaluation of piglets |
| DPC 0 | Piglets challenged<br>Collection of serum, nasal and fecal samples prior to challenge<br>Weight measurement prior to challenge |
| DPC 1, 3, 5, 7 | Collection of serum, nasal and fecal samples<br>Rectal temperatures<br>Photograph or video if clinical signs occur |
| DPC 8-28 | Collection of serum, nasal and fecal samples twice a week<br>Rectal temperatures twice a week |
| DPC 0-28 | Daily clinical observations |
| DPC 3, 7, 10, 14, 21, 28 | Necropsy<br>Terminal blood collection<br>Weight measurement |

Challenge

Intranasal Challenge:

On DPC0, the Investigator administered 2 ml of challenge material, 1 ml per nares using a sterile syringe. This was administered prior to anesthetizing the animal.

Intracranial Challenge:

On DPC0, the Investigator anesthetized animals with a mixture of Ketamine, Xylazine, and Telazol. The calvarium was cleaned and disinfected. A biopsy punch (Miltex Instrument Company, Inc.) was be used to remove a 4 mm section of skin from the calvarium. A hole was trephined through the calvarium using a hand held power drill. The challenge material was injected into the cerebrum using a 20-gauge, 1.88 inch-long catheter (BD AngioCath part no. H3272). Following injection of the inoculum, 0.5 ml of 1×PBS was inserted into the catheter to ensure delivery of the inoculum. The skin incision was closed with a single suture.

Intravenous Challenge:

While the piglets were anesthetized, 2 ml of challenge material was slowly administered into the auricular vein using a sterile butterfly catheter and syringe.

Clinical Observations

After challenge, piglets were monitored once daily for the presence of clinical signs. As it is unknown whether clinical signs would be similar to other swine pestiviruses (e.g., Classical swine fever, Bungowannah virus) piglets were monitored for signs of systemic infection as well as neurological signs.

Fecal Sample Collection

Fecal material was collected from piglets by the Investigator. Samples were a swab (Fisher catalog no. 23-400-111) placed into a falcon tube. Samples were collected from the animal and not the floor. The material was transferred on the day of collection and samples were held at 2-8° C. if tested <24 hours after delivery or held at −70° C.±10° C. if tested at a later date.

Nasal Sample Collection

Nasal swabs were collected from piglets by the Investigator. Samples were a swab (Fisher catalog no. 23-400-111) placed into a falcon tube. Samples were collected from the animal by swabbing both nares. Samples were labeled with a minimum of study number, day of study, and animal ID. The material was transferred on the day of collection and samples were held at 2-8° C. if tested <24 hours after delivery or held at −70° C.±10° C. if tested at a later date.

Blood Collection

On blood collection dates, four to 15 mL of venous whole blood were collected by the Investigator via the anterior vena cava from each pig using a sterile 18-20 g×1 inch (2.54 cm) to 1.5 inch (3.81 cm) VACCUTAINER® needle, a VACCUTAINER® needle holder and 9 or 13 mL serum separator tubes (SST). The serum was separated from the clot by centrifugation and decanted into a screw-cap cryogenic vial. The material was transferred on the day of collection and samples were held at 2-8° C. if tested <24 hours after delivery or held at −70° C.±10° C. if tested at a later date.

Necropsy

General Overview:

Any moribund animals were bled, humanely euthanized, then necropsied by a veterinarian. Pigs were selected for necropsy based on viremia data (a Ct value <30) generated the day prior to the scheduled necropsy. Piglets were weighed at the time of necropsy and macroscopic lesions were recorded.

Terminal Blood Collection and Processing:

The piglets were deeply anesthetized prior to blood collection. Blood (approximately 5% of body weight) was collected into sterile jars, bottles or multiple SST tubes and was allowed to clot at room temperature. The serum was separated from the clot by centrifugation and decanted into sterile bottles. Serum samples were held at 2-8° C. if tested <24 hours after delivery or held at −70° C. if tested at a later date.

Sample Collection:

The Investigator collected formalin-fixed tissue samples of cerebrum (½ of the organ), cerebellum (½ of organ), brainstem (½ of organ), spinal cord (6 sections), bone marrow (collect a section of long bone), tonsil (1 section), lung (1 section of accessory lobe or area with lesion), heart (2 sections), spleen (1 section), kidney (1 section), liver (1 section), lymph node (tracheobronchial and mesenteric), small intestine (3 sections ileum), large intestine (3 section). A one inch section of lung and one to two inch sections of intestine are recommended such that a 1:10 ratio of fixed tissue to formalin is maintained. All fixed tissues were placed into one container containing 10% buffered formalin solution. For each piglet, and a replicate sample of sections listed above were collected into separate whirl pack bags.

Tissue Processing:

Samples were transported on the day of collection and samples were held at 2-8° C. if tested <24 hours after delivery or held at −70° C. if tested at a later date. The fixed tissues were maintained at room temperature.

Weight Measurement

Weight measurements were taken on piglets on DPC0 the day of necropsy. Weights were taken on a calibrated scale and recorded on an appropriate form provided by the animal facility. Weights were used to calculate an average daily gain.

Sample Testing

Pestivirus PCR was performed on all samples. Selected samples were screened for enterovirus, porcine calicivirus, transmissible gastroenteritis virus, *Escherichia coli, Salmonella*, and/or *Clostridium* sp. or other infectious agents.

Example 2

The objectives of this project were to 1) detect potential pathogen(s) in samples from piglets with congenital tremors and 2) develop an infection model to reproduce disease. Using next-generation sequencing, a divergent lineage pestivirus was detected in piglets with congenital tremors. The virus was originally most closely related to a bat pestivirus but is now more closely related to a recently published novel porcine pestivirus provisionally named atypical porcine pestivirus. A quantitative real-time PCR detected the virus in samples from neonatal piglets with congenital tremors from two separate farms, but not in samples from unaffected piglets from the same farm. To fulfill the second objective, pregnant sows were inoculated with either serum containing the pestivirus or PBS (control) by intravenous and intranasal routes simultaneously with direct inoculation of fetal amniotic vesicles by ultrasound-guided surgical technique. Inoculations were performed at either 45 or 62 days of gestation. All sows inoculated with the novel pestivirus farrowed piglets affected with congenital tremors while PBS-inoculated control piglets were unaffected. Tremor severity for each piglet was scored from videos taken 0, 1 and 2 days post-farrowing. Tremor severity remained relatively constant from 0 to 2 days post-farrowing for a majority of piglets. The prevalence of congenital tremors in pestivirus-inoculated litters ranged from 57% (4 out of 7 affected piglets) to 100% (10 out of 10 affected piglets). The virus was consistently detected by PCR in tissues from piglets with congenital tremors but was not detected in control piglets. Samples positive by PCR in greater than 90% of piglets sampled included brainstem (37 out of 41), mesenteric lymph node (37 out of 41), tracheobronchial lymph node (37 out of 41), and whole blood (19 out of 20). Although the first description of congenital tremors was in 1922, this is the first reported reproduction of congenital tremors following experimental inoculation with a divergent lineage porcine pestivirus. Studies investigating disease mechanism, epidemiology, and diagnostic assay development are needed to better understand the pathophysiology of congenital tremors due to this pestivirus.

Next-Generation Sequencing

Varied porcine tissues (serum, cerebrum, cerebellum, spinal cord, cerebrospinal fluid (CSF), and/or lung) from three diagnostic investigations of CT were obtained: lung tissue from a single piglet (ID 20130103); either pooled brain tissue or pooled lung tissue from six piglets (ID 20120705); and CSF (n=2; Farm B), serum (n=2; Farm A and B), and lung (n=2; Farm A and B) from six different piglets originating from two different farms (ID 2014016573). With the exception of the lung tissue from sample ID 20120705, all samples tested exhibited at least partial pestivirus genomic sequence. Serum or tissue homogenates were re-suspended in Hanks balanced salt solution (Corning-Cellgro) and enriched for viral particle protected nucleic acids by digestion with a combination of nucleases: RNase A (Invitrogen), Baseline Zero DNase (Epicentre), and Turbo DNase (Invitrogen). Viral nucleic acids were extracted per the manufacturer's protocol using Qiagen Viral RNA blood kit. Post-extraction, nucleic acids were further treated with Turbo DNase to remove host or potential viral DNA, thus further enriching for viral RNA. Double-stranded cDNA was generated through reverse transcription and Klenow (NEB) treatment using priming with random hexamers.

Samples were processed for MiSeq based sequencing through library generation using the NextEra XT library preparation kit (Illumina) per the manufacturer's suggested protocol, with replacement of column elution (Qiagen, MinElute) in lieu of bead normalization. The library was run on the MiSeq using the 500-cycle kit (Illumina) and data was analyzed using a combination of NextGene (version 2.3.4.2) and Sequencher software (version 5.1). High quality sequences were selected as those containing a median Q-score of greater than 25 and trimmed with a cut-off of no more than 3 uncalled bases at 3'-end or 3-consecutive bases with Q-score measuring less than 16. De novo assembled sequences were analyzed by comparison to GenBank sequence via BLASTn and BLASTx. ClustalW alignment was used for phylogenetic analysis of the 215 amino acid sequence of the NS3 gene and 170 amino acid sequence of the Npro gene. Neighbor-joining phylogenetic trees were generated from 1,000 replicates using MEGA 6.0 software.

Quantitative Real-Time Polymerase Chain Reaction (RT-qPCR)

A RT-qPCR targeting the N3 S region of the genome of the divergent lineage pestivirus was designed. Tissues samples (n=362) from growing pigs that were submitted to the Iowa State University Veterinary Diagnostic Laboratory (ISU VDL) for routine diagnostic testing were used to determine the frequency of the pestivirus in this sample set. Two sample sets were also collected from farms with congenital tremors. These samples included serum, cerebrum, cerebellum, brainstem, and spinal cord. The first set (Farm A) consisted of 6 affected and 2 unaffected pre-suckle piglets, serum from five sows from which the pre-suckle piglets were selected, and 5 affected and 2 unaffected post-suckle piglets between 6- and 14-days-old. The second set (Farm B: ISUVDL2014016573) consisted of 5 affected piglets suckle status unknown and serum from five sows with affected piglets.

The quantitative one-step RT-PCR kit (iTaq Universal Probes One-Step Kit; BioRad, cat no. 172-5141) was carried out in a 25 μl reaction containing 2 μl of extracted total nucleic acid, 1.0 μl of probe (2 μM), 1 μl of each primer (5 μM), 12.5 μl of 2×RT-PCR mix, 0.5 μl iScript reverse transcriptase and 7.0 μl of DEPC-treated water (Table 2). The reaction took place using a CFX96 real-time PCR detection system (BioRad) under the following conditions: initial reverse transcription at 50° C. for 10 min, followed by initial denaturation at 95° C. for 3 min, 40 cycles of denaturation at 95° C. for 15 s and annealing and extension at 57° C. for 30 s. To generate quantitative data, a pestivirus ultramer was included in each run (Integrated DNA Technologies) encompassing the NS3 region targeted by the primers. A cut-off for positive samples was established at cycle quantification (Cq) values lower than 36.

TABLE 2

Real-time PCR Primer, Probe and Ultramer Sequences

| | Sequence |
|---|---|
| Pesti_6332_F | TGC CTG GTA TTC GTG GC (SEQ ID NO: 23) |
| Pesti_6455_R | TCA TCC CAT GTT CCA GAG T (SEQ ID NO: 24) |
| Pesti_6351_P | /5Cy5/CCT CCG TCT CCG CGG CTT TGG/3BHQ_2/ (SEQ ID NO: 25) |
| Pesti_ultra | AAC AGG AAA GAA CTG CCT GGT ATT CGT GGC AAC CAA AGA AGC CGC GGA GAC GGA GGC TAA AGA ACT GCG CAC CAG AGG AAT TAA CGC CAC CTA TTC AGG TAT AGA CCC TAA GAC TCT GGA ACA TGG GAT GAC CAA TCA GCC AT (SEQ ID NO: 26) |

Sow Inoculation Model

Animals

All procedures were approved by the Institutional Animal Care and Use Committee of Iowa State University (Log Number: 1-14-7907-S 2). Eight individually identified crossbred sows at 38 days of gestation were obtained from a commercial source with no known previous history of CT. Serum from all sows was negative for PCV2a, PCV2b, PRRSV, PPV1, PPV5 and the novel pestivirus by RT-qPCR prior to shipment and inoculation. Individual sows were randomly assigned to one of three groups housed separately [sham-inoculated at 45 days gestation (n=1) and 62 days gestation (n=1), pestivirus-inoculated at 45 days gestations (n=3), and pestivirus-inoculated at 62 days gestation (n=3)] and were fed a nutritionally complete diet throughout the study period.

Animal Inoculation

Sows were held off feed and water for 12 hours prior to surgery to reduce the risk of anesthetic regurgitation. Terminal serum from a viremic pig (ISUVDL2014016573) was thawed at 37° C. Total nucleic acid was extracted and screened by PCR for the presence of PCV2a, PCV2b, PRRSV, PPV1, PPV5 and the pestivirus; only the pestivirus was detected (Cq=27.47). Serum was 0.2 μm filtered and diluted by adding 6 mL of sera to 35 mL of 1×PBS (Gibco). On the day of inoculation, inoculum was thawed and held on ice during the inoculation procedure. General anesthesia was induced with an intramuscular injection of a combination of tiletamine and zolazepam (TELAZOL®), ketamine, and xylazine. Following anesthetic induction, each sow was placed in left lateral recumbency, and the right abdomen prepared for aseptic laparotomy. The abdomen was draped for surgery and a local line block with 2% lidocaine was administered prior to incision. An approximately 30 cm paramedian incision was made ~5 cm lateral to the mammary tissue to gain access to the abdominal cavity. The uterus was exteriorized and a sterile handheld linear array ultrasound transducer was used to image each fetal unit and guide the inoculation needle into the fetal amniotic vesicle. Each vesicle was inoculated with 0.25 mL of inoculum (PBS or pestivirus-serum) using a small gauge needle (22 g) (S2 MP4). The abdominal wall was closed in three layers using size 2 polyglactin 910 suture. The inoculum was also administered directly to the sow via an intranasal (2 mL) and intravenous (2 mL) route immediately following the surgical procedure. Single doses of flunixin meglumine (BANAMINE-S®) and ceftiofur crystalline free acid (EXCEDE®) were given intramuscularly immediately after incisional closure and prior to anesthetic recovery. Anesthetic induction occurred at 8:30 AM for the first sow on the respective day of surgery. Each procedure took approximately 1 hr. The anesthetic induction of the final sow occurred at 11:30 AM.

Clinical Observations, Sample Collection, and Necropsy

After inoculation, sows were monitored daily and rectal temperatures were taken from 0-7 days post-inoculation (DPI). Fecal material, blood and nasal swabs were collected from sows at DPI 2, 7, 10 and 14 and then weekly until farrowing. At the time of farrowing, piglets were individually identified and serum, nasal swabs and fecal swabs were collected. In a subset of piglets (n=7), blood from the umbilical cord was collected. Videos of individual piglets were taken daily from 0-2 days post-farrowing (DPF). Four investigators blinded to groups reviewed the videos and each piglet received a tremor severity score: 0—absent, 1—fine muscle fasciculation, 2—mild tremor, 3—moderate tremor, 4—severe tremor with pronounced hopping. Scores were then averaged to assign each piglet an overall tremor severity score by DPF. Piglets receiving a score of ≥0.75 on DPF 2 were considered to be affected. The presence or absence of splay leg was also recorded on each DPF for each piglet. Sows and piglets were euthanized on DPF 2 via captive bolt gun and injectable barbiturate overdose, respectively. At necropsy piglet serum, cerebrum, cerebellum, brainstem, spinal cord, kidney, mesenteric lymph node, tracheobronchial lymph node, thymus, heart, and spleen were collected. In a subset of piglets, whole blood (EDTA tubes; n=20) and CSF (n=29) were collected. Sow serum was also collected at necropsy.

Pestivirus Identification

Next-Generation Sequencing

Figure 5A:
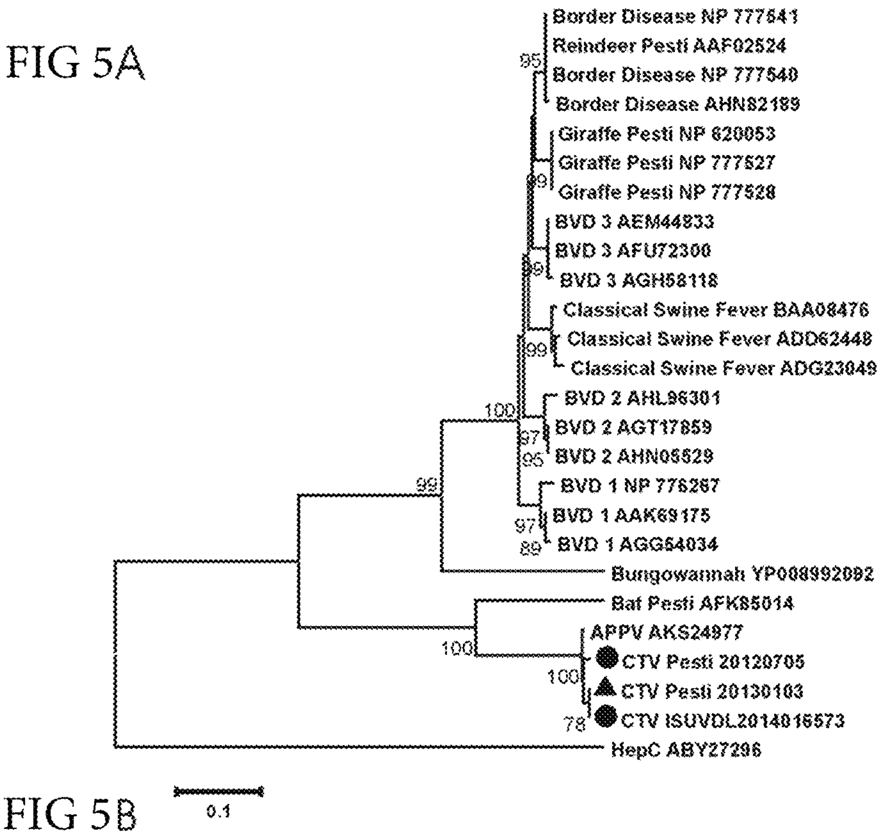
FIGS. 5A and 5B show the phylogenetic association of pestiviruses. Neighbor-joining phylogenetic trees generated with 1,000 bootstrap samplings (MEGA 6.0) for pestivirus NS3 (5A) and Npro (5B) amino acids aligned by ClustalW multiple alignment. GenBank accession numbers for each sample indicated in name. Circles indicate sequences described from this study and triangle indicates the sequence from the virus described in this study used for inoculation.
Figure 5B:
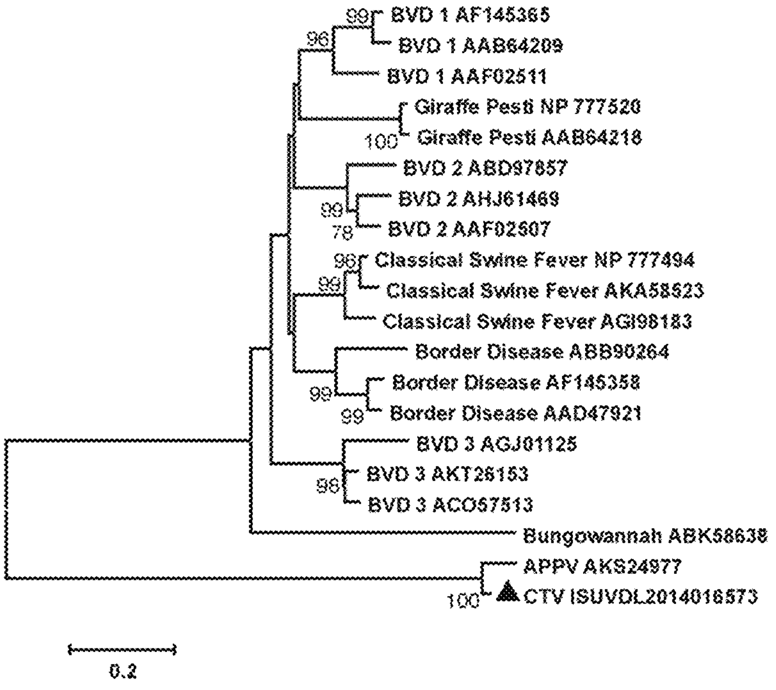

Through the use of next-generation sequence technology a virus closely related to a Chinese bat pestivirus, and now known to be more closely related to a recently reported provisionally named atypical porcine pestivirus was discovered from three independent congenital tremor disease investigations. The near-complete genome was obtained from one of the three investigations. This virus in the serum from a viremic animal was subsequently used for animal inoculations in this study. Phylogenetic analysis of the NS3 and Npro support classification of the virus identified herein as a member of the putative "atypical porcine pestivirus" species (FIG. 5), with 88.0% and 94.6% nucleotide and amino acid identity, respectively. A retrospective analysis of pestivirus RNA by RT-qPCR from cases submitted to the ISU VDL indicated 21 of 362 samples (6%) were positive. These cases were routine submissions from herds experiencing varied clinical signs.

RT-qPCR

Piglet samples from animals exhibiting congenital tremors and unaffected cohorts were collected from two farms, Farm A and Farm B. Animals that were diagnosed with congenital tremors were positive for the pestivirus by RT-qPCR while the virus was not detected in the central nervous tissue or serum of unaffected piglets (Table 3). The virus was detected in the serum from a single sow from Farm A.

TABLE 3

Quantitative Real-time PCR Results from Piglet Samples from Farm A and Farm B.

| | | | Sample Type | | | | | | | | | |
|---|---|---|---|---|---|---|---|---|---|---|---|---|
| | Animal | Disease | Cerebrum | | Cerebellum | | Brainstem | | Spinal Cord | | Serum | |
| Farm | ID | Status[a] | Cq[b] | SQ[c] | Cq | SQ | Cq | SQ | Cq | SQ | Cq | SQ |
| A | P1 | − | U[d] | 0 | U | 0 | U | 0 | U | 0 | U | 0 |
| | P2a | + | U | 0 | 34.18 | 3.95E+02 | 35.93 | 1.36E+02 | 33.39 | 6.38E+02 | 30.64 | 1.14E+05 |
| | P2b | + | U | 0 | 35.92 | 1.37E+02 | U | 0 | 35.53 | 1.74E+02 | 30.14 | 1.47E+05 |
| | P4a | + | U | 0 | 32.44 | 1.13E+03 | U | 0 | 36.51 | 9.56E+01 | 36.44 | 6.62E+03 |
| | P4b | + | U | 0 | 29.37 | 2.14E+05 | 35.41 | 1.87E+02 | U | 0 | 30.97 | 9.71E+04 |
| | P5a | − | U | 0 | U | 0 | U | 0 | U | 0 | U | 0 |
| | P6a | + | U | 0 | 33.65 | 4.76E+02 | U | 0 | 33.89 | 4.71E+02 | U | 0 |
| | P6b | + | U | 0 | 28.75 | 2.89E+05 | U | 0 | U | 0 | 31.37 | 8.00E+04 |
| | 1 | + | 32.65 | 1.00E+03 | U | 0 | U | 0 | 35.65 | 1.61E+02 | 30.92 | 1.05E+05 |
| | 2 | + | U | 0 | 32.31 | 1.23E+05 | U | 0 | 35.72 | 1.54E+02 | 30.77 | 1.13E+05 |
| | 3 | − | U | 0 | U | 0 | U | 0 | U | 0 | U | 0 |
| | 4 | − | U | 0 | U | 0 | U | 0 | U | 0 | U | 0 |
| | 5 | + | U | 0 | 30.50 | 3.69E+03 | U | 0 | 35.90 | 1.38E+02 | 33.97 | 2.31E+04 |
| | 6 | + | ND[e] | ND | ND | ND | ND | ND | ND | ND | 29.40 | 2.23E+05 |
| | 7 | + | U | 0 | 32.39 | 0 | U | 0 | U | 0 | 31.29 | 8.74E+04 |
| B | 20 | + | 26.59 | 8.36E+05 | 24.04 | 2.92E+06 | 24.56 | 2.27E+06 | 25.50 | 1.42E+06 | 26.04 | 1.09E+06 |
| | 21 | + | 30.92 | 9.96E+04 | 26.25 | 9.89E+05 | 27.41 | 5.58E+05 | 26.14 | 1.04E+06 | 22.26 | 6.98E+06 |
| | 22 | + | 25.79 | 1.24E+05 | 29.32 | 2.19E+05 | 27.31 | 5.85E+05 | 26.14 | 1.04E+06 | 22.25 | 7.04E+06 |
| | 23 | + | 27.51 | 5.31E+05 | 23.45 | 3.91E+06 | 26.43 | 9.05E+05 | 24.46 | 2.38E+06 | 22.47 | 6.31E+06 |
| | 24 | + | 27.93 | 4.34E+05 | 24.13 | 2.79E+06 | 27.25 | 6.05E+05 | 24.10 | 2.38E+06 | 22.25 | 7.04E+06 |

[a]Presence (+) or absence (−) of congenital tremors.
[b]Cq = quantification cycle value.
[c]SQ = starting quantity.
[d]U = "undetected" following 40 cycles.
[e]ND = Not done.

Sow Inoculation Model

Sow Observations and Samples

One sham-inoculated sow at 45 days gestation developed a moderate fever following surgery and aborted all fetuses on DPI 3 and 4. A sow from the group to be inoculated at 45 days of gestation was found not to be pregnant at time of inoculation; she was removed from the study. Sham-inoculated and pestivirus-inoculated sows did not display clinical signs nor did they develop a detectable viremia or shed the virus at levels detectable by RT-qPCR. All sows farrowed naturally. There was one stillborn piglet (Sow ID 3661) and one macerated fetus (Sow ID 3500).

Piglet Observations and Samples

Sham-inoculated piglets did not have clinical signs consistent with CT on DPF 0, 1, or 2 (S4 MP4). A majority of piglets that were pestivirus-inoculated as fetuses at 45 or 62 days gestation had clinical signs consistent with CT (S4 MP4). The prevalence of congenital tremors (S5 MP4) and splay leg (S6 MP4) in pestivirus-inoculated litters ranged from 57% to 100% and 0% to 40% on DPF 2, respectively (Table 4). Tremor severity varied within litters by piglet but remained relatively constant over the two day observation period in a majority of piglets (Table 5).

TABLE 4

| Prevalence of Congenital Tremors and Splay Leg in Pestivirus-Inoculated Litters on Day 2 Post-farrowing | | | | |
|---|---|---|---|---|
| | Congenital Tremors | | Splay Leg | |
| Sow ID/ Gestation Day[a] | No. Affected[b]/ No. in Litter | Prevalence (%) | No. Affected/ No. in Litter | Prevalence (%) |
| 4036/45 | 5/8 | 62.5 | 1/8 | 12.5 |
| 3992/45 | 7/9 | 77.7 | 2/9 | 22.2 |
| 3661/62 | 4/6 | 66.6 | 0/6 | 0.0 |
| 3500/62 | 10/10 | 100 | 4/10 | 40.0 |
| 4023/62 | 4/7 | 57.1 | 0/7 | 0.0 |

[a]Day of gestation at time of inoculation.

[b]Piglets were considered to be affected by congenital tremors if the tremor severity score was ≥0.75.

TABLE 5

| Congenital Tremor Score by Piglet and Days Post-Farrowing | | | | |
|---|---|---|---|---|
| Sow ID/ Inoculum/ | | Average Tremor Severity Score | | |
| Gestation Day[a] | Animal ID | DPF[b] 0 | DPF 1 | DPF 2 |
| 2427/PBS/62 | 71 | 0 | 0 | 0 |
| | 72 | 0.25 | 0 | NA |
| | 73 | 0 | 0 | 0 |
| | 74 | 0.50 | 0 | 0 |
| | 75 | 0 | 0 | 0 |
| | 124 | 0.25 | 0.5 | 0 |
| | 125 | 0 | 0 | 0 |
| 4036/pestivirus/45 | 31 | 2.00 | 0 | 0.75 |
| | 32 | 0.25 | 0.25 | 0 |
| | 33 | 3.50 | 4.00 | 4.00 |
| | 34 | 0.50 | 0 | 0 |
| | 35 | 3.75 | 4.0 | 4.0 |
| | 36 | 3.75 | 4.0 | 4.0 |
| | 37 | 1.00 | 0 | 0.25 |
| | 38 | 3.50 | 3.5 | 3.5 |
| 3992/pestivirus/45 | 40 | 4.00 | 3.25 | 3.25 |
| | 41 | 0.25 | 0 | 0 |
| | 42 | 3.00 | 1.75 | 1.5 |
| | 43 | 2.00 | 0.25 | 0.25 |
| | 44 | 2.50 | 1.50 | 1.75 |
| | 45 | 3.00 | 3.75 | 4.00 |
| | 46 | 3.25 | 2.50 | 2.75 |
| | 47 | 2.25 | 1.25 | 1.25 |
| | 48 | 3.00 | 2.00 | 2.50 |
| 3661/pestivirus/62 | 94 | 1.00 | 2.5 | 3.0 |
| | 95 | 0 | NA | NA |
| | 96 | 2.00 | 3.00 | 3.25 |
| | 97 | 0.75 | 0 | 0 |
| | 98 | 2.50 | 2.0 | 2.5 |
| | 99 | 2.25 | 2.50 | 2.25 |
| | 100 | 0 | 0 | 0.25 |
| 3500/pestivirus/62 | 89 | 2.75 | 2.75 | 3.25 |
| | 90 | 3.75 | 3.25 | 3.50 |
| | 111 | 3.50 | 3.00 | 2.50 |
| | 112 | 1.75 | NA | NA |
| | 113 | 2.50 | 2.50 | 3.00 |
| | 116 | 3.25 | 3.75 | 4.00 |
| | 117 | 3.50 | 3.25 | 3.25 |
| | 118 | 3.25 | 4.00 | 3.75 |
| | 121 | 2.75 | 1.75 | 3.00 |
| | 122 | 2.00 | 2.75 | 2.75 |
| | 123 | 3.00 | 2.75 | 2.75 |
| 4023/pestivirus/62 | 114 | 0.50 | 0 | 0.50 |
| | 115 | 1.50 | 3.50 | 4.00 |
| | 119 | 1.00 | 1.50 | 2.25 |
| | 120 | 0 | 0 | 0.25 |
| | 130 | 1.00 | 0.50 | 2.25 |
| | 131 | 0 | 1.00 | 0 |
| | 132 | 1.75 | 0.25 | 0.75 |

[a]Day of gestation at time of inoculation.

[b]DPF = Days post-farrowing.

Figure 6:
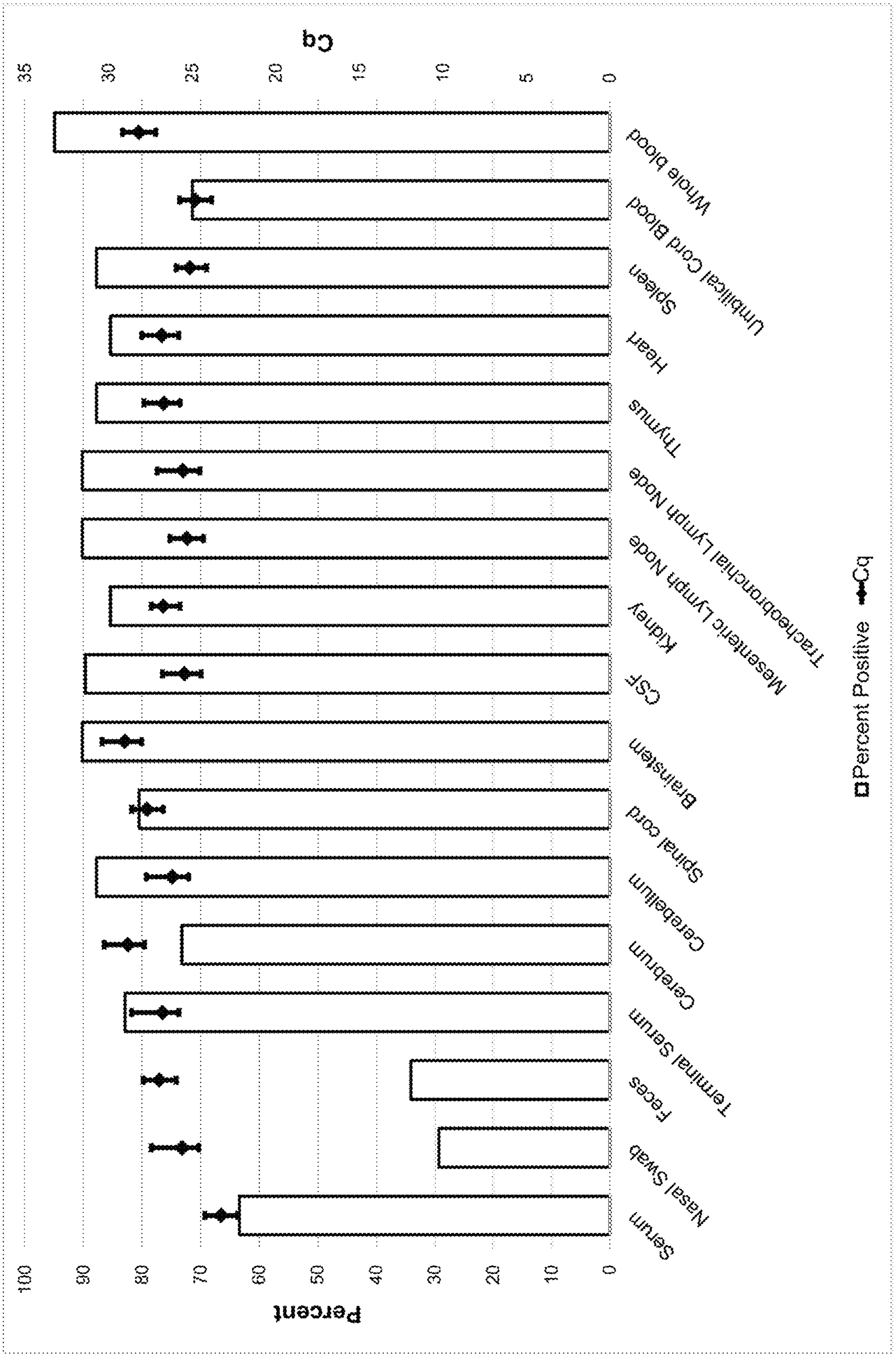
FIG. 6 is a bar graph showing percent positive and average RT-qPCR Cq by sample type. Pestivirus RNA detected by RT-qPCR targeting the NS3 gene. Viral RNA was not detected in PBS-inoculated piglets.

Viral nucleic acids were extracted from tissues, sera, and whole blood collected and analyzed by quantitative-real time PCR. While no pestivirus positives were observed in any tissue within the placebo inoculated litter, nearly all of the animals from the experimentally inoculated group were positive in at least one tissue. Tissue tropism was broad as pestivirus RNA was detected in serum (26 out of 41), nasal swabs (12 out of 41), feces (14 out of 41), terminal serum (34 out of 41), cerebrum (30 out of 41), cerebellum (36 out of 41), brainstem (37 out of 41), spinal cord (33 out of 41), kidney (35 out of 41), mesenteric lymph node (37 out of 41), tracheobronchial lymph node (36 out of 41), thymus (37 out of 41), heart (35 out of 41), and spleen (37 out of 41) by RT-qPCR in live-born pestivirus-inoculated piglets (FIG. 6); viral RNA was not detected in the same samples from PBS-inoculated piglets. In addition, pestivirus RNA was detected in umbilical cord blood (5 out of 7), whole blood (19 out of 20), and CSF (26 out of 29) from a subset of piglets (FIG. 6). The average Cq of serum, nasal swabs, CSF, mesenteric lymph node, tracheobronchial lymph node, spleen and umbilical cord blood was less than 26. The average Cq of feces, terminal serum, cerebellum, spinal cord, kidney, thymus, and heart ranged from 26 to 28. Cerebrum, brainstem, and whole blood had the highest average Cq values (>28). Pestivirus RNA was detected most commonly (>90% of the samples taken) in the brainstem, mesenteric lymph node, tracheobronchial lymph node, and whole blood; less commonly (80 to 90% of the samples taken) in terminal serum, cerebellum, spinal cord, CSF, kidney, thymus, heart, and spleen; and least commonly (29 to 74% of the samples taken) in serum, nasal secretions, feces, cerebrum, and umbilical cord blood. Serum from two animals (35 and 90) were randomly selected to assess genomic stability by complete genome sequencing. Both animals exhibited identical 7 nucleotide fixed changes from the parental strain leading to four conserved amino acid changes. Upon review of the deep sequencing data of the challenge material, evidence of polymorphism was observed at each of these positions.

Discussion

The syndrome of CT was first documented nearly 100 years ago; yet, most contemporary outbreaks have been attributed to an unidentified virus. Using next-generation sequencing, a novel agent originally identified to be closely related to a bat pestivirus was detected in samples of piglets with CT.

A RT-qPCR was designed targeting the N3 S portion of the genome of the divergent lineage pestivirus in order to detect viral RNA in multiple and varied sample types. A retrospective analysis detected pestivirus RNA by RT-qPCR in 6% (21 of 362) of samples from herds experiencing varied clinical signs suggesting that the virus is present in tissues from this sample set at a low prevalence. Samples from the inoculation study were selected based on clinical signs of CT and tissue distribution and replication sites of CSFV. Tissue samples from piglets with CT from two unrelated farms contained viral RNA that was consistently detected in serum and central nervous system tissue suggesting that the virus has a systemic distribution while clinically impacting central nervous system function. This is further supported by the tissue distribution of viral RNA in the pestivirus-inoculated piglets. A specific site of replication was not determined, as all tested tissues had similar levels of detectable pestivirus RNA. This may suggest that viral replication occurs systemically and may include peripheral blood mononuclear cells or endothelial cells similar to CSFV.

The pestivirus used for this inoculation model was viremic serum as attempts at in vitro virus cultivation have not been successful. The immune status of the sows in this study is not known due to the lack of a serologic assay for this newly discovered virus. To avoid possible interference from anti-pestivirus antibodies in the sow, fetal amniotic vesicles were directly inoculated, as the porcine placenta does not allow the transfer of antibodies from the dam to the fetuses.

Although one PBS-inoculated sow aborted as a result of the surgical procedure, no clinical differences were observed between sham- and pestivirus-inoculated sows. Stillbirths, mummified or macerated fetuses have not been previously reported with CT outbreaks. The single stillbirth in one litter and single macerated fetus in another litter from pestivirus-inoculated sows were considered incidental and likely not a result of fetal infection. Despite IN and IV inoculation, sows did not develop a detectable viremia or shed the virus at levels detectable by RT-qPCR. Therefore, either the sows were not infected following challenge or the available diagnostic tests were insufficient to detect infection.

For CT to be manifested, it is likely that fetal infection must occur prior to development of fetal immunocompetence which occurs around 70-80 days of gestation in piglets. In this study, fetuses at both 45 and 62 days of gestation were susceptible to infection with the divergent lineage pestivirus which resulted in CT in a majority of infected piglets. The selection of these two gestation time points was based on an approximate viremia of this pestivirus based on CSFV occurring prior to the development of fetal immunity (day 45 of gestation) and the development of the fetal central nervous system (day 62 of gestation). In utero pestivirus infections in other species at different gestational time points have differing clinical outcomes including reproductive failure, congenital malformations or immunotolerance whereby a persistently infected animal may shed virus throughout their lifetime. In this study a number of pestivirus-inoculated piglets were born with splay leg. This condition is commonly observed in pigs; however, the pathogenesis and etiologies are currently speculative. The role, if any, of this pestivirus in splay leg, reproductive failure in sows or ability for in utero infection to result in persistently infected animals requires additional investigation.

Overall, the clinical disease reproduced herein mimics naturally occurring outbreaks with variation in the prevalence of CT between litters and severity of clinical signs within litters. Viral RNA was detected in all piglets with CT. Moreover, viral RNA was detected in 41 out of 42 live-born pestivirus-inoculated piglets. Of the live-born pestivirus-inoculated piglets, eleven did not have CT on DPF 2 or DPF 0 (95), and viral RNA was detected in all pestivirus-inoculated unaffected piglets but one (95). Yet, the mechanism of central nervous systemic dysfunction in a majority of piglets but not all infected piglets is currently unknown. The ecology and pathogenesis of the host-virus interaction is undefined at this point but intriguing. Investigation of the role of persistent infection or dysfunctional immune response in clinical expression of CT and mechanism of central nervous system dysfunction is warranted. Literature concerning the mechanisms of tremor disorders in humans and animals is limited despite the high prevalence and importance of such symptomatology in human and veterinary medicine.

This study identified a recently described divergent porcine pestivirus in piglets with CT and not in unaffected cohorts and used this virus to reproduce CT through the development of an innovative inoculation technique. The successful development of virus isolation techniques, specific antibody assays, in situ detection techniques and refined molecular tools will undoubtedly lead to better understanding of pathogenesis and epidemiology of this virus.

Example 3

The objective of this study is to evaluate the efficacy of a pestivirus vaccine when administered pestivirus naive or seronegative dams.

Study Design

A total of 10 dams were used for this experiment. Dams were randomized into three groups. Group 1 animals (n=4) were vaccinated at D0 and D14 with a prototype pestivirus vaccine just prior or shortly after breeding. Group 2 animals (n=4) vaccinated with a placebo prototype vaccine preparation. Group 3 animals (n=2) remained unvaccinated (strict controls). The animals in each group were maintained in separate rooms. At approximately 42 days of gestation, dams in Group 1 and 2 were challenged with pestivirus by a route such as intravenous, intramuscular, intranasal, intravaginal or intrauterine inoculation. Following challenge, dams will be monitored daily for clinical signs throughout the study. Serum, fecal and nasal samples and rectal temperatures were collected twice weekly throughout gestation. At approximately 80 days of gestation, an ultrasound evaluation was performed on all sows. At the time of farrowing, piglets were visually assessed for the presence of clinical signs. Serum, cord blood and placenta were collected for detection of pestivirus. Piglets were processed and video recordings were taken. Piglets were maintained on the sow. When piglets are 24 hours old, piglets were visually assessed for the presence of clinical signs and video recordings were captured. Piglets were euthanized at 48 hours of age. Prior to euthanasia, piglets were visually assessed for the presence of clinical signs and video recordings will be captured. Selected tissues and blood were collected at the time of necropsy. Samples were screened for pestivirus RNA and anti-pestivirus antibodies.

TABLE 6

Experimental design

| Group | n | Vaccination (D 0, D 14) | Challenge (~42 days of gestation) |
|---|---|---|---|
| 1 | 4 | Pestivirus prototype vaccine | Yes |
| 2 | 4 | None | Yes |
| 3 | 2 | Strict | No |

TABLE 7

Schedule of key events where DPC refers to day post challenge

| Study Day | Study Event |
|---|---|
| TBD | Dams arrive at ISU |
| | Evaluation of dams |
| D 0-D 14 | Feed Matrix to all dams |
| | Daily clinical observations |
| D 18-D 24 | Check for estrus with hog mate & breed all dams |
| D 0, D 14 | Vaccination of dams |
| | Collection of serum, nasal and fecal samples prior to vaccination |
| D 54 | Pregnancy check on all dams |
| D 66 | Dams challenged |

TABLE 7-continued

Schedule of key events where DPC refers to day post challenge

| Study Day | Study Event |
|---|---|
| (~day 42 of gestation) | Collection of serum, nasal and fecal samples prior to challenge |
| ~D 137 (day of farrowing) | Expected farrowing date<br>Processing of piglets<br>Video of all piglets at the time of farrowing<br>Collection of cord blood and placenta<br>Collection of blood, nasal and fecal samples from piglets |
| ~D 138 (24 hr post farrowing) | Video of all piglets at the time of farrowing<br>Collection of blood, nasal and fecal samples from piglets |
| ~D 139 (48 hr post farrowing) | Video of all piglets at the time of farrowing<br>Collection of blood, nasal and fecal samples from piglets<br>Necropsy all piglets and sows (collection of tissues) |

To ensure blinding, the person (Administrator) administering the vaccine of the present invention and the control were not the same person responsible for the clinical observation and sampling of the study animals. The laboratory tests were the same as described in Example 2.

Example 4

The primary objective of this study was to determine feasibility of inducing a pestivirus-specific serological response following inactivated whole virus vaccine administration. Specifically, naïve animals were exposed to an intramuscular injection of concentrated, inactivated virus and evaluated by serological ELISA pre- and post-vaccination.

A novel virus most closely related to a Chinese bat pestivirus was discovered using deep sequencing technology from multiple outbreak investigation cases. Clinical histories of these cases included congenital tremors (2 cases), anemic piglets (1 case), or fallback piglets thought to be associated with PCVAD (1 case). Based on the findings, a qPCR was designed and the prevalence of the identified virus was determined in two sample sets collected from the Iowa State University Veterinary Diagnostic Laboratory (ISU VDL). The apparent prevalence was found to be 7.3% (8/110) in a set of lung homogenates and 5.2% (13/252) in a set of clinical samples from cases with a history of polyserositis. Additional samples from two farms with a clinical history of congenital tremors were collected through collaboration with an ISU VDL faculty member (Dr. Paulo Arruda). These samples were used for inoculation of pigs and serum containing high levels of virus was generated (Example 1). In a follow-up study, it was demonstrated that intrauterine inoculation of the serum into pregnant dams resulted in high percentages of pigs born with congenital tremors (Example 2). Due to the ability of pestivirus to cause clinical disease, it is of interest to develop a vaccine. A conventional, inactivated vaccine was included in this study.

A conventional, inactivated vaccine will be included in the study. In addition, a viral vector will be included in the study. As the use of live viral vectors for expression of relevant antigens is a key component of the Lead2Grow strategy, this study will provide an evaluation of the vector in pigs. This study will utilize the canine adenovirus vector (CAV-2; licensed for use in the Solo-Jec CAV-2) expressing the E2 protein of pestivirus. The vector is replication competent and hypothesized to induce a broad immune response of long duration. An additional CAV construct expressing an Influenza A HA gene will be included as a construct control.

Animal Inclusion Criteria

As the study was done in animals that were born under BSL2 conditions and serological assays are not currently available for pestivirus, no pre-screening of serum samples was done. Only pigs that are healthy at the time of vaccination were included in the trial. If at the time of vaccination, the investigator noted animals that were unhealthy, those animals were not vaccinated and were humanely euthanized.

Animal Care

All animals were housed at the animal facilities at Sioux Center, Iowa for the duration of the study. Animals were fed a commercial ration that is appropriate for their size, age, and condition according to acceptable animal husbandry practices for the region (antibiotics may be included). Water was available ad libitum. Floor and feeder space met or exceeded requirements set forth in the Consortium "Guide for the Care and Use of Agricultural Animals in Agricultural Research and Teaching", third edition, January 2010.

No other biological or pharmaceutical products were administered to the test animals without prior approval by the study monitor.

Post-Inclusion Removal Criteria

Any moribund animal was euthanized at the discretion of the Attending Veterinarian/Investigator. A moribund animal was defined as an animal that is unwilling to eat or drink or is severely dehydrated due to severe clinical signs. Any animal that died or was euthanized throughout the study period was necropsied by a veterinarian. The necropsy was done as described below. The monitor and investigator consulted to determine if the data from the removed test animals were included in the data analysis and final report.

Study Animal Disposal

All animals were humanely euthanized, accounted for, and disposed of by rendering at the termination of the study. All procedures were done as described in facility SOPs.

Experimental Design

General Description

This experiment was designed to evaluate the serological response of prototype pestivirus vaccines in conventional animals. See Table 8 below for an explanation of the experimental groups.

At the time of weaning, a total of six animals, approximately six weeks of age, were randomized into Group 1 and 2 and administered a 2 mL dose of either vaccine or placebo according to Table 8. Animals were randomized and co-mingled in separate crates within the same room. Animals in Group 3 were comingled in a separate room. General health observations were recorded throughout the study, and no adverse reactions were observed. At approximately 14-days post vaccination, serum was collected and held at 4° C. until processing completed for serological evaluation. A booster vaccination of identical materials was administered 21 days after the primary vaccination. Serum from animals was collected 13 days following boost (day 34).

Serum samples were assayed for evidence of seroconversion as assays became available. Oral, nasal and fecal swabs were collected from pigs daily in Group 3 from D0-D7. Samples were assessed for the presence of live CAV. Injection sites were observed for reactions for a minimum of three days following administration of the vaccine. Animals were humanely euthanized at the end of the trial. See Table 9 below for an overview of study action items and specific procedure details.

TABLE 8

| Experimental design | | | | |
|---|---|---|---|---|
| Group | Room | N (piglets) | Vaccine treatment (6 and 9 weeks post-farrow) | Dose/ Route |
| 1 | 1 | 4 | Pestivirus inactivated prototype vaccine | 2 mL/IM |
| 2 | 1 | 8 | Placebo (phosphate buffered saline + 12.5% emulsigen D) | 2 mL/IM |
| 3 | 2 | ~7 | Pesti-CAV-2 prototype vaccine | 2 mL/IM |

TABLE 9

| Schedule of key events by room | | |
|---|---|---|
| Study Day | Study Event | Testing |
| TBD | Perform GHO daily until D 0 | None |
| D 0 | Vaccination #1<br>Injection site observations for three days following vaccination<br>Collection of serum from all animals | Serum sample: serological assay |
| D 0, 1, 2, 3, 4, 5, 6, 7 | Collection of oral, nasal & fecal swabs from animals in Group 3 | Swab samples: Samples saved back for future testing/evaluation of shedding |
| D 21 | Vaccination #2<br>Collection of serum from animals<br>Injection site observations for three days following vaccination | Serum sample: serological assay |
| D 0-D 35 | General health observations (1 x daily) | None |
| D 35 | Necropsy<br>Collection of terminal serum (1 x 250 mL bottle) from all animals | Serum samples: serological assay |

Vaccine Material

Supernatant from infected SK6 cells was concentrated 10-fold by ultracentrifugation and inactivated with 5 mM BEI solution for 6 hours at 37° C. Vaccine was formulated with 12.5% emulsigen D stored at 4° C. until time of administration. Pigs in Group 2 received placebo material (phosphate buffered saline+12.5% emulsigen D). A 2 mL dose of the appropriate vaccine was administered into the musculature of the neck using appropriately-sized, sterile needle and syringe.

Vaccination

Prior to administration of any vaccine material, the Investigator or designee examined all animals for overall health and inclusion in the study. At D0 and D21, a 2 mL dose of the appropriate vaccine was administered either into the musculature of the neck using appropriately-sized, sterile needle and syringe or administered into the nose (1 mL per nare) using a sterile syringe and cannula. For IM injections, the musculature of the right neck was used for injection on D0, and the musculature of the left neck was used for injection on D21. The lot number, dosage amount, animal identification numbers and timing of administration of vaccine material was recorded on the vaccine confirmation record.

Clinical Observations

During the vaccination period, animals were evaluated daily using a general health observation form. Injection site areas were monitored for a minimum of three days following vaccination. If lesions were present in injection site areas, the areas were monitored until the lesion resolves or until the termination of the study.

Blood Collection

On blood collection dates, three to nine mL of venous whole blood was collected by the Investigator or designee via the anterior vena cava. A sterile 18-20 g×1 inch (2.54 cm) to 1.5 inch (3.81 cm) VACCUTAINER® needle, a VACCUTAINER® needle holder and appropriately sized serum separator tubes (SST) was used. The blood was shipped overnight to BIVI Biological R&D in Ames, Iowa on ice on the day of collection, if collected Monday through Thursday. If serum was collected on Friday or Saturday, the serum was separated from the clot by centrifugation and decanted into a screw-cap cryogenic vial labeled with at least study number, day of study, and animal ID. Processed serum samples were stored at −70° C. and shipped on dry ice to Ames on the next shipment day. At BIVI-Ames, serum samples were tracked via FreezerWorks electronic management system. Serum samples at BIVI-Ames were held at 2-8° C. if tested <48 hours after delivery or held at −70° C. if tested at a later date. The samples were stored for a minimum of six months after the completion of this study.

Swab Samples

The materials were shipped overnight to BIVI Biological R&D in Ames, Iowa on ice. If collection occurred on a weekend, samples were frozen at −70° C. and shipped on dry ice on the next sampling day. Samples at BIVI-Ames were held at 2-8° C. if tested <24 hours after delivery or held at −70° C. if tested at a later date. Samples were tracked via FreezerWorks electronic management system. The samples were stored for a minimum of six months after the completion of this study.

Necropsy

If, during the study, there was a moribund animal, the animal was euthanized and necropsied at the discretion of the attending veterinarian. Appropriate samples were collected to determine the cause of death. Samples may be submitted to a diagnostic laboratory for confirmatory testing.

At the time of off-test, animals were deeply anesthetized per facility SOP's and 1×250 mL centrifuge bottle of blood (free catch) was collected from each animal. The animal was euthanized following facility SOPs and the injection site were palpated. If injection site reactions are grossly palpated at the time of necropsy, a sample (fresh and fixed) was collected. If clinical signs were present in the animal during the study or there is evidence of clinical disease, the animal was necropsied. Appropriate samples were collected to determine the cause of disease. Samples may be submitted to a diagnostic laboratory for confirmatory testing.

Room Disinfection, Entry and Chore Procedures

Prototype vaccines are not considered infectious to humans. Gloves, masks and disposable TYVEK® were worn when working with animals. Boots and personal protective equipment (PPE) were room specific. A shower was required between work done in Group 3 animals and the animals in Groups 1 and 2. No transfer of supplies or PPE between rooms was allowed. Facility and equipment disinfection were detailed and placed into the investigator's report.

Serological Response

Figure 7:
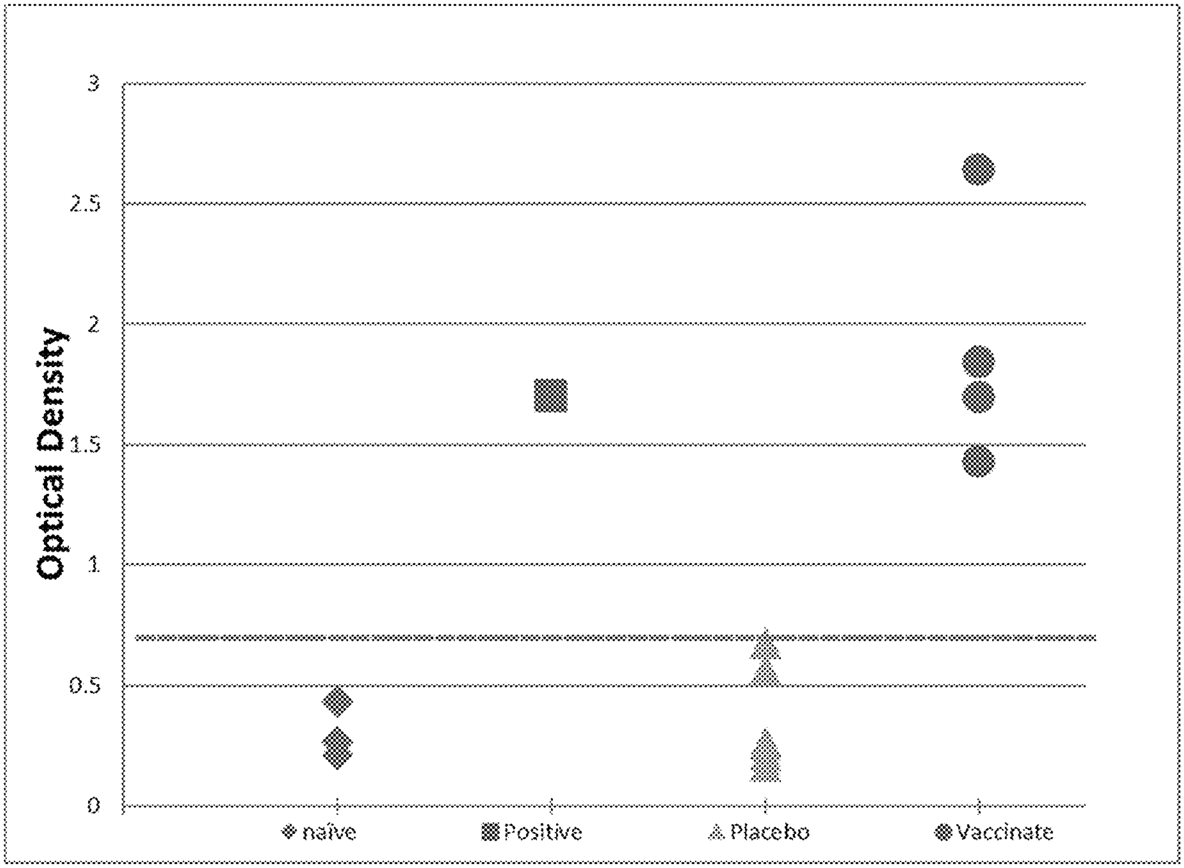
FIG. 7 is a graph that shows inactivated pestivirus induced a pestivirus specific serological response in vaccinated piglets.

Spun serum was absorbed against porcine primary lung cells to reduce enzyme linked absorbance assay (ELISA) background. ELISA plates were coated with 300 ng of concentrated inactivated pestivirus. Absorbed test serum from vaccinated animals, placebo animals, convalescent positive control sera, and sera from naïve animals were evaluated in duplicate with data summarized in FIG. 7. All sera collected from all groups were negative by ELISA at day 0 (OD<0.15). By 13 days post-boost inoculation of inactivated pestivirus, all four animals exhibited a strong serological response while none of the matched placebo controls exceeded the 0.7 OD threshold for the assay. Using an Exact Wilcoxon rank-sum test, there is a statistically significant increase in OD within the vaccinated group compared to the placebo (p-value=0.004), indicative of a specific serological response to the pestivirus.

Example 5

The primary objective of this study was to isolate and productively replicate the novel pestivirus ex vivo. Specifically, viral propagation was achieved in cells derived from the natural host species (porcine) and were monitored through molecular biological techniques.

Inoculum Preparation

Tissues of infected piglets from Example 2 were collected and weighed individually, and SAFC modified minimum essential medium (MEM) was added to each for a final weight:volume of 10%. Tissues were dispersed by high-speed shaking with metal beads, clarified by microcentrifugation, and filtered through a 0.2 μm filter. Additionally, terminal blood from pestivirus infected piglets of Example 2 were individually collected. Each of the tissue homogenates and serum samples were assayed for the presence and relative concentration of pestivirus using qPCR. Samples with the highest titers were pooled based on sample type from terminal serum, spleen and kidney homogenates. These pools were subsequently used as inoculum.

Inoculation of Porcine Primary Tissues

Viral growth attempts were performed using inoculum described above on both primary embryonic porcine lung and primary porcine embryonic kidney cell cultures. Primary cell cultures were prepared from tissues collected from caesarean derived colostrum deprived (CDCD) pigs.

Inoculum was diluted with an equal volume of MEM and sterilized by passing through 0.8 μm/0.2 μm filters. Samples were further diluted either 1:2 or 1:10 prior to inoculation in an attempt to remove any serum or host cell associated toxicity.

Culture was performed in growth media (MEM with 10% irradiated fetal bovine serum and 2.5% 1M HEPES). After seven days on culture, materials were subjected to 3-cycles of freezing/thawing and then inoculated onto fresh cells by allowing viral infection for 1 hour at 37° C., 5% $CO_2$ while rocking. After 1 hour, inoculum was removed and replaced with growth media. Passage continued for 11 rounds in primary lung cells and 4 rounds in primary kidney cells. The cycle threshold values for primary kidney cells ranged between 21.3-22.5, indicative of productive replication. The cycle thresholds for primary lung also are indicative of productive viral replication and are summarized in Table 8.

TABLE 8

Experimental design

| Cell type for virus passage | Virus passage | Pestivirus qPCR Ct value |
|---|---|---|
| Primary Lung | P1 | 28.6 |
| Primary Lung | P4 | 21.6 |
| Primary Lung | P7 | 20.9 |
| Primary Lung | P11 | 21.8 |
| SK6 | X + 1 | 22.6 |
| SK6 | X + 4 | 22.0 |
| SK6 | X + 10 | 17.2 |
| SK6 | X + 14 | 16.45 |

Inoculation of Immortalized Porcine Cells

Similar to the original inoculation conditions of primary cells, immortalized swine kidney cells (SK6) were inoculated by adding supernatant from the pass 11 primary lung culture (frozen/thawed for three cycles) and incubated for 1 hour at 37° C., 5% $CO_2$ while rocking. After 6 days of incubation at 37° C., 5% $CO_2$ material was passaged to fresh SK6 cells in same manner. Nucleic acids from each pass were extracted after 14 passes and monitored by qPCR. Upon serial passage, the cycle thresholds decreased (see Table 8) to ~17, indicative of an approximate 10-fold increase in viral titer.

Inactivation of Viral Harvest

Supernatants from passage 11 SK6 cells were pooled and concentrated ~10-fold through high speed centrifugation to pellet virus. Viral pellets were re-suspended in ~1⁄10th the original volume of inert buffer (1× phosphate buffered saline). Concentrated virus was inactivated using cyclized binary ethyleneimine (BEI) at a final concentration of 5 mM for 6 hours and constant agitation at 37° C. Upon completion of inactivation, the BEI was inactivated with sodium thiosulfate solution (17% by volume) with incubation at 37° C. for 15 minutes. Inactivated pestivirus was formulated with 12.5% final concentration of emulsigen D and used as putative vaccine candidate in Example 4.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

What is claimed is:

1. A method of inducing an immune response in a pig, wherein the method comprises administering to a pig, a composition comprising an inactivated pestivirus comprising a nucleic acid sequence that has at least 95% sequence identity to SEQ ID NO: 1 in an amount sufficient to induce an immune response in the pig.

2. The method of claim 1, wherein the inactivated pestivirus is a chemically inactivated pestivirus inactivated by treatment with binary ethyleneimine, ethyleneimine, acetylethyleneimine, beta-ethyleneimine, beta-propiolactone, glutaraldehyde, ozone, or formaldehyde, or any combination thereof.

3. The method of claim 1, wherein the inactivated pestivirus is a physically inactivated pestivirus inactivated by treatment with UV radiation, X-ray radiation, gamma-radiation, freeze-thawing, or heating, or any combination thereof.

4. The method of claim 1, wherein the composition further comprises a pharmaceutically acceptable carrier and/or excipient.

5. The method of claim 4, wherein the pharmaceutically acceptable carrier and/or excipient is an adjuvant.

6. The method of claim 5, wherein the adjuvant is an oil-in-water emulsion-based adjuvant.

7. The method of claim 5, wherein the adjuvant is selected from the group consisting of: aluminum hydroxide, aluminum phosphate, saponin, GPI-0100, water-in-oil emulsion and oil-in-water emulsion.

8. The method of claim 1, wherein the composition further comprises at least one component selected from the group consisting of: a dispersion media, a coating, a stabilizing agent, a preservative, an antibacterial agent, an antifungal agent, an isotonic agent, and an adsorption delaying agent.

9. The method of claim 1, wherein the pig is a piglet, a sow, a pregnant sow or gilt, or a sow or gilt prior to breeding.

10. The method of claim 1, wherein the administering is a first administration, and wherein the method further comprises a second administration one to three weeks after the first administration.

11. A method of reducing the incidence of or severity of one or more clinical signs associated with or caused by a pestivirus infection in a pig, wherein the method comprises administering to a pig a composition comprising an inactivated pestivirus comprising a nucleic acid sequence that has at least 95% sequence identity to SEQ ID NO: 1 in an amount sufficient to reduce the incidence of or severity of the one or more clinical signs associated with or caused by the pestivirus infection in the pig.

12. The method of claim 11, wherein the pig is a piglet, a sow, a pregnant sow or gilt, or a sow or gilt prior to breeding.

13. A method for protecting a piglet against congenital tremors, wherein the method comprises administering to a piglet a composition comprising an inactivated pestivirus comprising a nucleic acid sequence that has at least 95% sequence identity to SEQ ID NO: 1 in an amount sufficient to protect the piglet.

14. A method of inducing an immune response in a pig, wherein the method comprises administering to a pig, a composition comprising an attenuated pestivirus comprising a nucleic acid sequence that has at least 95% sequence identity to SEQ ID NO:1 in an amount sufficient to induce an immune response in the pig.

15. The method of claim 14, wherein the composition further comprises a pharmaceutically acceptable carrier and/or excipient.

16. The method of claim 15, wherein the pharmaceutically acceptable carrier and/or excipient is an adjuvant.

17. The method of claim 16, wherein the adjuvant is an oil-in-water emulsion-based adjuvant.

18. The method of claim 16, wherein the adjuvant is selected from the group consisting of: aluminum hydroxide, aluminum phosphate, saponin, GPI-0100, water-in-oil emulsion and oil-in-water emulsion.

19. The method of claim 14, wherein the pestivirus is in freeze-dried form.

20. The method of claim 14, wherein the composition comprises at least about $10^4$ virus particles.

21. The method of claim 14, wherein the composition further comprises at least one component selected from the group consisting of: a dispersion media, a coating, a stabilizing agent, a preservative, an antibacterial agent, an antifungal agent, an isotonic agent, and an adsorption delaying agent.

22. The method of claim 14, wherein the pig is a piglet, a sow, a pregnant sow or gilt, or a sow or gilt prior to breeding.

23. The method of claim 14, wherein the administering is a first administration, and wherein the method further comprises a second administration one to three weeks after the first administration.

24. A method for protecting a piglet against congenital tremors, wherein the method comprises administering to a piglet a composition comprising an attenuated pestivirus comprising a nucleic acid sequence that has at least 95% sequence identity to SEQ ID NO: 1 in an amount sufficient to protect the piglet.

25. A method of reducing the incidence of or severity of one or more clinical signs associated with or caused by a pestivirus infection in a pig, wherein the method comprises administering to a pig a composition comprising an attenuated pestivirus comprising a nucleic acid sequence that has at least 95% sequence identity to SEQ ID NO: 1 in an amount sufficient to reduce the incidence of or severity of the one or more clinical signs associated with or caused by the pestivirus infection in the pig.

26. The method of claim 25, wherein the pig is a piglet, a sow, a pregnant sow or gilt, or a sow or gilt prior to breeding.

27. A method of inducing an immune response in a pig, wherein the method comprises administering to a pig, a composition comprising a baculovirus expression vector or a canine adenovirus expression vector comprising a nucleic acid sequence that has at least 95% sequence identity to SEQ ID NO:3, 5, 7, 9, 11, 13, 15, 17, 19, or 21 in an amount sufficient to induce an immune response in the pig.

28. The method of claim 27, wherein the pig is a piglet, a sow, a pregnant sow or gilt, or a sow or gilt prior to breeding.

29. The method of claim 27, wherein the administering is a first administration, and wherein the method further comprises a second administration one to three weeks after the first administration.

30. A method for protecting a piglet against congenital tremors, wherein the method comprises administering to a piglet a composition comprising a baculovirus expression vector or a canine adenovirus expression vector comprising a nucleic acid sequence that has at least 95% sequence identity to SEQ ID NO: 3, 5, 7, 9, 11, 13, 15, 17, 19, or 21 in an amount sufficient to protect the piglet.

31. A method of reducing the incidence of or severity of one or more clinical signs associated with or caused by a pestivirus infection in a pig, wherein the method comprises administering to a pig a composition comprising a baculovirus expression vector or a canine adenovirus expression vector comprising a nucleic acid sequence that has at least 95% sequence identity to SEQ ID NO: 3, 5, 7, 9, 11, 13, 15, 17, 19, or 21 in an amount sufficient to reduce the incidence of or severity of the one or more clinical signs associated with or caused by the pestivirus infection in the pig.

32. The method of claim 31, wherein the pig is a piglet, a sow, a pregnant sow or gilt, or a sow or gilt prior to breeding.

* * * * *

SEQUENCE LISTING

```
<160> NUMBER OF SEQ ID NOS: 26

<210> SEQ ID NO 1
<211> LENGTH: 11550
<212> TYPE: DNA
<213> ORGANISM: pestivirus type 2

<400> SEQUENCE: 1

cataatgctt taattggccg cattatgtgt gggacatcct aaatatttat gagccctgcg      60
```

-continued

```
gtgagtgggg gaaagaggtt aaccaggcct ctagtaccac aggcaccaat ggacagggca    120
actcaaacct gagagagagg taccgaactc ttaagccccg agtacggggc agacgtcacc    180
gagtagtaca cccaaagacc accacttcta ggtgtagggt ctactgaggc tcgggtggac    240
gtgggcgcgc ccaaagagaa atcggtggtg gacctggggg tcggggccac catgcccctt    300
tacggggtag accttactgc ttgatagagt gccggcggat gcctcaggta agagtataaa    360
atccgttgtt cattaacatg gaaaaacaga ttgcatatta cttaaaaaaa gaaaaacaaa    420
gaaatgggtg gacggaactg gtggtaggag aaagtcatac aaaaataacc acgctttctg    480
gaaagaccta tcgaggcacc tgggaaatgg agaaacggcc aaatccttat ggaacctatc    540
tccccagacc tagtccccaa cagcttacag ccctacaccc ccacccagtg gtgaattgta    600
aggtggttga gtacaaggag atggacccta attatggtga ttgcccaaat acgaacgggg    660
tgtttgttga cgaaaagggt agaaggctga gcagccctcc attaggcatt tggaagataa    720
gattggacta tagtgacttg gtaaacataa gcagaccaac cccgctagt gggaaaaact    780
cttaccaagt tgagacctgc agtggggagc tggctacagt gacactggta cacaataggg    840
tgctcgtgga agattgcagg gggctatacc aatggaaacc caactgtgaa ggaattgtgc    900
tctatgtgaa aacttgttct gactgggcag atcaggtaga aaaacaggag aaagaaagcc    960
ccccaaaacc acagcggcca ccaaggcgag acccacgaaa agggttacaa ccacaagtcc   1020
ccaaagagac tgaggtcaca gaaaagaaga gacaacctag tgtcacctta gtatcggggg   1080
ggcagaaggc ccaagtcatc tacaaaggca ggaccaaaaa caaaaagacc ccggatggag   1140
tctatagata cccaggagct aaagaagggg acgtagtaaa ggtcaggaag atgctgaaga   1200
attggcatat agccttagtg atgtacctga tacatatcat aactccaggc cttgccaagg   1260
tccagtggtt cttaaaagat gaaaactcga cggggatcaa ccagatactg tggcaaagac   1320
agatcaacag atccttacat ggagaatggc ctaaccagat ctgccacggt atgcccaatg   1380
aaactatcac ggatgaggaa ttacgcagtc tgggaatggt agatacaagc cctagaacaa   1440
actacacctg ttgccagttg caatatcatg agtggaagaa acatggttgg tgcaactatc   1500
cacaaaaaca ggcgtggatc acgaggataa cggccctaca agctaacctt accgggcctt   1560
atgagggacc tgagtgcgcc gtcatctgcc gatttaacgg cagctacaac atcgtaaaac   1620
aggccagaga tgaggtgagt ccactgacag ggtgcaagga agggcatcct tttctattct   1680
ctggtgaaag atccgacacc tcatgcctaa ggccccccttc cactagttgg gtaagaccag   1740
tgaaaatgga cgaggcatca atggccgatg gctttgccca tggggttgat aaggcgataa   1800
tactaatcag gaagggggca tcaggaataa tcaatttcct agacactatt gggaggtggc   1860
taccggtagc tgaagcaact atagtaccat attgtgatac ttacactgtg acagggatgt   1920
atgtccatgt aaagaattgc ctccctagag ggttacctaa gcattcaaaa ataatctccc   1980
cgacaatgat atatctggga gaaggagacc cggcccataa tatccagcac ttatttggct   2040
caggtatagc aaagtgggtc ctagttctac tcgggattct gggtgagtgg tatggagaat   2100
tggcttccac aatatactta ctactagaat acgggtctga gtggttggaa catgaaagcc   2160
tggtcacgga agggttgatt cctggcatta atattacaat agaactccca gctagtcata   2220
cagtgcctgg ttgggtgtgg gtcgcaggcc agtgggtatg cgtgaagcca gactggtggc   2280
ctacacagat ttggattgaa accgtggtgg cagagacctg gcatatacta aaaatattgg   2340
cgtcagccct ggtgaacata gttgcagcgt tcgtaaacct ggaattggtt tatctggtca   2400
```

-continued

```
taatactagt caaaatatca aaagggaacc tgataggtgc catattatgg tgcttgttac   2460
tgtcaggcgc tgaaggctcg tgctacaaaa gacaagacta ttacaacacc caactagtcg   2520
tcgaagaaaa aacaggcgta gaaaaacgat ctataatggg caagtggacc gtgataacca   2580
gggaaggtcg ggagccaaga ttaatggagc aaataaatat ggtattgaat gatagcctgt   2640
cagaaaccta ctgctataat aggctaaaca ccagcacttg gggcggcaa ccggcaagac   2700
aaagagggtg tggtcaaacc gtgccctatt ggcctggtga caatgttcta gaagaacaat   2760
actacagcac aggttactgg gtgaatgtaa caggcggttg ccagctgaga gaaggcgtat   2820
ggctatcaag aaagggtaac gtacagtgtc agcgtaacgg ctcatccttg atgctgcaat   2880
tggcgataaa agaagagaat gacactatgg aaataccatg tgacccagtg gaaactgaaa   2940
gtatgggtcc agttgcacag ggcacttgtg tgtacagctg ggcattcgcc ccaagagggt   3000
ggtactataa caggaaggat ggttattggc tccagtacat aaagaaaaac gactaccagt   3060
attggacaaa aatgcctact gcctcgtccg ccgcaaccat gtaccgccac ttgctcccct   3120
tactggtggc ctgcctcatg ggcggtagga tatcggtgtg gtttgtggca atgctcctgt   3180
ctctacaggt ggaagctagt gaagtaggca ctaaacaact ggctgtcacg ctaaccctgt   3240
ggaaaatgga ctggacagaa ctacttttct atattgtctt gatgctagcc gttaaggaag   3300
aacttataaa aaaaattgtg accgctagcc ttgtggcctt aaaaaatagt ccagtagcct   3360
tgagttttct tattgtactc agacttgtgg ggggcagtga agcactccca gtaggtttat   3420
tattagaaaa aatgtgcata gaccaaccgg agtttggaac tcctttcctg atctacctat   3480
gggacaactg gaagtggact gtgttagtca gcttctccgc actgaaccat gaaaaaacta   3540
taaaactggc aagaaaactg ttgttggcaa cacatataac agcgctcaca ttgactggct   3600
tgagtgattc aatcttctat atgatgctta taacaacaaa tttgttaata aagacattca   3660
tatacttgct gggggctagt atgaattggg tcgagagaga aaaaaagaaa ttgctagtga   3720
agaggagact aatatacaag aaagccgtta cttgcagtca ggatgagaat gtattggaga   3780
ataaattcaa caagataact gtaaacgcgg atttcacccc atgcaagctt gaacttctac   3840
aattacttag ggcttttta gtctctttgt gtttttccta ctacaaacct ctcctgtatg   3900
cagagactac cttaactgta atagtaattg gcgtacaaga gtacaacgta gccatggccc   3960
gcgggcgaag tgtggtccac aggctactag ccatggccta ttacatatac ggccgcatac   4020
agggtgacat gttccagctc gccactatcc agtgcctgct gtcgagtccg aggaaaatta   4080
tgaaacacat ggtagagaat ccaactctca agaagctctg gcaaggcgaa acagaactct   4140
tcaaccaggg tgttagtcaa tccaagatag tgaatccaaa gaaaattggg ctggaagaat   4200
tacacaaggg catgtgtggc ctcccaacag tagtgcaaaa tttggtcata tatgcaaaga   4260
agaatgactc tcttatttta ggagagctgg gttacccccc tggggatctc accagtgatg   4320
ggtgggaaat tttaggtcct ggcagaatcc caaagatcac taacgtcgag tctgctaaga   4380
tggacttact ctccaaactt atgacctttc tggggattga aagctcgagg gtccccagga   4440
ccccagtcca ctcaacaagg aaattattga agatagtaag gggcttggaa acaggatggg   4500
ggtacactca cgcagggggg ataagtagcg caaaacacgt tacaggtgaa aagaacttaa   4560
tgacccacat ggagggtagg aagggaaaat atatcctaca atctcaagaa catggtgctg   4620
acgaggtaga gtacggagta aaaactgatc aaaaagctcc cgacaatgcc ttatgctact   4680
gttttaaccc tgaagctaca aacataaaag gagagacggg agccatggtg ttcatgaaga   4740
agataggaaa aaagtggact ctcgtaacat cagacggcaa taaagcctat tataatgtaa   4800
```

-continued

```
acaatttgaa agggtggtct ggactaccaa taatgctgca ctccaccggg gccatagtgg   4860
ggaggattaa atcagcgtat tcagatgaaa acgacctggt ggaggaactt attgactcta   4920
gaactattag taagagcaat gagacaaacc tggaccacct tatcaaggaa ttggcagaca   4980
tgcggagggg ggagttccgc tcaattaccc ttggaacggg agccgggaaa accacagaac   5040
tgcctaggca atacctcaca acagtaggtg cccataaatc cgtgctggtc ttagtcccct   5100
taaaagcacc tgctgaaagt gtttgccgct ttatgaggtc taaataccct accatcaact   5160
tttccttaag agtgggggaa cggaaagagg gagatgtgag cagcggcatc acctacgcta   5220
cttacggatt ttgctgccag ctaaacctag tccaacttaa agaatggata tccaggtact   5280
caatggtttt ttttgatgaa tatcacacag caactccaga acaaatagcc ataataagca   5340
agattcatgc actgaaagtt aagaccagga tagtggctat gtcagcaacc cccccgggta   5400
ccgtgacgac tgaaggcagg aagtttgaca ttgaagaggt aggggttgct accatagaga   5460
aaggagagga accaaaaagg gggcgcatag cggtcgctgg tatgcaggtc ccattagaag   5520
acttaacagg aaagaactgc ctggtgttcg tggcaaccaa agaagccgcg gagacggagg   5580
ctaaagaact gcgcaccaga ggaattaacg ccacctacta ctattcaggt atagacccta   5640
agactctgga acatgggatg accaatcagc catactgtat tgtagctacc aatgccattg   5700
aatcaggtat aacctgtcct gacttggatg tggtcataga caccatgcag aagtacgaaa   5760
aagtagtgaa tttctcggca aagatgccct tgattgtcac ttcattagta aagaaaaaaa   5820
tcaccaggga agaacagggc cagaggaaag gtcgagtggg caggcaaaag aaaggaaaat   5880
actactaccc ctcgggggtg gtaccgaatg ggtcaaaaga cctaagctat ttaatcctac   5940
aggcccaaga atatggtgtc ttggaacaag tcaatataac agagtacttc atcataatga   6000
atgaggactg ggtctctat gacgtagatg aagtagaagt gagaatactt gagagaatga   6060
acaaggaaat cttgctacca ctaggtattg tggagaagca aatcttggaa agaagtactc   6120
acccggaaaa agtggcactg ttgtataaca aattagtgca gaaaaatcct atagtatacc   6180
ctagagtaca ggaaggtgag gtcagcaagg aatacaatac ctataatctg gccgtatatg   6240
acaagctaaa agatgtcaac ccacaagcca tttatgttct agcagaagag gagagagcca   6300
cagaaatgat gggtctcgag tttgaacaag acccatctga cttacaggat tcggtagttc   6360
agctttgtga agatatcaag aggtatacaa aactctctgg gatcactgag aaactgctag   6420
taggtacgat ggtggggtat attggataca aagccttaac cagaaaccac gtgccctggg   6480
tcagcaaaga gtattgttat gagctgaccg attcaccgga tacttacgaa aactcattcg   6540
cacctttgga cgtcgacgtc caaaactccg gtgaaggaaa acacccagag caactggcag   6600
accatcaatt gaggcaacta ctggagactg ggagagacaa ggcaattgat ttcctaaaag   6660
gaatccgcga gttcactagt ggggccataa acagtccaaa ggcactaagt atatgggaga   6720
aaatatatca gtatttgaag aagcatcagg gcgagatcat ctcatcagca gcgtggggca   6780
gtgcgacggc ccttcacgac agtattaaat ctagactagg agatgaggtc gctactgcag   6840
taataatcct caagtattta gcatttggtg aaagagaact gtctgggcta actaggcaag   6900
ttctaattga catcatagta tattatatag ttaacaagcc ccggttcgaa ggagacgact   6960
acgcaaagag aaaaggaaga aggctagtca tcgaagtcct gatgggggca ctggcgactt   7020
atgcggtgtc caatttttgg ggtgtgtcca ttaataagat actgcaacca atttctgatt   7080
atctacccta tgccaccgcc actttggctt ttcttcgccc aaccttcatg gaatcagcag   7140
```

-continued

```
tggtggtcgc ttcctctatc tatagagctt ttctctccat taagcatgcg gaaaacagga   7200
gtcttgtcac gcaggtcgct tctgccgccc tcgaagtcat gggcctgacc ccagtatcgg   7260
ctggcctagg cgtcttgctg gggcttgggt tgtgtgtgct ccatatgaac attgacaaga   7320
atgaggagaa aaggacactt atactgaaaa tgtttgtcaa aaactttata gaccaggcgg   7380
cactagacga gttggataaa ctggagccag aaaaaataat cctctcattg ttggagggta   7440
tccaaacctg cacaaacccg attagagcaa tcatgatttt gtacagggtg tactacaagg   7500
gagaaacttt cacagaagct ttgtctaaga tggccggcaa gtctctcatt gtgatggtca   7560
tagtcgagtt cctggaattg acaggccaaa cccaaggagg gtatatagat cttagtgcta   7620
atttgctgac ctttctcctc gagaaactaa aaaaaatgac taacctcgcc atcggggaag   7680
ctagaaaggt cttgctcccc atcccatact tgtactgtga aacctggcag tctgacgcca   7740
gaatcaaggc ccctgaatcc tacgaccaag tggtagtgga atgcaaatgt ggcgcttcag   7800
cgaggtattc cttccgcgat ggagttcatg agatattgga agaaaaaagg actaattggt   7860
gcaagaactt cttcttatgg ggacccaact tccacaatcc ggatccaaaa aggatgacat   7920
tctatgaata cggccaagca aaaaagtgtc ctgttatcat aattggtgaa gacataacct   7980
tcggcaaata tggcatatat atcaaatttg gccataggcc tgatggaggg aggttaataa   8040
ggggtaccac ccacgctact atcagtaggg aggaattgct ggaaatccta acagccccaa   8100
gccaagtggc cataggcaag gtcaagctaa ccgattactg taatcaaaaa ggaataatag   8160
acaggaaatt ggccgtactt gaaggtgaca aaatacattt ttggaaagca caccgtggat   8220
ccaaaatcac agaccaactc actattgaga atctgacaga tgatttgggg tcagaaatca   8280
gggacatcac atgggagctg tacacaggtg gaacgtgcac cgtaaaaggg gtgtccctta   8340
gatcatgcgc accaggtcat agaactaagg ctatggtctt gtgtgattgc actgatgtgc   8400
ttagcccctg ttacctaata aacggcagga gaccatcccc atttgacgtc gcggaaggtt   8460
atgaatgtca ccaccggaag ccccgagcga cgtatgaaga cctagaaatg gaggaaatac   8520
taaagagacg agtccctgtc tacgatcctc tgtgtttgtt tgacactgat agtaaactgc   8580
tacctcccga cacctactac ttggaagaag atcaagagga ctttgagtac gcattgagat   8640
gctggggcct cggggtttat gtagcagacg ggcctgtcac ttcccccccg gacataagaa   8700
tacaccatag ttcggtatta ctactgctga cacctggagt aaactcagag ttgcccttac   8760
agtacatacg ttgttaccct catcaggcag aggtggacat ctacattagg agtcagcttt   8820
tggaggagga agacactgct acggaggtgg aaggctccca ggaagatggt gatgaaggga   8880
tgggcgatgc ggtaatagag gatgaggata catcgtccac aacagaatca ataccccccac   8940
tagaagagga ggaagggggc gaagagccaa tcacctatgt ggtcataagg ggattacaag   9000
aagaaagata cgccagccat cttaaactaa atgactggat cagtgaaaac atttcagagc   9060
cacacagagt ccaaattatg ctagatggga cagtgagagt cacaataaaa gagggcaaag   9120
tgaaacattt gtttggggtc tatagaatag aaaactccct ggaagcaatg tttaaagaga   9180
ccatagctga cctccccgta gctacccaac cgccccaggg gccagtctat acggctaaag   9240
agctggccca agggaacatc gccccggtcc aacctgcagc gaattattac ggaatgatag   9300
aggggagagg cgacccaatg acggcattcg aagccttatc agtcttgcgg tcacaaaaag   9360
tcttagccaa ggacgtgaag gtgaacaccc gcagggcgca ggttttttta aataaagtca   9420
ggagaattgc tgaggtcaga gcgtcggaac tgacattaaa atgcttaccg atacttggca   9480
aagtaaatgg gaggaaattg attagagagg aaaccaacat ccccaaccaa aggttggcat   9540
```

-continued caataatgac ctcaatagga attagactag aaaaactgcc agtggttaga gcaaacactt 9600
ccggctctaa gttcagacag tcaatcttag aaaaaatgga taagtatgaa aatgaacaag 9660
tcccagggtt acatgaaaag atgtgggcag cgttcctggc aactgccagg caagatttaa 9720
gaaataccta tgaggaagta acttatcttg aattagaggc cggaatcaat cggaaaggag 9780
ccccaggttt ctttgaaaaa gaaagctcaa taggagaagt gctggaaaaa aaagaaaaaa 9840
ttgacgtcac aatccaagag attgaaaaag gcaaccactt atactatgaa acagccatgc 9900
caaaaaatga gaaaagagat gtgcttgatg attggttgtc agaggatttc gtcacttata 9960
agaaaccacg tgtgatacag taccctgagg cagtcacccg gttggccatc accaaaataa 10020
tgtataagtg ggtgaagcaa aagcctatag tgattcccgg ttatgaggga aaaaccccga 10080
tctttgaaat atttgaaaaa gtcagtgcag attgggctca gttcaaaaat ccggtagccg 10140
tcagcttcga caccagagcc tgggacactc aagtaacaag agaagacctc aggctggtag 10200
ggcggataca gaaatactat tacaaaaaaa aatattggaa gttcattgac aatttgacag 10260
ccatgatgga ggaagtgcct gtaatcactg tagaaggaga tatgttcctc agagttggac 10320
agcgcggatc cggacagcct gatacctcag caggcaattc catgctaaat gtgctgacta 10380
tgttggtagc tttctctgaa tccacaaatc tgcccatagc ggctgcctgg aaggcctgtc 10440
ggatccacgt ctgtggtgac gacggtttct taatcacaga atcggaatta gggaggaagt 10500
ttgctgaaaa aggtgttcct ctgttagctg catttggcaa accccaaaaa attacagagg 10560
gagcgagcct aaaggtaacc agcaactttg acggaataga gttttgtagt cataccccta 10620
tcagagtcca aacaccaaac atcaggtgga tgccagcgag accaacagca acaatcctag 10680
gcaaaatgag taccaggctg ggtgagggtg ccaccaggtc gggagaagaa tacgaaaaac 10740
aggtggcatt cgcatatcta ctgatgtacc cctggaaccc gctggtcagg agaatcagcc 10800
tcctattgtt atcgactact gacccaatgg ggaaagagga aaccccatgc tccgatgagg 10860
gggtgaagta tgttggggac cctatcgctg catacaggga tgtatggggg cacaaattag 10920
aggatgtagg ccatgttgat caaccgcagt tatcccggat gaactatagc atgacttact 10980
tagggatttg gaaaccaaag acaagtcagc ggctagtcga acagtgttgt cgtctggccg 11040
agaaaagcaa ttgtgtggta cgtgctgact ccctgataaa gaaaaaggtc aagatcactt 11100
atgacccggg gataggagtg gctcaggtca ttcgtaggtg ggaagagctt gagtggacca 11160
gaaggaaacc tgaactcacc aatgtaattg tagaagatga tatcttccta gtcctgtgga 11220
agagattttc aaagtacatt tttcagaaaa tgaagttcat gcagagaatg ttcgcccctt 11280
attaagtggg gggcactcat ttaaattata accagtatct ggtaagtata agatttgtgt 11340
aaataaagta tataactgaa aggggcaagt ggccgtatag gctggggtga tcgccgcacc 11400
ccccccttca ctaggcgcct caaccccatg taccatgggg ttgttgtaaa tacttgaatg 11460
aatggagtaa tacgggtaac aaacttatag gccagtattg ccccatttgc tttatagtgg 11520
tgacgacctg tataggtccg atctgatatc 11550

<210> SEQ ID NO 2
<211> LENGTH: 3635
<212> TYPE: PRT
<213> ORGANISM: pestivirus type 2

<400> SEQUENCE: 2

Met Glu Lys Gln Ile Ala Tyr Tyr Leu Lys Lys Glu Lys Gln Arg Asn
1 5 10 15

```
Gly Trp Thr Glu Leu Val Val Gly Glu Ser His Thr Lys Ile Thr Thr
            20                  25                  30

Leu Ser Gly Lys Thr Tyr Arg Gly Thr Trp Glu Met Glu Lys Arg Pro
        35                  40                  45

Asn Pro Tyr Gly Thr Tyr Leu Pro Arg Pro Ser Pro Gln Gln Leu Thr
    50                  55                  60

Ala Leu His Pro His Pro Val Val Asn Cys Lys Val Val Glu Tyr Lys
65                  70                  75                  80

Glu Met Asp Pro Asn Tyr Gly Asp Cys Pro Asn Thr Asn Gly Val Phe
                85                  90                  95

Val Asp Glu Lys Gly Arg Arg Leu Ser Ser Pro Pro Leu Gly Ile Trp
            100                 105                 110

Lys Ile Arg Leu Asp Tyr Ser Asp Leu Val Asn Ile Ser Arg Pro Thr
        115                 120                 125

Pro Ala Ser Gly Lys Asn Ser Tyr Gln Val Glu Thr Cys Ser Gly Glu
    130                 135                 140

Leu Ala Thr Val Thr Leu Val His Asn Arg Val Leu Val Glu Asp Cys
145                 150                 155                 160

Arg Gly Leu Tyr Gln Trp Lys Pro Asn Cys Glu Gly Ile Val Leu Tyr
                165                 170                 175

Val Lys Thr Cys Ser Asp Trp Ala Asp Gln Val Glu Lys Gln Glu Lys
            180                 185                 190

Glu Ser Pro Pro Lys Pro Gln Arg Pro Pro Arg Arg Asp Pro Arg Lys
        195                 200                 205

Gly Leu Gln Pro Gln Val Pro Lys Glu Thr Glu Val Thr Glu Lys Lys
    210                 215                 220

Arg Gln Pro Ser Val Thr Leu Val Ser Gly Gly Gln Lys Ala Gln Val
225                 230                 235                 240

Ile Tyr Lys Gly Arg Thr Lys Asn Lys Lys Thr Pro Asp Gly Val Tyr
                245                 250                 255

Arg Tyr Pro Gly Ala Lys Glu Gly Asp Val Val Lys Val Arg Lys Met
            260                 265                 270

Leu Lys Asn Trp His Ile Ala Leu Val Met Tyr Leu Ile His Ile Ile
        275                 280                 285

Thr Pro Gly Leu Ala Lys Val Gln Trp Phe Leu Lys Asp Glu Asn Ser
    290                 295                 300

Thr Gly Ile Asn Gln Ile Leu Trp Gln Arg Gln Ile Asn Arg Ser Leu
305                 310                 315                 320

His Gly Glu Trp Pro Asn Gln Ile Cys His Gly Met Pro Asn Glu Thr
                325                 330                 335

Ile Thr Asp Glu Glu Leu Arg Ser Leu Gly Met Val Asp Thr Ser Pro
            340                 345                 350

Arg Thr Asn Tyr Thr Cys Cys Gln Leu Gln Tyr His Glu Trp Lys Lys
        355                 360                 365

His Gly Trp Cys Asn Tyr Pro Gln Lys Gln Ala Trp Ile Thr Arg Ile
    370                 375                 380

Thr Ala Leu Gln Ala Asn Leu Thr Gly Pro Tyr Glu Gly Pro Glu Cys
385                 390                 395                 400

Ala Val Ile Cys Arg Phe Asn Gly Ser Tyr Asn Ile Val Lys Gln Ala
                405                 410                 415

Arg Asp Glu Val Ser Pro Leu Thr Gly Cys Lys Glu Gly His Pro Phe
            420                 425                 430
```

-continued

```
Leu Phe Ser Gly Glu Arg Ser Asp Thr Ser Cys Leu Arg Pro Pro Ser
        435                 440                 445

Thr Ser Trp Val Arg Pro Val Lys Met Asp Glu Ala Ser Met Ala Asp
    450                 455                 460

Gly Phe Ala His Gly Val Asp Lys Ala Ile Ile Leu Ile Arg Lys Gly
465                 470                 475                 480

Ala Ser Gly Ile Ile Asn Phe Leu Asp Thr Ile Gly Arg Trp Leu Pro
                485                 490                 495

Val Ala Glu Ala Thr Ile Val Pro Tyr Cys Asp Thr Tyr Thr Val Thr
            500                 505                 510

Gly Met Tyr Val His Val Lys Asn Cys Leu Pro Arg Gly Leu Pro Lys
        515                 520                 525

His Ser Lys Ile Ile Ser Pro Thr Met Ile Tyr Leu Gly Glu Gly Asp
    530                 535                 540

Pro Ala His Asn Ile Gln His Leu Phe Gly Ser Gly Ile Ala Lys Trp
545                 550                 555                 560

Val Leu Val Leu Leu Gly Ile Leu Gly Glu Trp Tyr Gly Glu Leu Ala
                565                 570                 575

Ser Thr Ile Tyr Leu Leu Leu Glu Tyr Gly Ser Glu Trp Leu Glu His
            580                 585                 590

Glu Ser Leu Val Thr Glu Gly Leu Ile Pro Gly Ile Asn Ile Thr Ile
        595                 600                 605

Glu Leu Pro Ala Ser His Thr Val Pro Gly Trp Val Trp Val Ala Gly
    610                 615                 620

Gln Trp Val Cys Val Lys Pro Asp Trp Trp Pro Thr Gln Ile Trp Ile
625                 630                 635                 640

Glu Thr Val Val Ala Glu Thr Trp His Ile Leu Lys Ile Leu Ala Ser
                645                 650                 655

Ala Leu Val Asn Ile Val Ala Ala Phe Val Asn Leu Glu Leu Val Tyr
            660                 665                 670

Leu Val Ile Ile Leu Val Lys Ile Ser Lys Gly Asn Leu Ile Gly Ala
        675                 680                 685

Ile Leu Trp Cys Leu Leu Leu Ser Gly Ala Glu Gly Ser Cys Tyr Lys
    690                 695                 700

Arg Gln Asp Tyr Tyr Asn Thr Gln Leu Val Val Glu Glu Lys Thr Gly
705                 710                 715                 720

Val Glu Lys Arg Ser Ile Met Gly Lys Trp Thr Val Ile Thr Arg Glu
                725                 730                 735

Gly Arg Glu Pro Arg Leu Met Glu Gln Ile Asn Met Val Leu Asn Asp
            740                 745                 750

Ser Leu Ser Glu Thr Tyr Cys Tyr Asn Arg Leu Asn Thr Ser Thr Trp
        755                 760                 765

Gly Arg Gln Pro Ala Arg Gln Arg Gly Cys Gly Gln Thr Val Pro Tyr
    770                 775                 780

Trp Pro Gly Asp Asn Val Leu Glu Glu Gln Tyr Tyr Ser Thr Gly Tyr
785                 790                 795                 800

Trp Val Asn Val Thr Gly Gly Cys Gln Leu Arg Glu Gly Val Trp Leu
                805                 810                 815

Ser Arg Lys Gly Asn Val Gln Cys Gln Arg Asn Gly Ser Ser Leu Met
            820                 825                 830

Leu Gln Leu Ala Ile Lys Glu Glu Asn Asp Thr Met Glu Ile Pro Cys
        835                 840                 845

Asp Pro Val Glu Thr Glu Ser Met Gly Pro Val Ala Gln Gly Thr Cys
```

```
    850                 855                 860

Val Tyr Ser Trp Ala Phe Ala Pro Arg Gly Trp Tyr Tyr Asn Arg Lys
865                 870                 875                 880

Asp Gly Tyr Trp Leu Gln Tyr Ile Lys Lys Asn Asp Tyr Gln Tyr Trp
                885                 890                 895

Thr Lys Met Pro Thr Ala Ser Ser Ala Ala Thr Met Tyr Arg His Leu
            900                 905                 910

Leu Pro Leu Leu Val Ala Cys Leu Met Gly Gly Arg Ile Ser Val Trp
        915                 920                 925

Phe Val Ala Met Leu Leu Ser Leu Gln Val Glu Ala Ser Glu Val Gly
    930                 935                 940

Thr Lys Gln Leu Ala Val Thr Leu Thr Leu Trp Lys Met Asp Trp Thr
945                 950                 955                 960

Glu Leu Leu Phe Tyr Ile Val Leu Met Leu Ala Val Lys Glu Glu Leu
                965                 970                 975

Ile Lys Lys Ile Val Thr Ala Ser Leu Val Ala Leu Lys Asn Ser Pro
            980                 985                 990

Val Ala Leu Ser Phe Leu Ile Val  Leu Arg Leu Val Gly  Gly Ser Glu
        995                 1000                1005

Ala Leu  Pro Val Gly Leu Leu  Leu Glu Lys Met Cys  Ile Asp Gln
    1010                1015                1020

Pro Glu  Phe Gly Thr Pro Phe  Leu Ile Tyr Leu Trp  Asp Asn Trp
    1025                1030                1035

Lys Trp  Thr Val Leu Val Ser  Phe Ser Ala Leu Asn  His Glu Lys
    1040                1045                1050

Thr Ile  Lys Leu Ala Arg Lys  Leu Leu Leu Ala Thr  His Ile Thr
    1055                1060                1065

Ala Leu  Thr Leu Thr Gly Leu  Ser Asp Ser Ile Phe  Tyr Met Met
    1070                1075                1080

Leu Ile  Thr Thr Asn Leu Leu  Ile Lys Thr Phe Ile  Tyr Leu Leu
    1085                1090                1095

Gly Ala  Ser Met Asn Trp Val  Glu Arg Glu Lys Lys  Lys Leu Leu
    1100                1105                1110

Val Lys  Arg Arg Leu Ile Tyr  Lys Lys Ala Val Thr  Cys Ser Gln
    1115                1120                1125

Asp Glu  Asn Val Leu Glu Asn  Lys Phe Asn Lys Ile  Thr Val Asn
    1130                1135                1140

Ala Asp  Phe Thr Pro Cys Lys  Leu Glu Leu Leu Gln  Leu Leu Arg
    1145                1150                1155

Ala Phe  Leu Val Ser Leu Cys  Phe Ser Tyr Tyr Lys  Pro Leu Leu
    1160                1165                1170

Tyr Ala  Glu Thr Thr Leu Thr  Val Ile Val Ile Gly  Val Gln Glu
    1175                1180                1185

Tyr Asn  Val Ala Met Ala Arg  Gly Arg Ser Val Val  His Arg Leu
    1190                1195                1200

Leu Ala  Met Ala Tyr Tyr Ile  Tyr Gly Arg Ile Gln  Gly Asp Met
    1205                1210                1215

Phe Gln  Leu Ala Thr Ile Gln  Cys Leu Leu Ser Ser  Pro Arg Lys
    1220                1225                1230

Ile Met  Lys His Met Val Glu  Asn Pro Thr Leu Lys  Lys Leu Trp
    1235                1240                1245

Gln Gly  Glu Thr Glu Leu Phe  Asn Gln Gly Val Ser  Gln Ser Lys
    1250                1255                1260
```

-continued

```
Ile Val  Asn Pro Lys Lys Ile  Gly Leu Glu Glu Leu  His Lys Gly
    1265                 1270                 1275

Met Cys  Gly Leu Pro Thr Val  Val Gln Asn Leu Val  Ile Tyr Ala
    1280                 1285                 1290

Lys Lys  Asn Asp Ser Leu Ile  Leu Gly Glu Leu Gly  Tyr Pro Pro
    1295                 1300                 1305

Gly Asp  Leu Thr Ser Asp Gly  Trp Glu Ile Leu Gly  Pro Gly Arg
    1310                 1315                 1320

Ile Pro  Lys Ile Thr Asn Val  Glu Ser Ala Lys Met  Asp Leu Leu
    1325                 1330                 1335

Ser Lys  Leu Met Thr Phe Leu  Gly Ile Glu Ser Ser  Arg Val Pro
    1340                 1345                 1350

Arg Thr  Pro Val His Ser Thr  Arg Lys Leu Leu Lys  Ile Val Arg
    1355                 1360                 1365

Gly Leu  Glu Thr Gly Trp Gly  Tyr Thr His Ala Gly  Gly Ile Ser
    1370                 1375                 1380

Ser Ala  Lys His Val Thr Gly  Glu Lys Asn Leu Met  Thr His Met
    1385                 1390                 1395

Glu Gly  Arg Lys Gly Lys Tyr  Ile Leu Gln Ser Gln  Glu His Gly
    1400                 1405                 1410

Ala Asp  Glu Val Glu Tyr Gly  Val Lys Thr Asp Gln  Lys Ala Pro
    1415                 1420                 1425

Asp Asn  Ala Leu Cys Tyr Cys  Phe Asn Pro Glu Ala  Thr Asn Ile
    1430                 1435                 1440

Lys Gly  Glu Thr Gly Ala Met  Val Phe Met Lys Lys  Ile Gly Lys
    1445                 1450                 1455

Lys Trp  Thr Leu Val Thr Ser  Asp Gly Asn Lys Ala  Tyr Tyr Asn
    1460                 1465                 1470

Val Asn  Asn Leu Lys Gly Trp  Ser Gly Leu Pro Ile  Met Leu His
    1475                 1480                 1485

Ser Thr  Gly Ala Ile Val Gly  Arg Ile Lys Ser Ala  Tyr Ser Asp
    1490                 1495                 1500

Glu Asn  Asp Leu Val Glu Glu  Leu Ile Asp Ser Arg  Thr Ile Ser
    1505                 1510                 1515

Lys Ser  Asn Glu Thr Asn Leu  Asp His Leu Ile Lys  Glu Leu Ala
    1520                 1525                 1530

Asp Met  Arg Arg Gly Glu Phe  Arg Ser Ile Thr Leu  Gly Thr Gly
    1535                 1540                 1545

Ala Gly  Lys Thr Thr Glu Leu  Pro Arg Gln Tyr Leu  Thr Thr Val
    1550                 1555                 1560

Gly Ala  His Lys Ser Val Leu  Val Leu Val Pro Leu  Lys Ala Pro
    1565                 1570                 1575

Ala Glu  Ser Val Cys Arg Phe  Met Arg Ser Lys Tyr  Pro Thr Ile
    1580                 1585                 1590

Asn Phe  Ser Leu Arg Val Gly  Glu Arg Lys Glu Gly  Asp Val Ser
    1595                 1600                 1605

Ser Gly  Ile Thr Tyr Ala Thr  Tyr Gly Phe Cys Cys  Gln Leu Asn
    1610                 1615                 1620

Leu Val  Gln Leu Lys Glu Trp  Ile Ser Arg Tyr Ser  Met Val Phe
    1625                 1630                 1635

Phe Asp  Glu Tyr His Thr Ala  Thr Pro Glu Gln Ile  Ala Ile Ile
    1640                 1645                 1650
```

```
Ser Lys Ile His Ala Leu Lys Val Lys Thr Arg Ile Val Ala Met
    1655                1660                1665

Ser Ala Thr Pro Pro Gly Thr Val Thr Thr Glu Gly Arg Lys Phe
    1670                1675                1680

Asp Ile Glu Glu Val Gly Val Ala Thr Ile Glu Lys Gly Glu Glu
    1685                1690                1695

Pro Lys Arg Gly Arg Ile Ala Val Ala Gly Met Gln Val Pro Leu
    1700                1705                1710

Glu Asp Leu Thr Gly Lys Asn Cys Leu Val Phe Val Ala Thr Lys
    1715                1720                1725

Glu Ala Ala Glu Thr Glu Ala Lys Glu Leu Arg Thr Arg Gly Ile
    1730                1735                1740

Asn Ala Thr Tyr Tyr Tyr Ser Gly Ile Asp Pro Lys Thr Leu Glu
    1745                1750                1755

His Gly Met Thr Asn Gln Pro Tyr Cys Ile Val Ala Thr Asn Ala
    1760                1765                1770

Ile Glu Ser Gly Ile Thr Cys Pro Asp Leu Asp Val Val Ile Asp
    1775                1780                1785

Thr Met Gln Lys Tyr Glu Lys Val Val Asn Phe Ser Ala Lys Met
    1790                1795                1800

Pro Leu Ile Val Thr Ser Leu Val Lys Lys Lys Ile Thr Arg Glu
    1805                1810                1815

Glu Gln Gly Gln Arg Lys Gly Arg Val Gly Arg Gln Lys Lys Gly
    1820                1825                1830

Lys Tyr Tyr Tyr Pro Ser Gly Val Val Pro Asn Gly Ser Lys Asp
    1835                1840                1845

Leu Ser Tyr Leu Ile Leu Gln Ala Gln Glu Tyr Gly Val Leu Glu
    1850                1855                1860

Gln Val Asn Ile Thr Glu Tyr Phe Ile Ile Met Asn Glu Asp Trp
    1865                1870                1875

Gly Leu Tyr Asp Val Asp Glu Val Glu Val Arg Ile Leu Glu Arg
    1880                1885                1890

Met Asn Lys Glu Ile Leu Leu Pro Leu Gly Ile Val Glu Lys Gln
    1895                1900                1905

Ile Leu Glu Arg Ser Thr His Pro Glu Lys Val Ala Leu Leu Tyr
    1910                1915                1920

Asn Lys Leu Val Gln Lys Asn Pro Ile Val Tyr Pro Arg Val Gln
    1925                1930                1935

Glu Gly Glu Val Ser Lys Glu Tyr Asn Thr Tyr Asn Leu Ala Val
    1940                1945                1950

Tyr Asp Lys Leu Lys Asp Val Asn Pro Gln Ala Ile Tyr Val Leu
    1955                1960                1965

Ala Glu Glu Glu Arg Ala Thr Glu Met Met Gly Leu Glu Phe Glu
    1970                1975                1980

Gln Asp Pro Ser Asp Leu Gln Asp Ser Val Val Gln Leu Cys Glu
    1985                1990                1995

Asp Ile Lys Arg Tyr Thr Lys Leu Ser Gly Ile Thr Glu Lys Leu
    2000                2005                2010

Leu Val Gly Thr Met Val Gly Tyr Ile Gly Tyr Lys Ala Leu Thr
    2015                2020                2025

Arg Asn His Val Pro Trp Val Ser Lys Glu Tyr Cys Tyr Glu Leu
    2030                2035                2040

Thr Asp Ser Pro Asp Thr Tyr Glu Asn Ser Phe Ala Pro Leu Asp
```

-continued

```
    2045                2050                2055

Val Asp  Val Gln Asn Ser Gly  Glu Gly Lys His Pro  Glu Gln Leu
    2060                2065                2070

Ala Asp  His Gln Leu Arg Gln  Leu Leu Glu Thr Gly  Arg Asp Lys
    2075                2080                2085

Ala Ile  Asp Phe Leu Lys Gly  Ile Arg Glu Phe Thr  Ser Gly Ala
    2090                2095                2100

Ile Asn  Ser Pro Lys Ala Leu  Ser Ile Trp Glu Lys  Ile Tyr Gln
    2105                2110                2115

Tyr Leu  Lys Lys His Gln Gly  Glu Ile Ile Ser Ser  Ala Ala Trp
    2120                2125                2130

Gly Ser  Ala Thr Ala Leu His  Asp Ser Ile Lys Ser  Arg Leu Gly
    2135                2140                2145

Asp Glu  Val Ala Thr Ala Val  Ile Ile Leu Lys Tyr  Leu Ala Phe
    2150                2155                2160

Gly Glu  Arg Glu Leu Ser Gly  Leu Thr Arg Gln Val  Leu Ile Asp
    2165                2170                2175

Ile Ile  Val Tyr Tyr Ile Val  Asn Lys Pro Arg Phe  Glu Gly Asp
    2180                2185                2190

Asp Tyr  Ala Lys Arg Lys Gly  Arg Arg Leu Val Ile  Glu Val Leu
    2195                2200                2205

Met Gly  Ala Leu Ala Thr Tyr  Ala Val Ser Asn Phe  Trp Gly Val
    2210                2215                2220

Ser Ile  Asn Lys Ile Leu Gln  Pro Ile Ser Asp Tyr  Leu Pro Tyr
    2225                2230                2235

Ala Thr  Ala Thr Leu Ala Phe  Leu Arg Pro Thr Phe  Met Glu Ser
    2240                2245                2250

Ala Val  Val Val Ala Ser Ser  Ile Tyr Arg Ala Phe  Leu Ser Ile
    2255                2260                2265

Lys His  Ala Glu Asn Arg Ser  Leu Val Thr Gln Val  Ala Ser Ala
    2270                2275                2280

Ala Leu  Glu Val Met Gly Leu  Thr Pro Val Ser Ala  Gly Leu Gly
    2285                2290                2295

Val Leu  Leu Gly Leu Gly Leu  Cys Val Leu His Met  Asn Ile Asp
    2300                2305                2310

Lys Asn  Glu Glu Lys Arg Thr  Leu Ile Leu Lys Met  Phe Val Lys
    2315                2320                2325

Asn Phe  Ile Asp Gln Ala Ala  Leu Asp Glu Leu Asp  Lys Leu Glu
    2330                2335                2340

Pro Glu  Lys Ile Ile Leu Ser  Leu Leu Glu Gly Ile  Gln Thr Cys
    2345                2350                2355

Thr Asn  Pro Ile Arg Ala Ile  Met Ile Leu Tyr Arg  Val Tyr Tyr
    2360                2365                2370

Lys Gly  Glu Thr Phe Thr Glu  Ala Leu Ser Lys Met  Ala Gly Lys
    2375                2380                2385

Ser Leu  Ile Val Met Val Ile  Val Glu Phe Leu Glu  Leu Thr Gly
    2390                2395                2400

Gln Thr  Gln Gly Gly Tyr Ile  Asp Leu Ser Ala Asn  Leu Leu Thr
    2405                2410                2415

Phe Leu  Leu Glu Lys Leu Lys  Lys Met Thr Asn Leu  Ala Ile Gly
    2420                2425                2430

Glu Ala  Arg Lys Val Leu Leu  Pro Ile Pro Tyr Leu  Tyr Cys Glu
    2435                2440                2445
```

```
Thr Trp Gln Ser Asp Ala Arg Ile Lys Ala Pro Glu Ser Tyr Asp
    2450                2455                2460

Gln Val Val Val Glu Cys Lys Cys Gly Ala Ser Ala Arg Tyr Ser
    2465                2470                2475

Phe Arg Asp Gly Val His Glu Ile Leu Glu Glu Lys Arg Thr Asn
    2480                2485                2490

Trp Cys Lys Asn Phe Phe Leu Trp Gly Pro Asn Phe His Asn Pro
    2495                2500                2505

Asp Pro Lys Arg Met Thr Phe Tyr Glu Tyr Gly Gln Ala Lys Lys
    2510                2515                2520

Cys Pro Val Ile Ile Ile Gly Glu Asp Ile Thr Phe Gly Lys Tyr
    2525                2530                2535

Gly Ile Tyr Ile Lys Phe Gly His Arg Pro Asp Gly Gly Arg Leu
    2540                2545                2550

Ile Arg Gly Thr Thr His Ala Thr Ile Ser Arg Glu Glu Leu Leu
    2555                2560                2565

Glu Ile Leu Thr Ala Pro Ser Gln Val Ala Ile Gly Lys Val Lys
    2570                2575                2580

Leu Thr Asp Tyr Cys Asn Gln Lys Gly Ile Ile Asp Arg Lys Leu
    2585                2590                2595

Ala Val Leu Glu Gly Asp Lys Ile His Phe Trp Lys Ala His Arg
    2600                2605                2610

Gly Ser Lys Ile Thr Asp Gln Leu Thr Ile Glu Asn Leu Thr Asp
    2615                2620                2625

Asp Leu Gly Ser Glu Ile Arg Asp Ile Thr Trp Glu Leu Tyr Thr
    2630                2635                2640

Gly Gly Thr Cys Thr Val Lys Gly Val Ser Leu Arg Ser Cys Ala
    2645                2650                2655

Pro Gly His Arg Thr Lys Ala Met Val Leu Cys Asp Cys Thr Asp
    2660                2665                2670

Val Leu Ser Pro Cys Tyr Leu Ile Asn Gly Arg Arg Pro Ser Pro
    2675                2680                2685

Phe Asp Val Ala Glu Gly Tyr Glu Cys His His Arg Lys Pro Arg
    2690                2695                2700

Ala Thr Tyr Glu Asp Leu Glu Met Glu Glu Ile Leu Lys Arg Arg
    2705                2710                2715

Val Pro Val Tyr Asp Pro Leu Cys Leu Phe Asp Thr Asp Ser Lys
    2720                2725                2730

Leu Leu Pro Pro Asp Thr Tyr Tyr Leu Glu Glu Asp Gln Glu Asp
    2735                2740                2745

Phe Glu Tyr Ala Leu Arg Cys Trp Gly Leu Gly Val Tyr Val Ala
    2750                2755                2760

Asp Gly Pro Val Thr Ser Pro Pro Asp Ile Arg Ile His His Ser
    2765                2770                2775

Ser Val Leu Leu Leu Leu Thr Pro Gly Val Asn Ser Glu Leu Pro
    2780                2785                2790

Leu Gln Tyr Ile Arg Cys Tyr Pro His Gln Ala Glu Val Asp Ile
    2795                2800                2805

Tyr Ile Arg Ser Gln Leu Leu Glu Glu Glu Asp Thr Ala Thr Glu
    2810                2815                2820

Val Glu Gly Ser Gln Glu Asp Gly Asp Glu Gly Met Gly Asp Ala
    2825                2830                2835
```

-continued

```
Val Ile  Glu Asp Glu Asp Thr  Ser Ser Thr Thr Glu  Ser Ile Pro
    2840                 2845                 2850

Pro Leu  Glu Glu Glu Glu Gly  Gly Glu Glu Pro Ile  Thr Tyr Val
    2855                 2860                 2865

Val Ile  Arg Gly Leu Gln Glu  Glu Arg Tyr Ala Ser  His Leu Lys
    2870                 2875                 2880

Leu Asn  Asp Trp Ile Ser Glu  Asn Ile Ser Glu Pro  His Arg Val
    2885                 2890                 2895

Gln Ile  Met Leu Asp Gly Thr  Val Arg Val Thr Ile  Lys Glu Gly
    2900                 2905                 2910

Lys Val  Lys His Leu Phe Gly  Val Tyr Arg Ile Glu  Asn Ser Leu
    2915                 2920                 2925

Glu Ala  Met Phe Lys Glu Thr  Ile Ala Asp Leu Pro  Val Ala Thr
    2930                 2935                 2940

Gln Pro  Pro Gln Gly Pro Val  Tyr Thr Ala Lys Glu  Leu Ala Gln
    2945                 2950                 2955

Gly Asn  Ile Ala Pro Val Gln  Pro Ala Ala Asn Tyr  Tyr Gly Met
    2960                 2965                 2970

Ile Glu  Gly Arg Gly Asp Pro  Met Thr Ala Phe Glu  Ala Leu Ser
    2975                 2980                 2985

Val Leu  Arg Ser Gln Lys Val  Leu Ala Lys Asp Val  Lys Val Asn
    2990                 2995                 3000

Thr Arg  Arg Ala Gln Val Phe  Leu Asn Lys Val Arg  Arg Ile Ala
    3005                 3010                 3015

Glu Val  Arg Ala Ser Glu Leu  Thr Leu Lys Cys Leu  Pro Ile Leu
    3020                 3025                 3030

Gly Lys  Val Asn Gly Arg Lys  Leu Ile Arg Glu Glu  Thr Asn Ile
    3035                 3040                 3045

Pro Asn  Gln Arg Leu Ala Ser  Ile Met Thr Ser Ile  Gly Ile Arg
    3050                 3055                 3060

Leu Glu  Lys Leu Pro Val Val  Arg Ala Asn Thr Ser  Gly Ser Lys
    3065                 3070                 3075

Phe Arg  Gln Ser Ile Leu Glu  Lys Met Asp Lys Tyr  Glu Asn Glu
    3080                 3085                 3090

Gln Val  Pro Gly Leu His Glu  Lys Met Trp Ala Ala  Phe Leu Ala
    3095                 3100                 3105

Thr Ala  Arg Gln Asp Leu Arg  Asn Thr Tyr Glu Glu  Val Thr Tyr
    3110                 3115                 3120

Leu Glu  Leu Glu Ala Gly Ile  Asn Arg Lys Gly Ala  Pro Gly Phe
    3125                 3130                 3135

Phe Glu  Lys Glu Ser Ser Ile  Gly Glu Val Leu Glu  Lys Lys Glu
    3140                 3145                 3150

Lys Ile  Asp Val Thr Ile Gln  Glu Ile Glu Lys Gly  Asn His Leu
    3155                 3160                 3165

Tyr Tyr  Glu Thr Ala Met Pro  Lys Asn Glu Lys Arg  Asp Val Leu
    3170                 3175                 3180

Asp Asp  Trp Leu Ser Glu Asp  Phe Val Thr Tyr Lys  Lys Pro Arg
    3185                 3190                 3195

Val Ile  Gln Tyr Pro Glu Ala  Val Thr Arg Leu Ala  Ile Thr Lys
    3200                 3205                 3210

Ile Met  Tyr Lys Trp Val Lys  Gln Lys Pro Ile Val  Ile Pro Gly
    3215                 3220                 3225

Tyr Glu  Gly Lys Thr Pro Ile  Phe Glu Ile Phe Glu  Lys Val Ser
```

```
    3230                3235                3240

Ala Asp  Trp Ala Gln Phe Lys  Asn Pro Val Ala Val  Ser Phe Asp
    3245                3250                3255

Thr Arg  Ala Trp Asp Thr Gln  Val Thr Arg Glu Asp  Leu Arg Leu
    3260                3265                3270

Val Gly  Arg Ile Gln Lys Tyr  Tyr Tyr Lys Lys Lys  Tyr Trp Lys
    3275                3280                3285

Phe Ile  Asp Asn Leu Thr Ala  Met Met Glu Glu Val  Pro Val Ile
    3290                3295                3300

Thr Val  Glu Gly Asp Met Phe  Leu Arg Val Gly Gln  Arg Gly Ser
    3305                3310                3315

Gly Gln  Pro Asp Thr Ser Ala  Gly Asn Ser Met Leu  Asn Val Leu
    3320                3325                3330

Thr Met  Leu Val Ala Phe Ser  Glu Ser Thr Asn Leu  Pro Ile Ala
    3335                3340                3345

Ala Ala  Trp Lys Ala Cys Arg  Ile His Val Cys Gly  Asp Asp Gly
    3350                3355                3360

Phe Leu  Ile Thr Glu Ser Glu  Leu Gly Arg Lys Phe  Ala Glu Lys
    3365                3370                3375

Gly Val  Pro Leu Leu Ala Ala  Phe Gly Lys Pro Gln  Lys Ile Thr
    3380                3385                3390

Glu Gly  Ala Ser Leu Lys Val  Thr Ser Asn Phe Asp  Gly Ile Glu
    3395                3400                3405

Phe Cys  Ser His Thr Pro Ile  Arg Val Gln Thr Pro  Asn Ile Arg
    3410                3415                3420

Trp Met  Pro Ala Arg Pro Thr  Ala Thr Ile Leu Gly  Lys Met Ser
    3425                3430                3435

Thr Arg  Leu Gly Glu Gly Ala  Thr Arg Ser Gly Glu  Glu Tyr Glu
    3440                3445                3450

Lys Gln  Val Ala Phe Ala Tyr  Leu Leu Met Tyr Pro  Trp Asn Pro
    3455                3460                3465

Leu Val  Arg Arg Ile Ser Leu  Leu Leu Leu Ser Thr  Thr Asp Pro
    3470                3475                3480

Met Gly  Lys Glu Glu Thr Pro  Cys Ser Asp Glu Gly  Val Lys Tyr
    3485                3490                3495

Val Gly  Asp Pro Ile Ala Ala  Tyr Arg Asp Val Trp  Gly His Lys
    3500                3505                3510

Leu Glu  Asp Val Gly His Val  Asp Gln Pro Gln Leu  Ser Arg Met
    3515                3520                3525

Asn Tyr  Ser Met Thr Tyr Leu  Gly Ile Trp Lys Pro  Lys Thr Ser
    3530                3535                3540

Gln Arg  Leu Val Glu Gln Cys  Cys Arg Leu Ala Glu  Lys Ser Asn
    3545                3550                3555

Cys Val  Val Arg Ala Asp Ser  Leu Ile Lys Lys Lys  Val Lys Ile
    3560                3565                3570

Thr Tyr  Asp Pro Gly Ile Gly  Val Ala Gln Val Ile  Arg Arg Trp
    3575                3580                3585

Glu Glu  Leu Glu Trp Thr Arg  Arg Lys Pro Glu Leu  Thr Asn Val
    3590                3595                3600

Ile Val  Glu Asp Asp Ile Phe  Leu Val Leu Trp Lys  Arg Phe Ser
    3605                3610                3615

Lys Tyr  Ile Phe Gln Lys Met  Lys Phe Met Gln Arg  Met Phe Ala
    3620                3625                3630
```

Pro Tyr
3635

<210> SEQ ID NO 3
<211> LENGTH: 540
<212> TYPE: DNA
<213> ORGANISM: pestivirus type 2

<400> SEQUENCE: 3
atggaaaaac agattgcata ttacttaaaa aaagaaaaac aaagaaatgg gtggacggaa 60
ctggtggtag gagaaagtca tacaaaaata accacgcttt ctggaaagac ctatcgaggc 120
acctgggaaa tggagaaacg gccaaatcct tatggaacct atctccccag acctagtccc 180
caacagctta cagccctaca cccccaccca gtggtgaatt gtaaggtggt tgagtacaag 240
gagatggacc ctaattatgg tgattgccca aatacgaacg gggtgtttgt tgacgaaaag 300
ggtagaaggc tgagcagccc tccattaggc atttggaaga taagattgga ctatagtgac 360
ttggtaaaca taagcagacc aacccccgct agtgggaaaa actcttacca agttgagacc 420
tgcagtgggg agctggctac agtgacactg gtacacaata gggtgctcgt ggaagattgc 480
agggggctat accaatggaa acccaactgt gaaggaattg tgctctatgt gaaaacttgt 540

<210> SEQ ID NO 4
<211> LENGTH: 180
<212> TYPE: PRT
<213> ORGANISM: pestivirus type 2

<400> SEQUENCE: 4

Met Glu Lys Gln Ile Ala Tyr Tyr Leu Lys Lys Glu Lys Gln Arg Asn
1 5 10 15

Gly Trp Thr Glu Leu Val Val Gly Glu Ser His Thr Lys Ile Thr Thr
20 25 30

Leu Ser Gly Lys Thr Tyr Arg Gly Thr Trp Glu Met Glu Lys Arg Pro
35 40 45

Asn Pro Tyr Gly Thr Tyr Leu Pro Arg Pro Ser Pro Gln Gln Leu Thr
50 55 60

Ala Leu His Pro His Pro Val Val Asn Cys Lys Val Val Glu Tyr Lys
65 70 75 80

Glu Met Asp Pro Asn Tyr Gly Asp Cys Pro Asn Thr Asn Gly Val Phe
85 90 95

Val Asp Glu Lys Gly Arg Arg Leu Ser Ser Pro Pro Leu Gly Ile Trp
100 105 110

Lys Ile Arg Leu Asp Tyr Ser Asp Leu Val Asn Ile Ser Arg Pro Thr
115 120 125

Pro Ala Ser Gly Lys Asn Ser Tyr Gln Val Glu Thr Cys Ser Gly Glu
130 135 140

Leu Ala Thr Val Thr Leu Val His Asn Arg Val Leu Val Glu Asp Cys
145 150 155 160

Arg Gly Leu Tyr Gln Trp Lys Pro Asn Cys Glu Gly Ile Val Leu Tyr
165 170 175

Val Lys Thr Cys
180

<210> SEQ ID NO 5
<211> LENGTH: 333
<212> TYPE: DNA
<213> ORGANISM: pestivirus type 2

<400> SEQUENCE: 5
tctgactggg cagatcaggt agaaaaacag gagaaagaaa gcccccccaaa accacagcgg 60 ccaccaaggc gagacccacg aaaagggtta caaccacaag tccccaaaga gactgaggtc 120
acagaaaaga agagacaacc tagtgtcacc ttagtatcgg gggggcagaa ggcccaagtc 180
atctacaaag gcaggaccaa aaacaaaaag accccggatg gagtctatag atacccagga 240
gctaaagaag ggacgtagt aaaggtcagg aagatgctga agaattggca tatagcctta 300
gtgatgtacc tgatacatat cataactcca ggc 333

<210> SEQ ID NO 6
<211> LENGTH: 111
<212> TYPE: PRT
<213> ORGANISM: pestivirus type 2

<400> SEQUENCE: 6

Ser Asp Trp Ala Asp Gln Val Glu Lys Gln Glu Lys Glu Ser Pro Pro
1 5 10 15

Lys Pro Gln Arg Pro Pro Arg Arg Asp Pro Arg Lys Gly Leu Gln Pro
20 25 30

Gln Val Pro Lys Glu Thr Glu Val Thr Glu Lys Lys Arg Gln Pro Ser
35 40 45

Val Thr Leu Val Ser Gly Gly Gln Lys Ala Gln Val Ile Tyr Lys Gly
50 55 60

Arg Thr Lys Asn Lys Lys Thr Pro Asp Gly Val Tyr Arg Tyr Pro Gly
65 70 75 80

Ala Lys Glu Gly Asp Val Val Lys Val Arg Lys Met Leu Lys Asn Trp
85 90 95

His Ile Ala Leu Val Met Tyr Leu Ile His Ile Ile Thr Pro Gly
100 105 110

<210> SEQ ID NO 7
<211> LENGTH: 627
<212> TYPE: DNA
<213> ORGANISM: pestivirus type 2

<400> SEQUENCE: 7
cttgccaagg tccagtggtt cttaaaagat gaaaactcga cggggatcaa ccagatactg 60
tggcaaagac agatcaacag atccttacat ggagaatggc ctaaccagat ctgccacggt 120
atgcccaatg aaactatcac ggatgaggaa ttacgcagtc tgggaatggt agatacaagc 180
cctagaacaa actacacctg ttgccagttg caatatcatg agtggaagaa acatggttgg 240
tgcaactatc cacaaaaaca ggcgtggatc acgaggataa cggccctaca agctaacctt 300
accgggcctt atgagggacc tgagtgcgcc gtcatctgcc gatttaacgg cagctacaac 360
atcgtaaaac aggccagaga tgaggtgagt ccactgacag ggtgcaagga agggcatcct 420
tttctattct ctggtgaaag atccgacacc tcatgcctaa ggcccccttc cactagttgg 480
gtaagaccag tgaaaatgga cgaggcatca atggccgatg gctttgccca tggggttgat 540
aaggcgataa tactaatcag gaagggggca tcaggaataa tcaatttcct agacactatt 600
gggaggtggc taccggtagc tgaagca 627

<210> SEQ ID NO 8
<211> LENGTH: 209
<212> TYPE: PRT
<213> ORGANISM: pestivirus type 2

-continued

<400> SEQUENCE: 8

Leu Ala Lys Val Gln Trp Phe Leu Lys Asp Glu Asn Ser Thr Gly Ile
1 5 10 15

Asn Gln Ile Leu Trp Gln Arg Gln Ile Asn Arg Ser Leu His Gly Glu
20 25 30

Trp Pro Asn Gln Ile Cys His Gly Met Pro Asn Glu Thr Ile Thr Asp
35 40 45

Glu Glu Leu Arg Ser Leu Gly Met Val Asp Thr Ser Pro Arg Thr Asn
50 55 60

Tyr Thr Cys Cys Gln Leu Gln Tyr His Glu Trp Lys Lys His Gly Trp
65 70 75 80

Cys Asn Tyr Pro Gln Lys Gln Ala Trp Ile Thr Arg Ile Thr Ala Leu
85 90 95

Gln Ala Asn Leu Thr Gly Pro Tyr Glu Gly Pro Glu Cys Ala Val Ile
100 105 110

Cys Arg Phe Asn Gly Ser Tyr Asn Ile Val Lys Gln Ala Arg Asp Glu
115 120 125

Val Ser Pro Leu Thr Gly Cys Lys Glu Gly His Pro Phe Leu Phe Ser
130 135 140

Gly Glu Arg Ser Asp Thr Ser Cys Leu Arg Pro Pro Ser Thr Ser Trp
145 150 155 160

Val Arg Pro Val Lys Met Asp Glu Ala Ser Met Ala Asp Gly Phe Ala
165 170 175

His Gly Val Asp Lys Ala Ile Ile Leu Ile Arg Lys Gly Ala Ser Gly
180 185 190

Ile Ile Asn Phe Leu Asp Thr Ile Gly Arg Trp Leu Pro Val Ala Glu
195 200 205

Ala

<210> SEQ ID NO 9
<211> LENGTH: 600
<212> TYPE: DNA
<213> ORGANISM: pestivirus type 2

<400> SEQUENCE: 9
actatagtac catattgtga tacttacact gtgacaggga tgtatgtcca tgtaaagaat 60
tgcctcccta gagggttacc taagcattca aaaataatct ccccgacaat gatatatctg 120
ggagaaggag acccggccca taatatccag cacttatttg gctcaggtat agcaaagtgg 180
gtcctagttc tactcgggat tctgggtgag tggtatggag aattggcttc cacaatatac 240
ttactactag aatacgggtc tgagtggttg gaacatgaaa gcctggtcac ggaagggttg 300
attcctggca ttaatattac aatagaactc ccagctagtc atacagtgcc tggttgggtg 360
tgggtcgcag gccagtgggt atgcgtgaag ccagactggt ggcctacaca gatttggatt 420
gaaaccgtgg tggcagagac ctggcatata ctaaaaatat tggcgtcagc cctggtgaac 480
atagttgcag cgttcgtaaa cctggaattg gtttatctgg tcataatact agtcaaaata 540
tcaaaaggga acctgatagg tgccatatta tggtgcttgt tactgtcagg cgctgaaggc 600

<210> SEQ ID NO 10
<211> LENGTH: 200
<212> TYPE: PRT
<213> ORGANISM: pestivirus type 2

<400> SEQUENCE: 10

```
Thr Ile Val Pro Tyr Cys Asp Thr Tyr Thr Val Thr Gly Met Tyr Val
1               5                   10                  15

His Val Lys Asn Cys Leu Pro Arg Gly Leu Pro Lys His Ser Lys Ile
            20                  25                  30

Ile Ser Pro Thr Met Ile Tyr Leu Gly Glu Gly Asp Pro Ala His Asn
        35                  40                  45

Ile Gln His Leu Phe Gly Ser Gly Ile Ala Lys Trp Val Leu Val Leu
    50                  55                  60

Leu Gly Ile Leu Gly Glu Trp Tyr Gly Glu Leu Ala Ser Thr Ile Tyr
65                  70                  75                  80

Leu Leu Leu Glu Tyr Gly Ser Glu Trp Leu Glu His Glu Ser Leu Val
                85                  90                  95

Thr Glu Gly Leu Ile Pro Gly Ile Asn Ile Thr Ile Glu Leu Pro Ala
            100                 105                 110

Ser His Thr Val Pro Gly Trp Val Trp Val Ala Gly Gln Trp Val Cys
        115                 120                 125

Val Lys Pro Asp Trp Trp Pro Thr Gln Ile Trp Ile Glu Thr Val Val
    130                 135                 140

Ala Glu Thr Trp His Ile Leu Lys Ile Leu Ala Ser Ala Leu Val Asn
145                 150                 155                 160

Ile Val Ala Ala Phe Val Asn Leu Glu Leu Val Tyr Leu Val Ile Ile
                165                 170                 175

Leu Val Lys Ile Ser Lys Gly Asn Leu Ile Gly Ala Ile Leu Trp Cys
            180                 185                 190

Leu Leu Leu Ser Gly Ala Glu Gly
        195                 200


<210> SEQ ID NO 11
<211> LENGTH: 1116
<212> TYPE: DNA
<213> ORGANISM: pestivirus type 2

<400> SEQUENCE: 11

tcgtgctaca aaagacaaga ctattacaac acccaactag tcgtcgaaga aaaaacaggc      60

gtagaaaaac gatctataat gggcaagtgg accgtgataa ccagggaagg tcgggagcca     120

agattaatgg agcaaataaa tatggtattg aatgatagcc tgtcagaaac ctactgctat     180

aataggctaa acaccagcac ttgggggcgg caaccggcaa gacaaagagg gtgtggtcaa     240

accgtgccct attggcctgg tgacaatgtt ctagaagaac aatactacag cacaggttac     300

tgggtgaatg taacaggcgg ttgccagctg agagaaggcg tatggctatc aagaaagggt     360

aacgtacagt gtcagcgtaa cggctcatcc ttgatgctgc aattggcgat aaaagaagag     420

aatgacacta tggaaatacc atgtgaccca gtggaaactg aaagtatggg tccagttgca     480

cagggcactt gtgtgtacag ctgggcattc gccccaagag ggtggtacta taacaggaag     540

gatggttatt ggctccagta cataaagaaa aacgactacc agtattggac aaaaatgcct     600

actgcctcgt ccgccgcaac catgtaccgc cacttgctcc ccttactggt ggcctgcctc     660

atgggcggta ggatatcggt gtggtttgtg gcaatgctcc tgtctctaca ggtggaagct     720

agtgaagtag gcactaaaca actggctgtc acgctaaccc tgtggaaaat ggactggaca     780

gaactacttt tctatattgt cttgatgcta gccgttaagg aagaacttat aaaaaaaatt     840

gtgaccgcta gccttgtggc cttaaaaaat agtccagtag ccttgagttt tcttattgta     900

ctcagacttg tgggggcag tgaagcactc ccagtaggtt tattattaga aaaaatgtgc     960
```

```
atagaccaac cggagtttgg aactcctttc ctgatctacc tatgggacaa ctggaagtgg   1020

actgtgttag tcagcttctc cgcactgaac catgaaaaaa ctataaaact ggcaagaaaa   1080

ctgttgttgg caacacatat aacagcgctc acattg                             1116


<210> SEQ ID NO 12
<211> LENGTH: 372
<212> TYPE: PRT
<213> ORGANISM: pestivirus type 2

<400> SEQUENCE: 12

Ser Cys Tyr Lys Arg Gln Asp Tyr Tyr Asn Thr Gln Leu Val Val Glu
1               5                   10                  15

Glu Lys Thr Gly Val Glu Lys Arg Ser Ile Met Gly Lys Trp Thr Val
            20                  25                  30

Ile Thr Arg Glu Gly Arg Glu Pro Arg Leu Met Glu Gln Ile Asn Met
        35                  40                  45

Val Leu Asn Asp Ser Leu Ser Glu Thr Tyr Cys Tyr Asn Arg Leu Asn
    50                  55                  60

Thr Ser Thr Trp Gly Arg Gln Pro Ala Arg Gln Arg Gly Cys Gly Gln
65                  70                  75                  80

Thr Val Pro Tyr Trp Pro Gly Asp Asn Val Leu Glu Glu Gln Tyr Tyr
                85                  90                  95

Ser Thr Gly Tyr Trp Val Asn Val Thr Gly Gly Cys Gln Leu Arg Glu
            100                 105                 110

Gly Val Trp Leu Ser Arg Lys Gly Asn Val Gln Cys Gln Arg Asn Gly
        115                 120                 125

Ser Ser Leu Met Leu Gln Leu Ala Ile Lys Glu Glu Asn Asp Thr Met
    130                 135                 140

Glu Ile Pro Cys Asp Pro Val Glu Thr Glu Ser Met Gly Pro Val Ala
145                 150                 155                 160

Gln Gly Thr Cys Val Tyr Ser Trp Ala Phe Ala Pro Arg Gly Trp Tyr
                165                 170                 175

Tyr Asn Arg Lys Asp Gly Tyr Trp Leu Gln Tyr Ile Lys Lys Asn Asp
            180                 185                 190

Tyr Gln Tyr Trp Thr Lys Met Pro Thr Ala Ser Ser Ala Ala Thr Met
        195                 200                 205

Tyr Arg His Leu Leu Pro Leu Leu Val Ala Cys Leu Met Gly Gly Arg
    210                 215                 220

Ile Ser Val Trp Phe Val Ala Met Leu Leu Ser Leu Gln Val Glu Ala
225                 230                 235                 240

Ser Glu Val Gly Thr Lys Gln Leu Ala Val Thr Leu Thr Leu Trp Lys
                245                 250                 255

Met Asp Trp Thr Glu Leu Leu Phe Tyr Ile Val Leu Met Leu Ala Val
            260                 265                 270

Lys Glu Glu Leu Ile Lys Lys Ile Val Thr Ala Ser Leu Val Ala Leu
        275                 280                 285

Lys Asn Ser Pro Val Ala Leu Ser Phe Leu Ile Val Leu Arg Leu Val
    290                 295                 300

Gly Gly Ser Glu Ala Leu Pro Val Gly Leu Leu Leu Glu Lys Met Cys
305                 310                 315                 320

Ile Asp Gln Pro Glu Phe Gly Thr Pro Phe Leu Ile Tyr Leu Trp Asp
                325                 330                 335

Asn Trp Lys Trp Thr Val Leu Val Ser Phe Ser Ala Leu Asn His Glu
```

```
            340                 345                 350

Lys Thr Ile Lys Leu Ala Arg Lys Leu Leu Leu Ala Thr His Ile Thr
        355                 360                 365

Ala Leu Thr Leu
    370


<210> SEQ ID NO 13
<211> LENGTH: 2802
<212> TYPE: DNA
<213> ORGANISM: pestivirus type 2

<400> SEQUENCE: 13

actggcttga gtgattcaat cttctatatg atgcttataa caacaaattt gttaataaag      60

acattcatat acttgctggg ggctagtatg aattgggtcg agagagaaaa aaagaaattg     120

ctagtgaaga ggagactaat atacaagaaa gccgttactt gcagtcagga tgagaatgta     180

ttggagaata aattcaacaa gataactgta aacgcggatt tcaccccatg caagcttgaa     240

cttctacaat tacttagggc ttttttagtc tctttgtgtt tttcctacta caaacctctc     300

ctgtatgcag agactacctt aactgtaata gtaattggcg tacaagagta caacgtagcc     360

atggcccgcg ggcgaagtgt ggtccacagg ctactagcca tggcctatta catatacggc     420

cgcatacagg gtgacatgtt ccagctcgcc actatccagt gcctgctgtc gagtccgagg     480

aaaattatga aacacatggt agagaatcca actctcaaga agctctggca aggcgaaaca     540

gaactcttca accagggtgt tagtcaatcc aagatagtga atccaaagaa aattgggctg     600

gaagaattac acaagggcat gtgtggcctc ccaacagtag tgcaaaattt ggtcatatat     660

gcaaagaaga atgactctct tattttagga gagctgggtt accccccctgg ggatctcacc     720

agtgatgggt gggaaatttt aggtcctggc agaatcccaa agatcactaa cgtcgagtct     780

gctaagatgg acttactctc caaacttatg acctttctgg ggattgaaag ctcgagggtc     840

cccaggaccc cagtccactc aacaaggaaa ttattgaaga tagtaagggg cttggaaaca     900

ggatgggggt acactcacgc agggggggata agtagcgcaa aacacgttac aggtgaaaag     960

aacttaatga cccacatgga gggtaggaag ggaaaatata tcctacaatc tcaagaacat    1020

ggtgctgacg aggtagagta cggagtaaaa actgatcaaa aagctcccga caatgcctta    1080

tgctactgtt ttaaccctga agctacaaac ataaaaggag agacgggagc catggtgttc    1140

atgaagaaga taggaaaaaa gtggactctc gtaacatcag acggcaataa agcctattat    1200

aatgtaaaca atttgaaagg gtggtctgga ctaccaataa tgctgcactc caccggggcc    1260

atagtgggga ggattaaatc agcgtattca gatgaaaacg acctggtgga ggaacttatt    1320

gactctagaa ctattagtaa gagcaatgag acaaacctgg accaccttat caaggaattg    1380

gcagacatgc ggaggggggga gttccgctca attacccttg gaacgggagc cgggaaaacc    1440

acagaactgc ctaggcaata cctcacaaca gtaggtgccc ataaatccgt gctggtctta    1500

gtccccttaa aagcacctgc tgaaagtgtt tgccgcttta tgaggtctaa ataccctacc    1560

atcaactttt ccttaagagt gggggaacgg aaagagggag atgtgagcag cggcatcacc    1620

tacgctactt acggattttg ctgccagcta aacctagtcc aacttaaaga atggatatcc    1680

aggtactcaa tggttttttt tgatgaatat cacacagcaa ctccagaaca aatagccata    1740

ataagcaaga ttcatgcact gaaagttaag accaggatag tggctatgtc agcaaccccc    1800

ccgggtaccg tgacgactga aggcaggaag tttgacattg aagaggtagg ggttgctacc    1860

atagagaaag gagaggaacc aaaaaggggg cgcatagcgg tcgctggtat gcaggtccca    1920
```

```
ttagaagact taacaggaaa gaactgcctg gtgttcgtgg caaccaaaga agccgcggag   1980

acggaggcta aagaactgcg caccagagga attaacgcca cctactacta ttcaggtata   2040

gaccctaaga ctctggaaca tgggatgacc aatcagccat actgtattgt agctaccaat   2100

gccattgaat caggtataac ctgtcctgac ttggatgtgg tcatagacac catgcagaag   2160

tacgaaaaag tagtgaattt ctcggcaaag atgcccttga ttgtcacttc attagtaaag   2220

aaaaaaatca ccagggaaga acagggccag aggaaaggtc gagtgggcag gcaaaagaaa   2280

ggaaaatact actacccctc gggggtggta ccgaatgggt caaaagacct aagctattta   2340

atcctacagg cccaagaata tggtgtcttg gaacaagtca atataacaga gtacttcatc   2400

ataatgaatg aggactgggg tctctatgac gtagatgaag tagaagtgag aatacttgag   2460

agaatgaaca aggaaatctt gctaccacta ggtattgtgg agaagcaaat cttggaaaga   2520

agtactcacc cggaaaaagt ggcactgttg tataacaaat tagtgcagaa aaatcctata   2580

gtatacccta gagtacagga aggtgaggtc agcaaggaat acaataccta taatctggcc   2640

gtatatgaca agctaaaaga tgtcaaccca caagccattt atgttctagc agaagaggag   2700

agagccacag aaatgatggg tctcgagttt gaacaagacc catctgactt acaggattcg   2760

gtagttcagc tttgtgaaga tatcaagagg tatacaaaac tc                      2802
```

<210> SEQ ID NO 14
<211> LENGTH: 934
<212> TYPE: PRT
<213> ORGANISM: pestivirus type 2

<400> SEQUENCE: 14

```
Thr Gly Leu Ser Asp Ser Ile Phe Tyr Met Met Leu Ile Thr Thr Asn
1               5                   10                  15

Leu Leu Ile Lys Thr Phe Ile Tyr Leu Leu Gly Ala Ser Met Asn Trp
            20                  25                  30

Val Glu Arg Glu Lys Lys Lys Leu Leu Val Lys Arg Arg Leu Ile Tyr
        35                  40                  45

Lys Lys Ala Val Thr Cys Ser Gln Asp Glu Asn Val Leu Glu Asn Lys
    50                  55                  60

Phe Asn Lys Ile Thr Val Asn Ala Asp Phe Thr Pro Cys Lys Leu Glu
65                  70                  75                  80

Leu Leu Gln Leu Leu Arg Ala Phe Leu Val Ser Leu Cys Phe Ser Tyr
                85                  90                  95

Tyr Lys Pro Leu Leu Tyr Ala Glu Thr Thr Leu Thr Val Ile Val Ile
            100                 105                 110

Gly Val Gln Glu Tyr Asn Val Ala Met Ala Arg Gly Arg Ser Val Val
        115                 120                 125

His Arg Leu Leu Ala Met Ala Tyr Tyr Ile Tyr Gly Arg Ile Gln Gly
    130                 135                 140

Asp Met Phe Gln Leu Ala Thr Ile Gln Cys Leu Leu Ser Ser Pro Arg
145                 150                 155                 160

Lys Ile Met Lys His Met Val Glu Asn Pro Thr Leu Lys Lys Leu Trp
                165                 170                 175

Gln Gly Glu Thr Glu Leu Phe Asn Gln Gly Val Ser Gln Ser Lys Ile
            180                 185                 190

Val Asn Pro Lys Lys Ile Gly Leu Glu Glu Leu His Lys Gly Met Cys
        195                 200                 205

Gly Leu Pro Thr Val Val Gln Asn Leu Val Ile Tyr Ala Lys Lys Asn
```

```
    210                 215                 220

Asp Ser Leu Ile Leu Gly Glu Leu Gly Tyr Pro Pro Gly Asp Leu Thr
225                 230                 235                 240

Ser Asp Gly Trp Glu Ile Leu Gly Pro Gly Arg Ile Pro Lys Ile Thr
                245                 250                 255

Asn Val Glu Ser Ala Lys Met Asp Leu Leu Ser Lys Leu Met Thr Phe
            260                 265                 270

Leu Gly Ile Glu Ser Ser Arg Val Pro Arg Thr Pro Val His Ser Thr
        275                 280                 285

Arg Lys Leu Leu Lys Ile Val Arg Gly Leu Glu Thr Gly Trp Gly Tyr
    290                 295                 300

Thr His Ala Gly Gly Ile Ser Ser Ala Lys His Val Thr Gly Glu Lys
305                 310                 315                 320

Asn Leu Met Thr His Met Glu Gly Arg Lys Gly Lys Tyr Ile Leu Gln
                325                 330                 335

Ser Gln Glu His Gly Ala Asp Glu Val Glu Tyr Gly Val Lys Thr Asp
            340                 345                 350

Gln Lys Ala Pro Asp Asn Ala Leu Cys Tyr Cys Phe Asn Pro Glu Ala
        355                 360                 365

Thr Asn Ile Lys Gly Glu Thr Gly Ala Met Val Phe Met Lys Lys Ile
    370                 375                 380

Gly Lys Lys Trp Thr Leu Val Thr Ser Asp Gly Asn Lys Ala Tyr Tyr
385                 390                 395                 400

Asn Val Asn Asn Leu Lys Gly Trp Ser Gly Leu Pro Ile Met Leu His
                405                 410                 415

Ser Thr Gly Ala Ile Val Gly Arg Ile Lys Ser Ala Tyr Ser Asp Glu
            420                 425                 430

Asn Asp Leu Val Glu Glu Leu Ile Asp Ser Arg Thr Ile Ser Lys Ser
        435                 440                 445

Asn Glu Thr Asn Leu Asp His Leu Ile Lys Glu Leu Ala Asp Met Arg
    450                 455                 460

Arg Gly Glu Phe Arg Ser Ile Thr Leu Gly Thr Gly Ala Gly Lys Thr
465                 470                 475                 480

Thr Glu Leu Pro Arg Gln Tyr Leu Thr Thr Val Gly Ala His Lys Ser
                485                 490                 495

Val Leu Val Leu Val Pro Leu Lys Ala Pro Ala Glu Ser Val Cys Arg
            500                 505                 510

Phe Met Arg Ser Lys Tyr Pro Thr Ile Asn Phe Ser Leu Arg Val Gly
        515                 520                 525

Glu Arg Lys Glu Gly Asp Val Ser Ser Gly Ile Thr Tyr Ala Thr Tyr
    530                 535                 540

Gly Phe Cys Cys Gln Leu Asn Leu Val Gln Leu Lys Glu Trp Ile Ser
545                 550                 555                 560

Arg Tyr Ser Met Val Phe Phe Asp Glu Tyr His Thr Ala Thr Pro Glu
                565                 570                 575

Gln Ile Ala Ile Ile Ser Lys Ile His Ala Leu Lys Val Lys Thr Arg
            580                 585                 590

Ile Val Ala Met Ser Ala Thr Pro Pro Gly Thr Val Thr Thr Glu Gly
        595                 600                 605

Arg Lys Phe Asp Ile Glu Glu Val Gly Val Ala Thr Ile Glu Lys Gly
    610                 615                 620

Glu Glu Pro Lys Arg Gly Arg Ile Ala Val Ala Gly Met Gln Val Pro
625                 630                 635                 640
```

```
Leu Glu Asp Leu Thr Gly Lys Asn Cys Leu Val Phe Val Ala Thr Lys
                645                 650                 655

Glu Ala Ala Glu Thr Glu Ala Lys Glu Leu Arg Thr Arg Gly Ile Asn
            660                 665                 670

Ala Thr Tyr Tyr Tyr Ser Gly Ile Asp Pro Lys Thr Leu Glu His Gly
        675                 680                 685

Met Thr Asn Gln Pro Tyr Cys Ile Val Ala Thr Asn Ala Ile Glu Ser
    690                 695                 700

Gly Ile Thr Cys Pro Asp Leu Asp Val Val Ile Asp Thr Met Gln Lys
705                 710                 715                 720

Tyr Glu Lys Val Val Asn Phe Ser Ala Lys Met Pro Leu Ile Val Thr
                725                 730                 735

Ser Leu Val Lys Lys Lys Ile Thr Arg Glu Glu Gln Gly Gln Arg Lys
            740                 745                 750

Gly Arg Val Gly Arg Gln Lys Lys Gly Lys Tyr Tyr Tyr Pro Ser Gly
        755                 760                 765

Val Val Pro Asn Gly Ser Lys Asp Leu Ser Tyr Leu Ile Leu Gln Ala
    770                 775                 780

Gln Glu Tyr Gly Val Leu Glu Gln Val Asn Ile Thr Glu Tyr Phe Ile
785                 790                 795                 800

Ile Met Asn Glu Asp Trp Gly Leu Tyr Asp Val Asp Glu Val Glu Val
                805                 810                 815

Arg Ile Leu Glu Arg Met Asn Lys Glu Ile Leu Leu Pro Leu Gly Ile
            820                 825                 830

Val Glu Lys Gln Ile Leu Glu Arg Ser Thr His Pro Glu Lys Val Ala
        835                 840                 845

Leu Leu Tyr Asn Lys Leu Val Gln Lys Asn Pro Ile Val Tyr Pro Arg
    850                 855                 860

Val Gln Glu Gly Glu Val Ser Lys Glu Tyr Asn Thr Tyr Asn Leu Ala
865                 870                 875                 880

Val Tyr Asp Lys Leu Lys Asp Val Asn Pro Gln Ala Ile Tyr Val Leu
                885                 890                 895

Ala Glu Glu Glu Arg Ala Thr Glu Met Met Gly Leu Glu Phe Glu Gln
            900                 905                 910

Asp Pro Ser Asp Leu Gln Asp Ser Val Val Gln Leu Cys Glu Asp Ile
        915                 920                 925

Lys Arg Tyr Thr Lys Leu
    930
```

<210> SEQ ID NO 15
<211> LENGTH: 2061
<212> TYPE: DNA
<213> ORGANISM: pestivirus type 2

<400> SEQUENCE: 15

```
ggtcctggca gaatcccaaa gatcactaac gtcgagtctg ctaagatgga cttactctcc      60

aaacttatga cctttctggg gattgaaagc tcgagggtcc ccaggacccc agtccactca     120

acaaggaaat tattgaagat agtaaggggc ttggaaacag gatgggggta cactcacgca     180

ggggggataa gtagcgcaaa acacgttaca ggtgaaaaga acttaatgac ccacatggag     240

ggtaggaagg gaaaatatat cctacaatct caagaacatg gtgctgacga ggtagagtac     300

ggagtaaaaa ctgatcaaaa agctcccgac aatgccttat gctactgttt taaccctgaa     360

gctacaaaca taaaaggaga gacgggagcc atggtgttca tgaagaagat aggaaaaaag     420
```

```
tggactctcg taacatcaga cggcaataaa gcctattata atgtaaacaa tttgaaaggg    480
tggtctggac taccaataat gctgcactcc accggggcca tagtggggag gattaaatca    540
gcgtattcag atgaaaacga cctggtggag gaacttattg actctagaac tattagtaag    600
agcaatgaga caaacctgga ccaccttatc aaggaattgg cagacatgcg gagggggag     660
ttccgctcaa ttacccttgg aacgggagcc gggaaaacca cagaactgcc taggcaatac    720
ctcacaacag taggtgccca taaatccgtg ctggtcttag tccccttaaa agcacctgct    780
gaaagtgttt gccgctttat gaggtctaaa taccctacca tcaacttttc cttaagagtg    840
ggggaacgga aagagggaga tgtgagcagc ggcatcacct acgctactta cggattttgc    900
tgccagctaa acctagtcca acttaaagaa tggatatcca ggtactcaat ggtttttttt    960
gatgaatatc acacagcaac tccagaacaa atagccataa taagcaagat tcatgcactg   1020
aaagttaaga ccaggatagt ggctatgtca gcaacccccc cgggtaccgt gacgactgaa   1080
ggcaggaagt ttgacattga agaggtaggg gttgctacca tagagaaagg agaggaacca   1140
aaaagggggc gcatagcggt cgctggtatg caggtcccat tagaagactt aacaggaaag   1200
aactgcctgg tgttcgtggc aaccaaagaa gccgcggaga cggaggctaa agaactgcgc   1260
accagaggaa ttaacgccac ctactactat tcaggtatag accctaagac tctggaacat   1320
gggatgacca atcagccata ctgtattgta gctaccaatg ccattgaatc aggtataacc   1380
tgtcctgact tggatgtggt catagacacc atgcagaagt acgaaaaagt agtgaatttc   1440
tcggcaaaga tgcccttgat tgtcacttca ttagtaaaga aaaaaatcac cagggaagaa   1500
cagggccaga ggaaaggtcg agtgggcagg caaaagaaag gaaaatacta ctacccctcg   1560
ggggtggtac cgaatgggtc aaaagaccta agctatttaa tcctacaggc ccaagaatat   1620
ggtgtcttgg aacaagtcaa tataacagag tacttcatca taatgaatga ggactggggt   1680
ctctatgacg tagatgaagt agaagtgaga atacttgaga gaatgaacaa ggaaatcttg   1740
ctaccactag gtattgtgga gaagcaaatc ttggaaagaa gtactcaccc ggaaaaagtg   1800
gcactgttgt ataacaaatt agtgcagaaa aatcctatag tataccctag agtacaggaa   1860
ggtgaggtca gcaaggaata caatacctat aatctggccg tatatgacaa gctaaaagat   1920
gtcaacccac aagccattta tgttctagca gaagaggaga gagccacaga aatgatgggt   1980
ctcgagtttg aacaagaccc atctgactta caggattcgg tagttcagct ttgtgaagat   2040
atcaagaggt atacaaaact c                                             2061
```

<210> SEQ ID NO 16
<211> LENGTH: 687
<212> TYPE: PRT
<213> ORGANISM: pestivirus type 2

<400> SEQUENCE: 16

```
Gly Pro Gly Arg Ile Pro Lys Ile Thr Asn Val Glu Ser Ala Lys Met
1               5                   10                  15

Asp Leu Leu Ser Lys Leu Met Thr Phe Leu Gly Ile Glu Ser Ser Arg
            20                  25                  30

Val Pro Arg Thr Pro Val His Ser Thr Arg Lys Leu Leu Lys Ile Val
        35                  40                  45

Arg Gly Leu Glu Thr Gly Trp Gly Tyr Thr His Ala Gly Gly Ile Ser
    50                  55                  60

Ser Ala Lys His Val Thr Gly Glu Lys Asn Leu Met Thr His Met Glu
65                  70                  75                  80
```

-continued

```
Gly Arg Lys Gly Lys Tyr Ile Leu Gln Ser Gln Glu His Gly Ala Asp
                85                  90                  95

Glu Val Glu Tyr Gly Val Lys Thr Asp Gln Lys Ala Pro Asp Asn Ala
            100                 105                 110

Leu Cys Tyr Cys Phe Asn Pro Glu Ala Thr Asn Ile Lys Gly Glu Thr
        115                 120                 125

Gly Ala Met Val Phe Met Lys Lys Ile Gly Lys Lys Trp Thr Leu Val
    130                 135                 140

Thr Ser Asp Gly Asn Lys Ala Tyr Tyr Asn Val Asn Asn Leu Lys Gly
145                 150                 155                 160

Trp Ser Gly Leu Pro Ile Met Leu His Ser Thr Gly Ala Ile Val Gly
                165                 170                 175

Arg Ile Lys Ser Ala Tyr Ser Asp Glu Asn Asp Leu Val Glu Glu Leu
            180                 185                 190

Ile Asp Ser Arg Thr Ile Ser Lys Ser Asn Glu Thr Asn Leu Asp His
        195                 200                 205

Leu Ile Lys Glu Leu Ala Asp Met Arg Arg Gly Glu Phe Arg Ser Ile
    210                 215                 220

Thr Leu Gly Thr Gly Ala Gly Lys Thr Thr Glu Leu Pro Arg Gln Tyr
225                 230                 235                 240

Leu Thr Thr Val Gly Ala His Lys Ser Val Leu Val Leu Val Pro Leu
                245                 250                 255

Lys Ala Pro Ala Glu Ser Val Cys Arg Phe Met Arg Ser Lys Tyr Pro
            260                 265                 270

Thr Ile Asn Phe Ser Leu Arg Val Gly Glu Arg Lys Glu Gly Asp Val
        275                 280                 285

Ser Ser Gly Ile Thr Tyr Ala Thr Tyr Gly Phe Cys Cys Gln Leu Asn
    290                 295                 300

Leu Val Gln Leu Lys Glu Trp Ile Ser Arg Tyr Ser Met Val Phe Phe
305                 310                 315                 320

Asp Glu Tyr His Thr Ala Thr Pro Glu Gln Ile Ala Ile Ile Ser Lys
                325                 330                 335

Ile His Ala Leu Lys Val Lys Thr Arg Ile Val Ala Met Ser Ala Thr
            340                 345                 350

Pro Pro Gly Thr Val Thr Thr Glu Gly Arg Lys Phe Asp Ile Glu Glu
        355                 360                 365

Val Gly Val Ala Thr Ile Glu Lys Gly Glu Glu Pro Lys Arg Gly Arg
    370                 375                 380

Ile Ala Val Ala Gly Met Gln Val Pro Leu Glu Asp Leu Thr Gly Lys
385                 390                 395                 400

Asn Cys Leu Val Phe Val Ala Thr Lys Glu Ala Ala Glu Thr Glu Ala
                405                 410                 415

Lys Glu Leu Arg Thr Arg Gly Ile Asn Ala Thr Tyr Tyr Tyr Ser Gly
            420                 425                 430

Ile Asp Pro Lys Thr Leu Glu His Gly Met Thr Asn Gln Pro Tyr Cys
        435                 440                 445

Ile Val Ala Thr Asn Ala Ile Glu Ser Gly Ile Thr Cys Pro Asp Leu
    450                 455                 460

Asp Val Val Ile Asp Thr Met Gln Lys Tyr Glu Lys Val Val Asn Phe
465                 470                 475                 480

Ser Ala Lys Met Pro Leu Ile Val Thr Ser Leu Val Lys Lys Lys Ile
                485                 490                 495
```

-continued

```
Thr Arg Glu Glu Gln Gly Gln Arg Lys Gly Arg Val Gly Arg Gln Lys
            500                 505                 510

Lys Gly Lys Tyr Tyr Tyr Pro Ser Gly Val Val Pro Asn Gly Ser Lys
        515                 520                 525

Asp Leu Ser Tyr Leu Ile Leu Gln Ala Gln Glu Tyr Gly Val Leu Glu
    530                 535                 540

Gln Val Asn Ile Thr Glu Tyr Phe Ile Ile Met Asn Glu Asp Trp Gly
545                 550                 555                 560

Leu Tyr Asp Val Asp Glu Val Glu Val Arg Ile Leu Glu Arg Met Asn
                565                 570                 575

Lys Glu Ile Leu Leu Pro Leu Gly Ile Val Glu Lys Gln Ile Leu Glu
            580                 585                 590

Arg Ser Thr His Pro Glu Lys Val Ala Leu Leu Tyr Asn Lys Leu Val
        595                 600                 605

Gln Lys Asn Pro Ile Val Tyr Pro Arg Val Gln Glu Gly Glu Val Ser
    610                 615                 620

Lys Glu Tyr Asn Thr Tyr Asn Leu Ala Val Tyr Asp Lys Leu Lys Asp
625                 630                 635                 640

Val Asn Pro Gln Ala Ile Tyr Val Leu Ala Glu Glu Glu Arg Ala Thr
                645                 650                 655

Glu Met Met Gly Leu Glu Phe Glu Gln Asp Pro Ser Asp Leu Gln Asp
            660                 665                 670

Ser Val Val Gln Leu Cys Glu Asp Ile Lys Arg Tyr Thr Lys Leu
        675                 680                 685


<210> SEQ ID NO 17
<211> LENGTH: 201
<212> TYPE: DNA
<213> ORGANISM: pestivirus type 2

<400> SEQUENCE: 17

tctgggatca ctgagaaact gctagtaggt acgatggtgg ggtatattgg atacaaagcc      60

ttaaccagaa accacgtgcc ctgggtcagc aaagagtatt gttatgagct gaccgattca     120

ccggatactt acgaaaactc attcgcacct ttggacgtcg acgtccaaaa ctccggtgaa     180

ggaaaacacc cagagcaact g                                               201


<210> SEQ ID NO 18
<211> LENGTH: 67
<212> TYPE: PRT
<213> ORGANISM: pestivirus type 2

<400> SEQUENCE: 18

Ser Gly Ile Thr Glu Lys Leu Leu Val Gly Thr Met Val Gly Tyr Ile
1               5                   10                  15

Gly Tyr Lys Ala Leu Thr Arg Asn His Val Pro Trp Val Ser Lys Glu
            20                  25                  30

Tyr Cys Tyr Glu Leu Thr Asp Ser Pro Asp Thr Tyr Glu Asn Ser Phe
        35                  40                  45

Ala Pro Leu Asp Val Asp Val Gln Asn Ser Gly Glu Gly Lys His Pro
    50                  55                  60

Glu Gln Leu
65


<210> SEQ ID NO 19
<211> LENGTH: 2433
<212> TYPE: DNA
```

<213> ORGANISM: pestivirus type 2

<400> SEQUENCE: 19
gcagaccatc aattgaggca actactggag actgggagag acaaggcaat tgatttccta 60
aaaggaatcc gcgagttcac tagtggggcc ataaacagtc caaaggcact aagtatatgg 120
gagaaaatat atcagtattt gaagaagcat cagggcgaga tcatctcatc agcagcgtgg 180
ggcagtgcga cggcccttca cgacagtatt aaatctagac taggagatga ggtcgctact 240
gcagtaataa tcctcaagta tttagcattt ggtgaaagag aactgtctgg gctaactagg 300
caagttctaa ttgacatcat agtatattat atagttaaca agccccggtt cgaaggagac 360
gactacgcaa agagaaaagg aagaaggcta gtcatcgaag tcctgatggg ggcactggcg 420
acttatgcgg tgtccaattt ttggggtgtg tccattaata agatactgca accaatttct 480
gattatctac cctatgccac cgccactttg gcttttcttc gcccaacctt catggaatca 540
gcagtggtgg tcgcttcctc tatctataga gcttttctct ccattaagca tgcggaaaac 600
aggagtcttg tcacgcaggt cgcttctgcc gccctcgaag tcatgggcct gaccccagta 660
tcggctggcc taggcgtctt gctggggctt gggttgtgtg tgctccatat gaacattgac 720
aagaatgagg agaaaaggac acttatactg aaaatgtttg tcaaaaactt tatagaccag 780
gcggcactag acgagttgga taaactggag ccagaaaaaa taatcctctc attgttggag 840
ggtatccaaa cctgcacaaa cccgattaga gcaatcatga ttttgtacag ggtgtactac 900
aagggagaaa ctttcacaga agctttgtct aagatggccg gcaagtctct cattgtgatg 960
gtcatagtcg agttcctgga attgacaggc caaacccaag gagggtatat agatcttagt 1020
gctaatttgc tgacctttct cctcgagaaa ctaaaaaaaa tgactaacct cgccatcggg 1080
gaagctagaa aggtcttgct ccccatccca tacttgtact gtgaaacctg gcagtctgac 1140
gccagaatca aggcccctga atcctacgac caagtggtag tggaatgcaa atgtggcgct 1200
tcagcgaggt attccttccg cgatggagtt catgagatat tggaagaaaa aaggactaat 1260
tggtgcaaga acttcttctt atggggaccc aacttccaca atccggatcc aaaaaggatg 1320
acattctatg aatacggcca agcaaaaaag tgtcctgtta tcataattgg tgaagacata 1380
accttcggca aatatggcat atatatcaaa tttggccata ggcctgatgg agggaggtta 1440
ataaggggta ccacccacgc tactatcagt agggaggaat tgctggaaat cctaacagcc 1500
ccaagccaag tggccatagg caaggtcaag ctaaccgatt actgtaatca aaaaggaata 1560
atagacagga aattggccgt acttgaaggt gacaaaatac atttttggaa agcacaccgt 1620
ggatccaaaa tcacagacca actcactatt gagaatctga cagatgattt ggggtcagaa 1680
atcagggaca tcacatggga gctgtacaca ggtggaacgt gcaccgtaaa aggggtgtcc 1740
cttagatcat gcgcaccagg tcatagaact aaggctatgg tcttgtgtga ttgcactgat 1800
gtgcttagcc cctgttacct aataaacggc aggagaccat ccccatttga cgtcgcggaa 1860
ggttatgaat gtcaccaccg gaagccccga gcgacgtatg aagacctaga aatggaggaa 1920
atactaaaga gacgagtccc tgtctacgat cctctgtgtt tgtttgacac tgatagtaaa 1980
ctgctacctc ccgacaccta ctacttggaa gaagatcaag aggactttga gtacgcattg 2040
agatgctggg gcctcggggt ttatgtagca gacgggcctg tcacttcccc cccggacata 2100
agaatacacc atagttcggt attactactg ctgacacctg gagtaaactc agagttgccc 2160
ttacagtaca tacgttgtta ccctcatcag gcagaggtgg acatctacat taggagtcag 2220
cttttggagg aggaagacac tgctacggag gtggaaggct cccaggaaga tggtgatgaa 2280

```
gggatgggcg atgcggtaat agaggatgag gatacatcgt ccacaacaga atcaataccc   2340

ccactagaag aggaggaagg gggcgaagag ccaatcacct atgtggtcat aaggggatta   2400

caagaagaaa gatacgccag ccatcttaaa cta                                2433


<210> SEQ ID NO 20
<211> LENGTH: 811
<212> TYPE: PRT
<213> ORGANISM: pestivirus type 2

<400> SEQUENCE: 20

Ala Asp His Gln Leu Arg Gln Leu Leu Glu Thr Gly Arg Asp Lys Ala
1               5                   10                  15

Ile Asp Phe Leu Lys Gly Ile Arg Glu Phe Thr Ser Gly Ala Ile Asn
            20                  25                  30

Ser Pro Lys Ala Leu Ser Ile Trp Glu Lys Ile Tyr Gln Tyr Leu Lys
        35                  40                  45

Lys His Gln Gly Glu Ile Ile Ser Ser Ala Ala Trp Gly Ser Ala Thr
    50                  55                  60

Ala Leu His Asp Ser Ile Lys Ser Arg Leu Gly Asp Glu Val Ala Thr
65                  70                  75                  80

Ala Val Ile Ile Leu Lys Tyr Leu Ala Phe Gly Glu Arg Glu Leu Ser
                85                  90                  95

Gly Leu Thr Arg Gln Val Leu Ile Asp Ile Ile Val Tyr Tyr Ile Val
            100                 105                 110

Asn Lys Pro Arg Phe Glu Gly Asp Asp Tyr Ala Lys Arg Lys Gly Arg
        115                 120                 125

Arg Leu Val Ile Glu Val Leu Met Gly Ala Leu Ala Thr Tyr Ala Val
    130                 135                 140

Ser Asn Phe Trp Gly Val Ser Ile Asn Lys Ile Leu Gln Pro Ile Ser
145                 150                 155                 160

Asp Tyr Leu Pro Tyr Ala Thr Ala Thr Leu Ala Phe Leu Arg Pro Thr
                165                 170                 175

Phe Met Glu Ser Ala Val Val Val Ala Ser Ser Ile Tyr Arg Ala Phe
            180                 185                 190

Leu Ser Ile Lys His Ala Glu Asn Arg Ser Leu Val Thr Gln Val Ala
        195                 200                 205

Ser Ala Ala Leu Glu Val Met Gly Leu Thr Pro Val Ser Ala Gly Leu
    210                 215                 220

Gly Val Leu Leu Gly Leu Gly Leu Cys Val Leu His Met Asn Ile Asp
225                 230                 235                 240

Lys Asn Glu Glu Lys Arg Thr Leu Ile Leu Lys Met Phe Val Lys Asn
                245                 250                 255

Phe Ile Asp Gln Ala Ala Leu Asp Glu Leu Asp Lys Leu Glu Pro Glu
            260                 265                 270

Lys Ile Ile Leu Ser Leu Leu Glu Gly Ile Gln Thr Cys Thr Asn Pro
        275                 280                 285

Ile Arg Ala Ile Met Ile Leu Tyr Arg Val Tyr Tyr Lys Gly Glu Thr
    290                 295                 300

Phe Thr Glu Ala Leu Ser Lys Met Ala Gly Lys Ser Leu Ile Val Met
305                 310                 315                 320

Val Ile Val Glu Phe Leu Glu Leu Thr Gly Gln Thr Gln Gly Gly Tyr
                325                 330                 335

Ile Asp Leu Ser Ala Asn Leu Leu Thr Phe Leu Leu Glu Lys Leu Lys
```

-continued

```
            340                 345                 350

Lys Met Thr Asn Leu Ala Ile Gly Glu Ala Arg Lys Val Leu Leu Pro
        355                 360                 365

Ile Pro Tyr Leu Tyr Cys Glu Thr Trp Gln Ser Asp Ala Arg Ile Lys
    370                 375                 380

Ala Pro Glu Ser Tyr Asp Gln Val Val Val Glu Cys Lys Cys Gly Ala
385                 390                 395                 400

Ser Ala Arg Tyr Ser Phe Arg Asp Gly Val His Glu Ile Leu Glu Glu
                405                 410                 415

Lys Arg Thr Asn Trp Cys Lys Asn Phe Phe Leu Trp Gly Pro Asn Phe
            420                 425                 430

His Asn Pro Asp Pro Lys Arg Met Thr Phe Tyr Glu Tyr Gly Gln Ala
        435                 440                 445

Lys Lys Cys Pro Val Ile Ile Ile Gly Glu Asp Ile Thr Phe Gly Lys
    450                 455                 460

Tyr Gly Ile Tyr Ile Lys Phe Gly His Arg Pro Asp Gly Gly Arg Leu
465                 470                 475                 480

Ile Arg Gly Thr Thr His Ala Thr Ile Ser Arg Glu Glu Leu Leu Glu
                485                 490                 495

Ile Leu Thr Ala Pro Ser Gln Val Ala Ile Gly Lys Val Lys Leu Thr
            500                 505                 510

Asp Tyr Cys Asn Gln Lys Gly Ile Ile Asp Arg Lys Leu Ala Val Leu
        515                 520                 525

Glu Gly Asp Lys Ile His Phe Trp Lys Ala His Arg Gly Ser Lys Ile
    530                 535                 540

Thr Asp Gln Leu Thr Ile Glu Asn Leu Thr Asp Asp Leu Gly Ser Glu
545                 550                 555                 560

Ile Arg Asp Ile Thr Trp Glu Leu Tyr Thr Gly Gly Thr Cys Thr Val
                565                 570                 575

Lys Gly Val Ser Leu Arg Ser Cys Ala Pro Gly His Arg Thr Lys Ala
            580                 585                 590

Met Val Leu Cys Asp Cys Thr Asp Val Leu Ser Pro Cys Tyr Leu Ile
        595                 600                 605

Asn Gly Arg Arg Pro Ser Pro Phe Asp Val Ala Glu Gly Tyr Glu Cys
    610                 615                 620

His His Arg Lys Pro Arg Ala Thr Tyr Glu Asp Leu Glu Met Glu Glu
625                 630                 635                 640

Ile Leu Lys Arg Arg Val Pro Val Tyr Asp Pro Leu Cys Leu Phe Asp
                645                 650                 655

Thr Asp Ser Lys Leu Leu Pro Pro Asp Thr Tyr Tyr Leu Glu Glu Asp
            660                 665                 670

Gln Glu Asp Phe Glu Tyr Ala Leu Arg Cys Trp Gly Leu Gly Val Tyr
        675                 680                 685

Val Ala Asp Gly Pro Val Thr Ser Pro Pro Asp Ile Arg Ile His His
    690                 695                 700

Ser Ser Val Leu Leu Leu Leu Thr Pro Gly Val Asn Ser Glu Leu Pro
705                 710                 715                 720

Leu Gln Tyr Ile Arg Cys Tyr Pro His Gln Ala Glu Val Asp Ile Tyr
                725                 730                 735

Ile Arg Ser Gln Leu Leu Glu Glu Glu Asp Thr Ala Thr Glu Val Glu
            740                 745                 750

Gly Ser Gln Glu Asp Gly Asp Glu Gly Met Gly Asp Ala Val Ile Glu
        755                 760                 765
```

Asp Glu Asp Thr Ser Ser Thr Thr Glu Ser Ile Pro Pro Leu Glu Glu
    770                 775                 780

Glu Glu Gly Gly Glu Glu Pro Ile Thr Tyr Val Val Ile Arg Gly Leu
785                 790                 795                 800

Gln Glu Glu Arg Tyr Ala Ser His Leu Lys Leu
                805                 810

<210> SEQ ID NO 21
<211> LENGTH: 2256
<212> TYPE: DNA
<213> ORGANISM: pestivirus type 2

<400> SEQUENCE: 21
aatgactgga tcagtgaaaa catttcagag ccacacagag tccaaattat gctagatggg 60
acagtgagag tcacaataaa agagggcaaa gtgaaacatt tgtttggggt ctatagaata 120
gaaaactccc tggaagcaat gtttaaagag accatagctg acctccccgt agctacccaa 180
ccgccccagg ggccagtcta tacggctaaa gagctggccc aagggaacat cgccccggtc 240
caacctgcag cgaattatta cggaatgata gaggggagag gcgacccaat gacggcattc 300
gaagccttat cagtcttgcg gtcacaaaaa gtcttagcca aggacgtgaa ggtgaacacc 360
cgcagggcgc aggttttttt aaataaagtc aggagaattg ctgaggtcag agcgtcggaa 420
ctgacattaa aatgcttacc gatacttggc aaagtaaatg ggaggaaatt gattagagag 480
gaaaccaaca tccccaacca aaggttggca tcaataatga cctcaatagg aattagacta 540
gaaaaactgc cagtggttag agcaaacact tccggctcta agttcagaca gtcaatctta 600
gaaaaaatgg ataagtatga aaatgaacaa gtcccagggt tacatgaaaa gatgtgggca 660
gcgttcctgg caactgccag gcaagattta agaaatacct atgaggaagt aacttatctt 720
gaattagagg ccggaatcaa tcggaaagga gccccaggtt tctttgaaaa agaaagctca 780
ataggagaag tgctggaaaa aaaagaaaaa attgacgtca caatccaaga gattgaaaaa 840
ggcaaccact tatactatga aacagccatg ccaaaaaatg agaaaagaga tgtgcttgat 900
gattggttgt cagaggattt cgtcacttat aagaaaccac gtgtgataca gtaccctgag 960
gcagtcaccc ggttggccat caccaaaata atgtataagt gggtgaagca aaagcctata 1020
gtgattcccg gttatgaggg aaaaaccccg atctttgaaa tatttgaaaa agtcagtgca 1080
gattgggctc agttcaaaaa tccggtagcc gtcagcttcg acaccagagc ctgggacact 1140
caagtaacaa gagaagacct caggctggta gggcggatac agaaatacta ttacaaaaaa 1200
aaatattgga agttcattga caatttgaca gccatgatgg aggaagtgcc tgtaatcact 1260
gtagaaggag atatgttcct cagagttgga cagcgcggat ccggacagcc tgatacctca 1320
gcaggcaatt ccatgctaaa tgtgctgact atgttggtag ctttctctga atccacaaat 1380
ctgcccatag cggctgcctg gaaggcctgt cggatccacg tctgtggtga cgacggtttc 1440
ttaatcacag aatcggaatt agggaggaag tttgctgaaa aaggtgttcc tctgttagct 1500
gcatttggca aaccccaaaa aattacagag ggagcgagcc taaaggtaac cagcaacttt 1560
gacggaatag agttttgtag tcatacccct atcagagtcc aaacaccaaa catcaggtgg 1620
atgccagcga gaccaacagc aacaatccta ggcaaaatga gtaccaggct gggtgagggt 1680
gccaccaggt cgggagaaga atacgaaaaa caggtggcat tcgcatatct actgatgtac 1740
ccctggaacc cgctggtcag gagaatcagc ctcctattgt tatcgactac tgacccaatg 1800
gggaaagagg aaaccccatg ctccgatgag gggtgaagt atgttgggga ccctatcgct 1860

```
gcatacaggg atgtatgggg gcacaaatta gaggatgtag gccatgttga tcaaccgcag   1920

ttatcccgga tgaactatag catgacttac ttagggattt ggaaaccaaa gacaagtcag   1980

cggctagtcg aacagtgttg tcgtctggcc gagaaaagca attgtgtggt acgtgctgac   2040

tccctgataa agaaaaaggt caagatcact tatgacccgg ggataggagt ggctcaggtc   2100

attcgtaggt gggaagagct tgagtggacc agaaggaaac ctgaactcac caatgtaatt   2160

gtagaagatg atatcttcct agtcctgtgg aagagatttt caaagtacat ttttcagaaa   2220

atgaagttca tgcagagaat gttcgcccct tattaa                             2256


<210> SEQ ID NO 22
<211> LENGTH: 751
<212> TYPE: PRT
<213> ORGANISM: pestivirus type 2

<400> SEQUENCE: 22

Asn Asp Trp Ile Ser Glu Asn Ile Ser Glu Pro His Arg Val Gln Ile
1               5                   10                  15

Met Leu Asp Gly Thr Val Arg Val Thr Ile Lys Glu Gly Lys Val Lys
            20                  25                  30

His Leu Phe Gly Val Tyr Arg Ile Glu Asn Ser Leu Glu Ala Met Phe
        35                  40                  45

Lys Glu Thr Ile Ala Asp Leu Pro Val Ala Thr Gln Pro Pro Gln Gly
    50                  55                  60

Pro Val Tyr Thr Ala Lys Glu Leu Ala Gln Gly Asn Ile Ala Pro Val
65                  70                  75                  80

Gln Pro Ala Ala Asn Tyr Tyr Gly Met Ile Glu Gly Arg Gly Asp Pro
                85                  90                  95

Met Thr Ala Phe Glu Ala Leu Ser Val Leu Arg Ser Gln Lys Val Leu
            100                 105                 110

Ala Lys Asp Val Lys Val Asn Thr Arg Arg Ala Gln Val Phe Leu Asn
        115                 120                 125

Lys Val Arg Arg Ile Ala Glu Val Arg Ala Ser Glu Leu Thr Leu Lys
    130                 135                 140

Cys Leu Pro Ile Leu Gly Lys Val Asn Gly Arg Lys Leu Ile Arg Glu
145                 150                 155                 160

Glu Thr Asn Ile Pro Asn Gln Arg Leu Ala Ser Ile Met Thr Ser Ile
                165                 170                 175

Gly Ile Arg Leu Glu Lys Leu Pro Val Val Arg Ala Asn Thr Ser Gly
            180                 185                 190

Ser Lys Phe Arg Gln Ser Ile Leu Glu Lys Met Asp Lys Tyr Glu Asn
        195                 200                 205

Glu Gln Val Pro Gly Leu His Glu Lys Met Trp Ala Ala Phe Leu Ala
    210                 215                 220

Thr Ala Arg Gln Asp Leu Arg Asn Thr Tyr Glu Glu Val Thr Tyr Leu
225                 230                 235                 240

Glu Leu Glu Ala Gly Ile Asn Arg Lys Gly Ala Pro Gly Phe Phe Glu
                245                 250                 255

Lys Glu Ser Ser Ile Gly Glu Val Leu Glu Lys Lys Glu Lys Ile Asp
            260                 265                 270

Val Thr Ile Gln Glu Ile Glu Lys Gly Asn His Leu Tyr Tyr Glu Thr
        275                 280                 285

Ala Met Pro Lys Asn Glu Lys Arg Asp Val Leu Asp Asp Trp Leu Ser
    290                 295                 300
```

```
Glu Asp Phe Val Thr Tyr Lys Lys Pro Arg Val Ile Gln Tyr Pro Glu
305                 310                 315                 320

Ala Val Thr Arg Leu Ala Ile Thr Lys Ile Met Tyr Lys Trp Val Lys
                325                 330                 335

Gln Lys Pro Ile Val Ile Pro Gly Tyr Glu Gly Lys Thr Pro Ile Phe
            340                 345                 350

Glu Ile Phe Glu Lys Val Ser Ala Asp Trp Ala Gln Phe Lys Asn Pro
        355                 360                 365

Val Ala Val Ser Phe Asp Thr Arg Ala Trp Asp Thr Gln Val Thr Arg
    370                 375                 380

Glu Asp Leu Arg Leu Val Gly Arg Ile Gln Lys Tyr Tyr Tyr Lys Lys
385                 390                 395                 400

Lys Tyr Trp Lys Phe Ile Asp Asn Leu Thr Ala Met Met Glu Glu Val
                405                 410                 415

Pro Val Ile Thr Val Glu Gly Asp Met Phe Leu Arg Val Gly Gln Arg
            420                 425                 430

Gly Ser Gly Gln Pro Asp Thr Ser Ala Gly Asn Ser Met Leu Asn Val
        435                 440                 445

Leu Thr Met Leu Val Ala Phe Ser Glu Ser Thr Asn Leu Pro Ile Ala
    450                 455                 460

Ala Ala Trp Lys Ala Cys Arg Ile His Val Cys Gly Asp Asp Gly Phe
465                 470                 475                 480

Leu Ile Thr Glu Ser Glu Leu Gly Arg Lys Phe Ala Glu Lys Gly Val
                485                 490                 495

Pro Leu Leu Ala Ala Phe Gly Lys Pro Gln Lys Ile Thr Glu Gly Ala
            500                 505                 510

Ser Leu Lys Val Thr Ser Asn Phe Asp Gly Ile Glu Phe Cys Ser His
        515                 520                 525

Thr Pro Ile Arg Val Gln Thr Pro Asn Ile Arg Trp Met Pro Ala Arg
    530                 535                 540

Pro Thr Ala Thr Ile Leu Gly Lys Met Ser Thr Arg Leu Gly Glu Gly
545                 550                 555                 560

Ala Thr Arg Ser Gly Glu Glu Tyr Glu Lys Gln Val Ala Phe Ala Tyr
                565                 570                 575

Leu Leu Met Tyr Pro Trp Asn Pro Leu Val Arg Arg Ile Ser Leu Leu
            580                 585                 590

Leu Leu Ser Thr Thr Asp Pro Met Gly Lys Glu Glu Thr Pro Cys Ser
        595                 600                 605

Asp Glu Gly Val Lys Tyr Val Gly Asp Pro Ile Ala Ala Tyr Arg Asp
    610                 615                 620

Val Trp Gly His Lys Leu Glu Asp Val Gly His Val Asp Gln Pro Gln
625                 630                 635                 640

Leu Ser Arg Met Asn Tyr Ser Met Thr Tyr Leu Gly Ile Trp Lys Pro
                645                 650                 655

Lys Thr Ser Gln Arg Leu Val Glu Gln Cys Cys Arg Leu Ala Glu Lys
            660                 665                 670

Ser Asn Cys Val Val Arg Ala Asp Ser Leu Ile Lys Lys Lys Val Lys
        675                 680                 685

Ile Thr Tyr Asp Pro Gly Ile Gly Val Ala Gln Val Ile Arg Arg Trp
    690                 695                 700

Glu Glu Leu Glu Trp Thr Arg Arg Lys Pro Glu Leu Thr Asn Val Ile
705                 710                 715                 720
```

-continued

```
Val Glu Asp Asp Ile Phe Leu Val Leu Trp Lys Arg Phe Ser Lys Tyr
                725                 730                 735

Ile Phe Gln Lys Met Lys Phe Met Gln Arg Met Phe Ala Pro Tyr
            740                 745                 750


<210> SEQ ID NO 23
<211> LENGTH: 17
<212> TYPE: DNA
<213> ORGANISM: Artificial Sequence
<220> FEATURE:
<223> OTHER INFORMATION: laboratory-synthesized DNA sequence

<400> SEQUENCE: 23

tgcctggtat tcgtggc                                                    17


<210> SEQ ID NO 24
<211> LENGTH: 19
<212> TYPE: DNA
<213> ORGANISM: Artificial Sequence
<220> FEATURE:
<223> OTHER INFORMATION: laboratory-synthesized DNA sequence

<400> SEQUENCE: 24

tcatcccatg ttccagagt                                                  19


<210> SEQ ID NO 25
<211> LENGTH: 21
<212> TYPE: DNA
<213> ORGANISM: Artificial Sequence
<220> FEATURE:
<223> OTHER INFORMATION: laboratory-synthesized DNA sequence

<400> SEQUENCE: 25

cctccgtctc cgcggctttg g                                               21


<210> SEQ ID NO 26
<211> LENGTH: 143
<212> TYPE: DNA
<213> ORGANISM: Artificial Sequence
<220> FEATURE:
<223> OTHER INFORMATION: laboratory-synthesized DNA sequence

<400> SEQUENCE: 26

aacaggaaag aactgcctgg tattcgtggc aaccaaagaa gccgcggaga cggaggctaa      60

agaactgcgc accagaggaa ttaacgccac ctattcaggt atagacccta agactctgga     120

acatgggatg accaatcagc cat                                             143
```

UNITED STATES PATENT AND TRADEMARK OFFICE
CERTIFICATE OF CORRECTION

PATENT NO. : 10,633,637 B2
APPLICATION NO. : 15/893358
DATED : April 28, 2020
INVENTOR(S) : Joseph Gilbert Victoria et al.

Page 1 of 1

It is certified that error appears in the above-identified patent and that said Letters Patent is hereby corrected as shown below:

In the Claims

Column 132, Lines 26-27:
In Claim 27, delete "SEQ ID NO:3," and insert -- SEQ ID NO: 3, --, therefor.

Signed and Sealed this
Twenty-first Day of July, 2020

Andrei Iancu
*Director of the United States Patent and Trademark Office*